(12) United States Patent
Mannion et al.

(10) Patent No.: US 11,293,062 B2
(45) Date of Patent: Apr. 5, 2022

(54) BASECALLING FOR STOCHASTIC SEQUENCING PROCESSES

(71) Applicant: Roche Sequencing Solutions, Inc., Pleasanton, CA (US)

(72) Inventors: John Mannion, Mountain View, CA (US); Morgan Mager, Sunnyvale, CA (US)

(73) Assignee: Roche Sequencing Solutions, Inc., Pleasanton, CA (US)

(*) Notice: Subject to any disclaimer, the term of this patent is extended or adjusted under 35 U.S.C. 154(b) by 20 days.

(21) Appl. No.: 16/843,528

(22) Filed: Apr. 8, 2020

(65) Prior Publication Data

US 2020/0232026 A1 Jul. 23, 2020

Related U.S. Application Data

(62) Division of application No. 15/669,207, filed on Aug. 4, 2017, now Pat. No. 10,648,027.

(Continued)

(51) Int. Cl.
*C12Q 1/6869* (2018.01)
*G01N 27/327* (2006.01)
(Continued)

(52) U.S. Cl.
CPC ..... *C12Q 1/6869* (2013.01); *G01N 27/44791* (2013.01); *G16B 40/00* (2019.02); *G16B 40/20* (2019.02); *G16B 45/00* (2019.02)

(58) Field of Classification Search
CPC .................. C12Q 1/6869; G01N 33/48721
See application file for complete search history.

(56) References Cited

U.S. PATENT DOCUMENTS 6,260,034 B1 7/2001 Bjorkesten
7,039,238 B2 5/2006 Sonmez et al.
(Continued)

FOREIGN PATENT DOCUMENTS

EP 3077943 A2 6/2015
WO 2013/041878 A1 3/2013
(Continued)

OTHER PUBLICATIONS

US 9,652,588 B2, 05/2017, Rooyen et al. (withdrawn)
(Continued)

*Primary Examiner* — Alexander S Noguerola
(74) *Attorney, Agent, or Firm* — Kilpatrick Townsend and Stockton LLP

(57) ABSTRACT

Techniques for measuring sequences of nucleic acids are provided. Time-based measurements (e.g., forming a histogram) particular to a given sequencing cell can be used to generate a tailored model. The model can include probability functions, each corresponding to different states (e.g., different states of a nanopore). Such probability functions can be fit to a histogram of measurements obtained for that cell. The probability functions can be updated over a sequencing run of the nucleic acid so that drifts in physical properties of the sequencing cell can be compensated. A hidden Markov model can use such probability functions as emission probabilities for determining the most likely nucleotide states over time. For sequencing cells involving a polymerase, a 2-state classification between bound and unbound states of the polymerase can be performed. The bound regions can be further analyzed by a second classifier to distinguish between states corresponding to different bound nucleotides.

20 Claims, 23 Drawing Sheets

Specification includes a Sequence Listing.

Related U.S. Application Data

(60) Provisional application No. 62/372,258, filed on Aug. 8, 2016, provisional application No. 62/384,650, filed on Sep. 7, 2016.

(51) Int. Cl.
*G01N 27/447* (2006.01)
*G16B 40/00* (2019.01)
*G16B 45/00* (2019.01)
*G16B 40/20* (2019.01)

(56) References Cited

U.S. PATENT DOCUMENTS

| | | |
|---|---|---|
| 7,133,781 B2 | 11/2006 | Toll et al. |
| 8,182,993 B2 | 5/2012 | Tomaney et al. |
| 8,189,892 B2 | 5/2012 | Dimirova et al. |
| 8,370,079 B2 | 2/2013 | Sorenson et al. |
| 8,452,546 B1 | 5/2013 | Lathrop |
| 8,501,405 B2 | 8/2013 | Korlach et al. |
| 8,703,422 B2 | 4/2014 | Tomaney et al. |
| 8,940,507 B2 | 1/2015 | Korlach et al. |
| 9,014,989 B2 | 4/2015 | McMillen et al. |
| 9,017,937 B1 * | 4/2015 | Turner .............. G01N 33/48721 435/6.1 |
| 9,063,156 B2 | 6/2015 | Korlach et al. |
| 9,175,338 B2 | 11/2015 | Flusberg et al. |
| 9,175,341 B2 | 11/2015 | Flusberg et al. |
| 9,175,343 B2 | 11/2015 | Tomaney et al. |
| 9,200,320 B2 | 12/2015 | Korlach et al. |
| 9,235,680 B2 | 1/2016 | Rooyen et al. |
| 9,342,652 B2 | 5/2016 | Rooyen et al. |
| 9,483,610 B2 | 11/2016 | McMillen et al. |
| 9,519,752 B2 | 12/2016 | Rooyen et al. |
| 9,529,967 B2 | 12/2016 | Rooyen et al. |
| 9,576,103 B2 | 2/2017 | McMillen et al. |
| 9,576,104 B2 | 2/2017 | Rooyen et al. |
| 9,679,104 B2 | 6/2017 | Rooyen et al. |
| 9,689,033 B2 | 6/2017 | Stava et al. |
| 9,697,327 B2 | 7/2017 | McMillen et al. |
| 9,746,476 B2 | 8/2017 | Korlach et al. |
| 2013/0217006 A1 | 8/2013 | Sorenson et al. |
| 2013/0316918 A1 | 11/2013 | Jiang et al. |
| 2014/0200166 A1 | 7/2014 | McMillen et al. |
| 2014/0236490 A1 | 8/2014 | McMillen et al. |
| 2014/0309944 A1 | 10/2014 | McMillen et al. |
| 2014/0371109 A1 | 12/2014 | Rooyen et al. |
| 2014/0371110 A1 | 12/2014 | Rooyen et al. |
| 2015/0111759 A1 | 4/2015 | Ju et al. |
| 2015/0119259 A1 | 4/2015 | Ju et al. |
| 2015/0169824 A1 | 6/2015 | Kermani et al. |
| 2015/0227688 A1 | 8/2015 | McMillen et al. |
| 2015/0339437 A1 | 11/2015 | Rooyen et al. |
| 2016/0078170 A1 | 3/2016 | Rooyen et al. |
| 2016/0097093 A1 | 4/2016 | Tomaney et al. |
| 2016/0132638 A1 | 5/2016 | Rooyen et al. |
| 2016/0140290 A1 | 5/2016 | Rooyen et al. |
| 2016/0153038 A1 | 6/2016 | Flusberg et al. |
| 2016/0162634 A1 | 6/2016 | Reid et al. |
| 2016/0171153 A1 | 6/2016 | Rooyen et al. |
| 2016/0180019 A1 | 6/2016 | Rooyen et al. |
| 2016/0203196 A1 | 7/2016 | Schnall-Levin et al. |
| 2016/0246923 A1 | 8/2016 | Rooyen et al. |
| 2016/0246924 A1 | 8/2016 | Rooyen et al. |
| 2016/0328358 A1 | 11/2016 | Helgesen et al. |
| 2016/0364522 A1 | 12/2016 | Frey et al. |
| 2017/0037464 A1 | 2/2017 | Turner et al. |
| 2017/0091383 A1 | 3/2017 | Rooyen et al. |
| 2017/0091427 A1 | 3/2017 | Massingham |
| 2017/0096703 A1 | 4/2017 | Dolan et al. |
| 2017/0124254 A1 | 5/2017 | Rooyen et al. |
| 2017/0161213 A1 | 6/2017 | Rooyen et al. |
| 2017/0169162 A1 | 6/2017 | McMillen et al. |
| 2017/0169165 A1 | 6/2017 | Rooyen et al. |
| 2017/0219557 A1 | 8/2017 | Reid et al. |
| 2017/0233802 A1 | 8/2017 | Flusberg et al. |
| 2017/0255744 A1 | 9/2017 | Rooyen et al. |
| 2017/0268055 A1 | 9/2017 | Stava et al. |
| 2017/0270245 A1 | 9/2017 | Rooyen et al. |
| 2017/0277830 A1 | 9/2017 | Rooyen et al. |
| 2017/0370902 A1 | 12/2017 | Bajaj |
| 2017/0370903 A1 | 12/2017 | Mager et al. |
| 2018/0173844 A1 | 6/2018 | Fernandez-Gomez |

FOREIGN PATENT DOCUMENTS

| | | |
|---|---|---|
| WO | 2015/084985 A2 | 6/2015 |
| WO | 2016/099673 A1 | 6/2016 |
| WO | 2016/164363 A1 | 10/2016 |
| WO | 2017/139492 A1 | 8/2017 |

OTHER PUBLICATIONS

Timp et al., "DNA Base-Calling from a Nanopore Using a Viterbi Algorithm," Biophysical Journal vol. 102 May 2012 L37-L39 plus Supporting Information (Year: 2012).*

International Search Report and Written Opinion dated Nov. 3, 2017 in corresponding PCT/EP2017/069820 filed Aug. 4, 2017, pp. 1-15.

Kester, W. et al., Analog-Digital Conversion, Fundamentals of sampled Data Systems, Chapter 2, (2004), pp. 1-120, www.analog.com.

Lundberg, K.H., MIT Course Notes, Analog-to-Digital Converter Testing, (2002), retrieved from the Internet / pp. 1-20, MIT.

Timp et al, DNA Base-calling from a Nanopore Using a Viterbi Algorighm, Biophysical Journal, May 2012, pp. L-37-L39, vol. 102.

* cited by examiner

Transition Matrix

|    | S0    | S1    | S2    | S3    | S4    |
|----|-------|-------|-------|-------|-------|
| S0 | 0.9   | 0.025 | 0.025 | 0.025 | 0.025 |
| S1 | 0.1   | 0.9   |       |       |       |
| S2 | 0.1   |       | 0.9   |       |       |
| S3 | 0.1   |       |       | 0.9   |       |
| S4 | 0.1   |       |       |       | 0.9   |

FIG. 14A

|    | S0   | S1    | S2    | S3    | S4    |
|----|------|-------|-------|-------|-------|
| S0 | 0.9  | 0.025 | 0.025 | 0.025 | 0.025 |
| S1 | 0.17 | 0.8   | 0.01  | 0.01  | 0.01  |
| S2 | 0.17 | 0.01  | 0.8   | 0.01  | 0.01  |
| S3 | 0.17 | 0.01  | 0.01  | 0.8   | 0.01  |
| S4 | 0.17 | 0.01  | 0.01  | 0.01  | 0.8   |

FIG. 14B

Emission Table

|    | Y0  | Y1   | Y2   | Y3   | Y4   |
|----|-----|------|------|------|------|
| S0 | 0.9 | 0.07 | 0.01 | 0.01 | 0.01 |
| S1 | 0.2 | 0.75 | 0.03 | 0.01 | 0.01 |
| S2 | 0.2 | 0.05 | 0.7  | 0.04 | 0.01 |
| S3 | 0.2 | 0.02 | 0.05 | 0.7  | 0.03 |
| S4 | 0.2 | 0.02 | 0.03 | 0.05 | 0.7  |

SEQUENCE LISTING

```
<160> NUMBER OF SEQ ID NOS: 4

<210> SEQ ID NO 1
<211> LENGTH: 16
<212> TYPE: DNA
<213> ORGANISM: Artificial Sequence
<220> FEATURE:
<223> OTHER INFORMATION: synthetic template layer sequence

<400> SEQUENCE: 1
gagttttatc gcttcc                                                     16

<210> SEQ ID NO 2
<211> LENGTH: 16
<212> TYPE: DNA
<213> ORGANISM: Artificial Sequence
<220> FEATURE:
<223> OTHER INFORMATION: synthetic enzyme layer sequence

<400> SEQUENCE: 2
gaagttatat ccttcc                                                     16

<210> SEQ ID NO 3
<211> LENGTH: 73
<212> TYPE: DNA
<213> ORGANISM: Artificial Sequence
<220> FEATURE:
<223> OTHER INFORMATION: synthetic pore layer sequence

<400> SEQUENCE: 3 gggggaaaa aaaaaaagg gggggtttt tttaaaaaat tatccccccc cccccccct        60 ttccccccc ccc                                                         73

<210> SEQ ID NO 4
```

```
<211> LENGTH: 47
<212> TYPE: DNA
<213> ORGANISM: Artificial Sequence
<220> FEATURE:
<223> OTHER INFORMATION: synthetic nucleotide sequence

<400> SEQUENCE: 4
atagctagca cagagagcga cagcatacta ctcactgacg cagagcg                    47
```

BASECALLING FOR STOCHASTIC SEQUENCING PROCESSES

CROSS-REFERENCES TO RELATED APPLICATIONS

The present application is a divisional of U.S. patent application Ser. No. 15/669,207 filed Aug. 4, 2017, which claims priority from and is a nonprovisional application of U.S. Provisional Application No. 62/372,258, entitled "Basecalling From Nanopore Sequencing Voltages" filed Aug. 8, 2016; and U.S. Provisional Application No. 62/384,650, entitled "Basecalling From Nanopore Sequencing Voltages" filed Sep. 7, 2016, the entire contents of each of which are herein incorporated by reference for all purposes.

REFERENCE TO SUBMISSION OF A SEQUENCE LISTING AS A TEXT FILE

The Sequence Listing written in file SEQ_1181655_P33764US3_ST25.txt created on Mar. 2, 2020, 1,287 bytes, machine format IBM-PC, MS-Windows operating system, is hereby incorporated by reference in its entirety for all purposes.

BACKGROUND

Nanopore membrane devices having pore sizes on the order of one nanometer in internal diameter have shown promise in rapid nucleotide sequencing. When a voltage potential is applied across a nanopore immersed in a conducting fluid, a small ion current attributed to the conduction of ions across the nanopore can exist. The size of the current is sensitive to the pore size and which molecule in the nanopore. The molecule can be a particular tag attached to a particular nucleotide, thereby allowing detection of a nucleotide at a particular position of a nucleic acid. A voltage or other signal in a circuit including the nanopore can be measured (e.g., at an integrating capacitor) as a way of measuring the resistance of the molecule, thereby allowing detection of which molecule is in the nanopore.

A nanopore based sequencing chip may be used for DNA sequencing. A nanopore based sequencing chip can incorporate a large number of sensor cells configured as an array. For example, an array of one million cells may include 1000 rows by 1000 columns of cells.

The signals that are measured can vary from chip to chip and from cell to cell of a same chip due to manufacturing variability. Therefore, it can be difficult to determine the correct molecule, which may be or correspond to the correct nucleotide in a particular nucleic acid or other polymer in a cell. In addition, other time dependent non-idealities in the measured signals can lead to inaccuracies. And, because these circuits employ biochemical circuit elements, e.g., lipid bilayers, nanopores, etc., the variability in the electrical characteristics can be much higher than for traditional semiconductor circuits. Further, sequencing processes are stochastic in nature, and thus variability can occur across a wide variety of systems, including sequencing devices not using nanopores.

Accordingly, improved characterization techniques are desired to improve the accuracy and stability of sequencing processes.

BRIEF SUMMARY

Various embodiments provide techniques and systems related to the measurement of a sequence of a nucleic acid in a sequencing cell, which may be in an array of sequencing cells (e.g., an array of nanopores on a chip).

According to one embodiment, signal values are measured over time from a nucleic acid in a sequencing cell. The signal values can be used to create a histogram from which probability functions for different states (e.g., each corresponding to a different nucleotide) are determined. Each of the probability functions (e.g., as determined using a mixture model) can assign an emission probability of the signal corresponding to a particular nucleotide. Transition probabilities between the states and the emission probabilities can be used to determine a most likely set of set of states over time, thereby providing a measurement of the bases (nucleotides) of the sequence of the nucleic acid. The histogram and the probability functions can be specific to the sequencing cell, thereby providing increased accuracy in determining the sequence of the nucleic acid for that particular sequencing cell. The use of probability functions determined from the histogram can also increase accuracy by tailoring the emission probabilities to the particular data measured.

According to another embodiment, signal values are measured over time from a nucleic acid in a sequencing cell. The signal values can be used to create a histogram from which probability functions for different states (e.g., each corresponding to a different nucleotide) are determined. Each of the probability functions (e.g., as determined using a mixture model) can assign an emission probability of the signal corresponding to a particular nucleotide. The probability functions can be determined further using an initial probability function, e.g., as part of an updating procedure. In this manner, the probability functions can be updated multiple times over the time for sequencing the nucleic acid. These time-dependent probability functions can be used to the most likely states, thereby providing a measurement of the bases (nucleotides) of the sequence of the nucleic acid. The time-dependent probability functions can increase accuracy by accounting for drifts in properties of the physical sequencing cell.

According to another embodiment, signal values are measured over time from a nucleic acid in a sequencing cell. The signal values can correspond to different binding states of a polymerase, including different nucleotide biding states (collectively a bound state) and an unbound state. A 2-states classifier can classify signal values at various time steps as corresponding to the bound state or to the unbound state. A subset of signal corresponding to the bound state can be further analyzed using a second classifier to discriminate between the various nucleotide binding states. The most likely nucleotide binding states can be used to provide a measurement of the bases (nucleotides) of the sequence of the nucleic acid.

Other embodiments are directed to systems and computer readable media associated with methods described herein.

A better understanding of the nature and advantages of embodiments of the present invention may be gained with reference to the following detailed description and the accompanying drawings.

BRIEF DESCRIPTION OF THE DRAWINGS

FIG. 14A shows an example transition matrix of pairwise transition probabilities. FIG. 14B shows an example transition matrix of pairwise transition probabilities with non-zero probabilities between bound states.

TERMS

Figure 1:
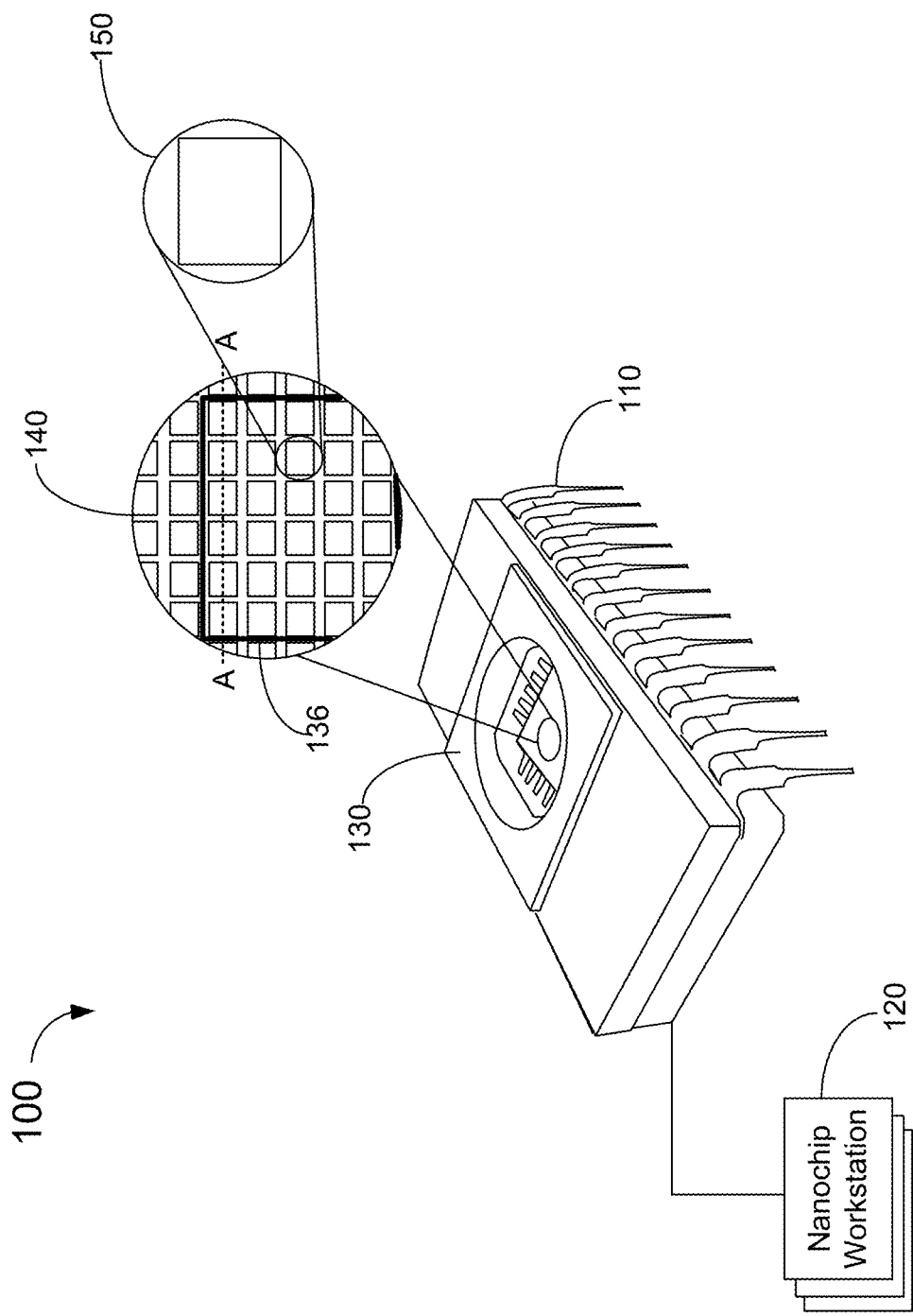
FIG. 1 is a top view of an embodiment of a nanopore sensor chip having an array of nanopore cells according to embodiments of the present invention.

Unless defined otherwise, technical and scientific terms used herein have the same meaning as commonly understood by a person of ordinary skill in the art. Methods, devices, and materials similar or equivalent to those described herein can be used in the practice of disclosed techniques. The following terms are provided to facilitate understanding of certain terms used frequently and are not meant to limit the scope of the present disclosure. Abbreviations used herein have their conventional meaning within the chemical and biological arts.

A "nucleic acid" may refer to deoxyribonucleotides or ribonucleotides and polymers thereof in either single- or double-stranded form. The term may encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs may include, without limitation, phosphorothioates, phosphoramidites, methyl phosphonates, chiral-methyl phosphonates, 2-O-methyl ribonucleotides, peptide-nucleic acids (PNAs). Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid may be used interchangeably with gene, cDNA, mRNA, oligonucleotide, and polynucleotide.

The term "template" may refer to a single stranded nucleic acid molecule that is copied into a complementary strand of DNA nucleotides for DNA synthesis. In some cases, a template may refer to the sequence of DNA that is copied during the synthesis of mRNA.

The term "primer" may refer to a short nucleic acid sequence that provides a starting point for DNA synthesis. Enzymes that catalyze the DNA synthesis, such as DNA polymerases, can add new nucleotides to a primer for DNA replication.

A "polymerase" may refer to an enzyme that performs template-directed synthesis of polynucleotides. The term encompasses both a full length polypeptide and a domain that has polymerase activity. DNA polymerases are well-known to those skilled in the art, and include but are not limited to DNA polymerases isolated or derived from *Pyrococcus furiosus*, *Thermococcus litoralis*, and *Thermotoga*

*maritime*, or modified versions thereof. They include both DNA-dependent polymerases and RNA-dependent polymerases such as reverse transcriptase. At least five families of DNA-dependent DNA polymerases are known, although most fall into families A, B and C. There is little or no sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases α, β, and ε, are implicated in nuclear replication, and a family A polymerase, polymerase γ, is used for mitochondrial DNA replication. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

A "nanopore" refers to a pore, channel or passage formed or otherwise provided in a membrane. A membrane can be an organic membrane, such as a lipid bilayer, or a synthetic membrane, such as a membrane formed of a polymeric material. The nanopore can be disposed adjacent or in proximity to a sensing circuit or an electrode coupled to a sensing circuit, such as, for example, a complementary metal oxide semiconductor (CMOS) or field effect transistor (FET) circuit. In some examples, a nanopore has a characteristic width or diameter on the order of 0.1 nanometers (nm) to about 1000 nm. In some implementations, a nanopore may be a protein.

The term "nucleotide," in addition to referring to the naturally occurring ribonucleotide or deoxyribonucleotide monomers, may be understood to refer to related structural variants thereof, including derivatives and analogs, that are functionally equivalent with respect to the particular context in which the nucleotide is being used (e.g., hybridization to a complementary base), unless the context clearly indicates otherwise.

The term "tag" may refer to a detectable moiety that can be atoms or molecules, or a collection of atoms or molecules. A tag can provide an optical, electrochemical, magnetic, or electrostatic (e.g., inductive, capacitive) signature, which signature may be detected with the aid of a nanopore. Typically, when a nucleotide is attached to the tag it is called a "Tagged Nucleotide." The tag can be attached to the nucleotide via the phosphate moiety.

The term "bright period" may generally refer to the time period when a tag of a tagged nucleotide is forced into a nanopore by an electric field applied through an AC signal. The term "dark period" may generally refer to the time period when a tag of a tagged nucleotide is pushed out of the nanopore by the electric field applied through the AC signal. An AC cycle may include the bright period and the dark period. In different embodiments, the polarity of the voltage signal applied to a nanopore cell to put the nanopore cell into the bright period (or the dark period) may be different. The bright periods and the dark periods can correspond to different portions of an alternating signal relative to a reference voltage.

The term "signal value" may refer to a value of the sequencing signal output from a sequencing cell. According to certain embodiments, the sequencing signal may be an electrical signal that is measured and/or output from a point in a circuit of one or more sequencing cells e.g., the signal value may be (or represent) a voltage or a current. The signal value may represent the results of a direct measurement of voltage and/or current and/or may represent an indirect measurement, e.g., the signal value may be a measured duration of time for which it takes a voltage or current to reach a specified value. A signal value may represent any measurable quantity that correlates with the resistivity of a nanopore and from which the resistivity and/or conductance of the nanopore (threaded and/or unthreaded) may be derived. As another example, the signal value may correspond to a light intensity, e.g., from a fluorophore attached to a nucleotide being catalyzed to a nucleic acid with a polymerase.

The term "histogram" may refer to a data structure storing a count of a number of signal values for each of a specified number of intervals (bins). Each bin can correspond to a discrete value of a signal value (e.g., as determined by a resolution of an ADC) or to range of possible signal values within the interval.

A "nucleotide state" may refer to a state of a nucleic acid at a given time. When a nucleic acid passes through a nanopore, the nucleotide state can correspond to the nucleotide that is determined to be passing through the nanopore at that instant in time. Thus, there may be four nucleotide states. When a polymerase is used, the nucleotide states can correspond to binding states, which may include four binding states of the four nucleotides and a fifth state for no nucleotide being in the active site of the polymerase.

DETAILED DESCRIPTION

Embodiments can provide improved accuracy in the measurements of sequences of nucleic acids, e.g., accounting for the stochastic nature of the sequencing process. Some embodiments can use time-based measurements (e.g., forming a histogram) particular to a given sequencing cell to generate a tailored model for determining the sequences of bases that were measured over a specified time period. The model can include probability functions, each corresponding to different states (e.g., different states of a nanopore). Such probability functions can be fit to a histogram of measurements obtained for that particular cell, thereby providing increased accuracy by tailoring the probability functions to that particular cell. The probability functions can be updated over a sequencing run of the nucleic acid so that drifts in physical properties of the sequencing cell can be taken into account.

In some embodiments, a hidden Markov model (HMM) can use such probability functions as emission probabilities for determining the most likely nucleotide states over time. Other benefits (e.g., for computational efficiency) can be obtained for sequencing cells involving a polymerase by performing a 2-state classification between bound and unbound states of the polymerase (e.g., whether a nucleotide is in an active site of the polymerase or not). The bound regions can be further analyzed by a second classifier to distinguish between states corresponding to different bound nucleotides.

Introductory sections describe various biological processes and electrical devices that may be used in embodiments. Different physical layers and the corresponding data layers of an example sequencing cell are then described. A pipeline for reconstructing signal values measured from the sequencing cell to measure the sequence of a nucleic acid is provided. The use of one or more hidden Markov models is further described. Embodiments may provide quality scores, which can be used to select particular signal values for use in generating a model, e.g., of probability functions. Time-dependent probability functions and uses of two stages of classification are also described.

I. Nanopore Based Sequencing Chip

FIG. 1 is a top view of an embodiment of a nanopore sensor chip 100 having an array 140 of nanopore cells 150. Each nanopore cell 150 includes a control circuit integrated on a silicon substrate of nanopore sensor chip 100. In some embodiments, side walls 136 may be included in array 140 to separate groups of nanopore cells 150 so that each group may receive a different sample for characterization. Each nanopore cell may be used to sequence a nucleic acid. In some embodiments, nanopore sensor chip 100 may include a cover plate 130. In some embodiments, nanopore sensor chip 100 may also include a plurality of pins 110 for interfacing with other circuits, such as a computer processor.

In some embodiments, nanopore sensor chip 100 may include multiple chips in a same package, such as, for example, a Multi-Chip Module (MCM) or System-in-Package (SiP). The chips may include, for example, a memory, a processor, a field-programmable gate array (FPGA), an application-specific integrated circuit (ASIC), data converters, a high-speed I/O interface, etc.

In some embodiments, nanopore sensor chip 100 may be coupled to (e.g., docked to) a nanochip workstation 120, which may include various components for carrying out (e.g., automatically carrying out) various embodiments of the processes disclosed herein, including, for example, analyte delivery mechanisms, such as pipettes for delivering lipid suspension or other membrane structure suspension, analyte solution, and/or other liquids, suspension or solids, robotic arms, computer processor, and/or memory. A plurality of polynucleotides may be detected on array 140 of nanopore cells 150. In some embodiments, each nanopore cell 150 can be individually addressable.

II. Nanopore Sequencing Cell

Nanopore cells 150 in nanopore sensor chip 100 may be implemented in many different ways. For example, in some embodiments, tags of different sizes and/or chemical structures may be attached to different nucleotides in a nucleic acid molecule to be sequenced. In some embodiments, a complementary strand to a template of the nucleic acid molecule to be sequenced may be synthesized by hybridizing differently polymer-tagged nucleotides with the template. In some implementations, the nucleic acid molecule and the attached tags may both move through the nanopore, and an ion current passing through the nanopore may indicate the nucleotide that is in the nanopore because of the particular size and/or structure of the tag attached to the nucleotide. In some implementations, only the tags may be moved into the nanopore. There may also be many different ways to detect the different tags in the nanopores.

A. Nanopore Sequencing Cell Structure

Figure 2:
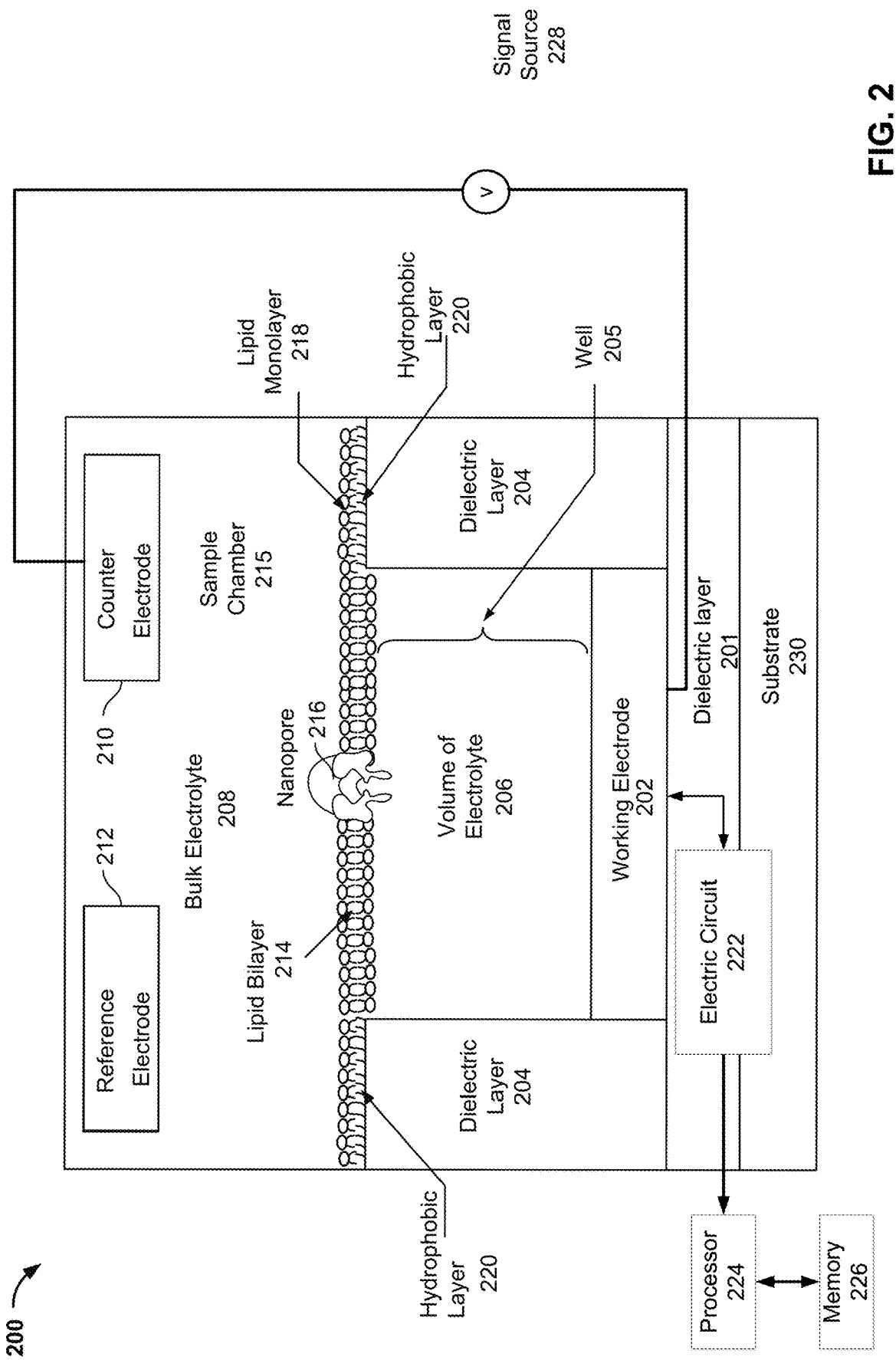
FIG. 2 illustrates an embodiment of a nanopore cell in a nanopore sensor chip that can be used to characterize a polynucleotide or a polypeptide according to embodiments of the present invention.

FIG. 2 illustrates an embodiment of a nanopore cell 200 in a nanopore sensor chip, such as nanopore cell 150 in nanopore sensor chip 100 of FIG. 1, that can be used to characterize a polynucleotide or a polypeptide. Nanopore cell 200 may include a well 205 formed of dielectric layers 201 and 204; a membrane, such as a lipid bilayer 214 formed over well 205; and a sample chamber 215 on lipid bilayer 214 and separated from well 205 by lipid bilayer 214. Well 205 may contain a volume of electrolyte 206, and sample chamber 215 may hold bulk electrolyte 208 containing a nanopore, e.g., a soluble protein nanopore transmembrane molecular complexes (PNTMC), and the analyte of interest (e.g., a nucleic acid molecule to be sequenced).

Nanopore cell 200 may include a working electrode 202 at the bottom of well 205 and a counter electrode 210 disposed in sample chamber 215. A signal source 228 may apply a voltage signal between working electrode 202 and counter electrode 210. A single nanopore (e.g., a PNTMC) may be inserted into lipid bilayer 214 by an electroporation process caused by the voltage signal, thereby forming a nanopore 216 in lipid bilayer 214. The individual membranes (e.g., lipid bilayers 214 or other membrane structures) in the array may be neither chemically nor electrically connected to each other. Thus, each nanopore cell in the array may be an independent sequencing machine, producing data unique to the single polymer molecule associated with the nanopore that operates on the analyte of interest and modulates the ionic current through the otherwise impermeable lipid bilayer.

As shown in FIG. 2, nanopore cell 200 may be formed on a substrate 230, such as a silicon substrate. Dielectric layer 201 may be formed on substrate 230. Dielectric material used to form dielectric layer 201 may include, for example, glass, oxides, nitrides, and the like. An electric circuit 222 for controlling electrical stimulation and for processing the signal detected from nanopore cell 200 may be formed on substrate 230 and/or within dielectric layer 201. For example, a plurality of patterned metal layers (e.g., metal 1 to metal 6) may be formed in dielectric layer 201, and a plurality of active devices (e.g., transistors) may be fabricated on substrate 230. In some embodiments, signal source 228 is included as a part of electric circuit 222. Electric circuit 222 may include, for example, amplifiers, integrators, analog-to-digital converters, noise filters, feedback control logic, and/or various other components. Electric circuit 222 may be further coupled to a processor 224 that is coupled to a memory 226, where processor 224 can analyze the sequencing data to determine sequences of the polymer molecules that have been sequenced in the array.

Working electrode 202 may be formed on dielectric layer 201, and may form at least a part of the bottom of well 205. In some embodiments, working electrode 202 is a metal electrode. For non-faradaic conduction, working electrode 202 may be made of metals or other materials that are resistant to corrosion and oxidation, such as, for example, platinum, gold, titanium nitride, and graphite. For example, working electrode 202 may be a platinum electrode with electroplated platinum. In another example, working electrode 202 may be a titanium nitride (TiN) working electrode. Working electrode 202 may be porous, thereby increasing its surface area and a resulting capacitance associated with working electrode 202. Because the working electrode of a nanopore cell may be independent from the working electrode of another nanopore cell, the working electrode may be referred to as cell electrode in this disclosure.

Dielectric layer 204 may be formed above dielectric layer 201. Dielectric layer 204 forms the walls surrounding well 205. A dielectric material used to form dielectric layer 204 may include, for example, glass, oxide, silicon mononitride (SiN), polyimide, or other suitable hydrophobic insulating material. The top surface of dielectric layer 204 may be silanized. The silanization may form a hydrophobic layer 220 above the top surface of dielectric layer 204. In some embodiments, hydrophobic layer 220 has a thickness of about 1.5 nanometers (nm).

Well 205 formed by walls of the dielectric layer 204 includes volume of electrolyte 206 above working electrode 202. Volume of electrolyte 206 may be buffered and may include one or more of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), manganese chloride ($MnCl_2$), and magnesium chloride ($MgCl_2$). In some embodiments, volume of electrolyte 206 has a thickness of about three microns (μm).

As also shown in FIG. 2, a membrane may be formed on top of dielectric layer 204 and span across well 205. In some embodiments, the membrane may include a lipid monolayer 218 formed on top of hydrophobic layer 220. As the membrane reaches the opening of well 205, lipid monolayer 218 may transition to lipid bilayer 214 that spans across the opening of well 205. The lipid bilayer may comprise or consist of phospholipid, for example, selected from diphytanoyl-phosphatidylcholine (DPhPC), 1,2-diphytanoyl-sn-glycero-3-phosphocholine, 1,2-Di-O-Phytanyl-sn-Glycero-3-phosphocholine (DoPhPC), palmitoyl-oleoyl-phosphatidylcholine (POPC), dioleoyl-phosphatidyl-methylester (DOPME), dipalmitoylphosphatidylcholine (DPPC), phosphatidylcholine, phosphatidylethanolamine, phosphatidylserine, phosphatidic acid, phosphatidylinositol, phosphatidylglycerol, sphingomyelin, 1,2-di-O-phytanyl-sn-glycerol; 1,2-dipalmitoyl-sn-glycero-3-phosphoethanolamine-N-[methoxy(polyethylene glycol)-350]; 1,2-dipalmitoyl-sn-glycero-3-phosphoethanolamine-N-[methoxy (polyethylene glycol)-550]; 1,2-dipalmitoyl-sn-glycero-3-phosphoethanolamine-N-[methoxy(polyethylene glycol)-750]; 1,2-dipalmitoyl-sn-glycero-3-phosphoethanolamine-N-[methoxy(polyethylene glycol)-1000]; 1,2-dipalmitoyl-sn-glycero-3-phosphoethanolamine-N-[methoxy (polyethylene glycol)-2000]; 1,2-dioleoyl-sn-glycero-3-phosphoethanolamine-N-lactosyl; GM1 Ganglioside, Lysophosphatidylcholine (LPC) or any combination thereof.

As shown, lipid bilayer 214 is embedded with a single nanopore 216, e.g., formed by a single PNTMC. As described above, nanopore 216 may be formed by inserting a single PNTMC into lipid bilayer 214 by electroporation. Nanopore 216 may be large enough for passing at least a portion of the analyte of interest and/or small ions (e.g., $Na^+$, $K^+$, $Ca^{2+}$, $Cl^-$) between the two sides of lipid bilayer 214.

Sample chamber 215 is over lipid bilayer 214, and can hold a solution of the analyte of interest for characterization. The solution may be an aqueous solution containing bulk electrolyte 208 and buffered to an optimum ion concentration and maintained at an optimum pH to keep the nanopore 216 open. Nanopore 216 crosses lipid bilayer 214 and provides the only path for ionic flow from bulk electrolyte 208 to working electrode 202. In addition to nanopores (e.g., PNTMCs) and the analyte of interest, bulk electrolyte 208 may further include one or more of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), Manganese chloride ($MnCl_2$), and magnesium chloride ($MgCl_2$).

Counter electrode 210 may be an electrochemical potential sensor. In some embodiments, counter electrode 210 may be shared between a plurality of nanopore cells, and may therefore be referred to as a common electrode. In some cases, the common potential and the common electrode may be common to all nanopore cells, or at least all nanopore cells within a particular grouping. The common electrode can be configured to apply a common potential to the bulk electrolyte 208 in contact with the nanopore 216. Counter electrode 210 and working electrode 202 may be coupled to signal source 228 for providing electrical stimulus (e.g., voltage bias) across lipid bilayer 214, and may be used for sensing electrical characteristics of lipid bilayer 214 (e.g., resistance, capacitance, and ionic current flow). In some embodiments, nanopore cell 200 can also include a reference electrode 212.

In some embodiments, various checks can be made during creation of the nanopore cell as part of calibration. Once a nanopore cell is created, further calibration steps can be performed, e.g., to identify nanopore cells that are performing as desired (e.g., one nanopore in the cell). Such calibration checks can include physical checks, voltage calibration, open channel calibration, and identification of cells with a single nanopore.

B. Detection Signals of Nanopore Sequencing Cell

Nanopore cells in nanopore sensor chip, such as nanopore cells 150 in nanopore sensor chip 100, may enable parallel sequencing using a single molecule nanopore-based sequencing by synthesis (Nano-SBS) technique.

Figure 3:
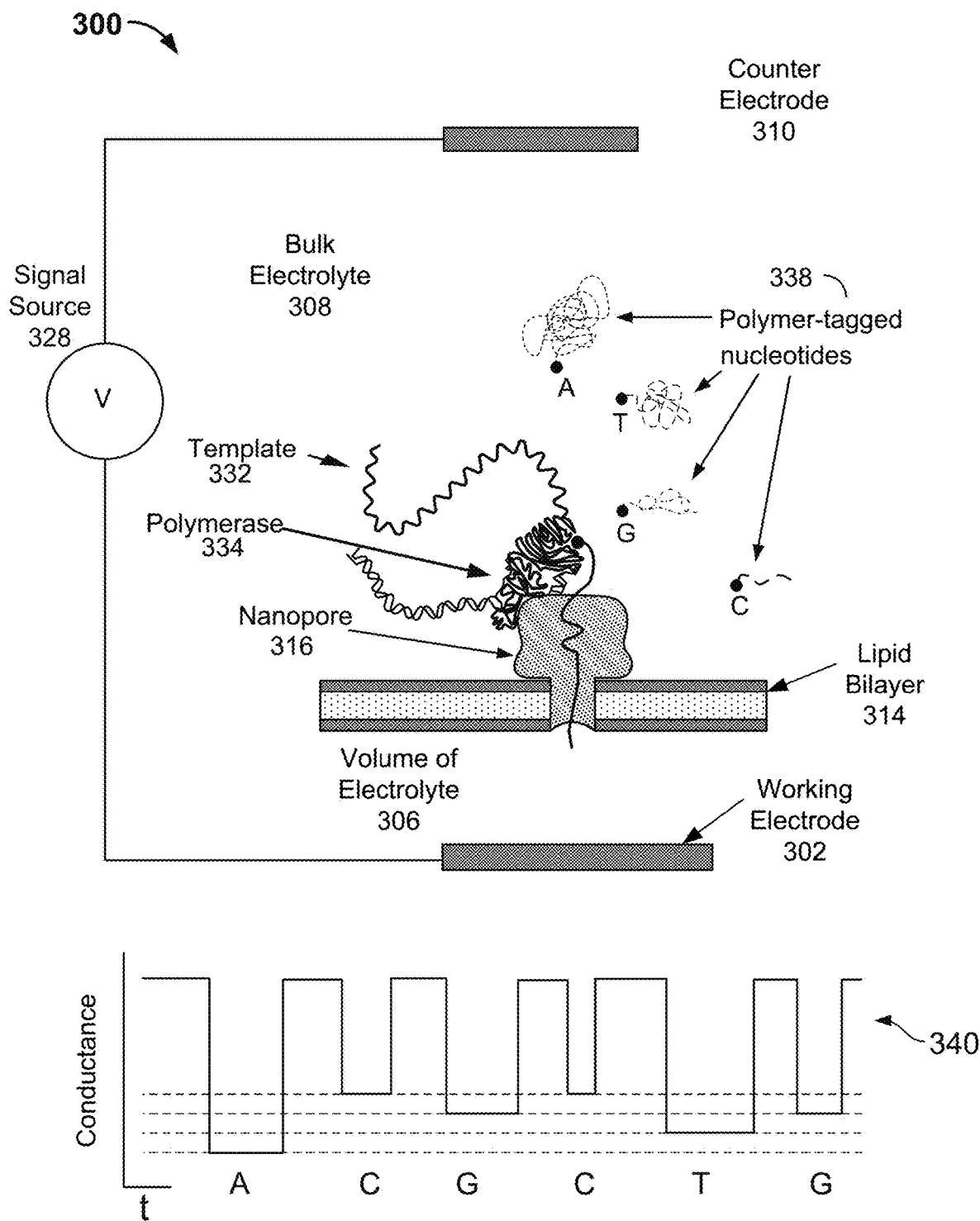
FIG. 3 illustrates an embodiment of a nanopore cell performing nucleotide sequencing using a nanopore-based sequencing-by-synthesis (Nano-SBS) technique according to embodiments of the present invention.

FIG. 3 illustrates an embodiment of a nanopore cell 300 performing nucleotide sequencing using the Nano-SBS technique. In the Nano-SBS technique, a template 332 to be sequenced (e.g., a nucleotide acid molecule or another analyte of interest) and a primer may be introduced into bulk electrolyte 308 in the sample chamber of nanopore cell 300. As examples, template 332 can be circular or linear. A nucleic acid primer may be hybridized to a portion of template 332 to which four differently polymer-tagged nucleotides 338 may be added.

In some embodiments, an enzyme (e.g., a polymerase 334, such as a DNA polymerase) may be associated with nanopore 316 for use in the synthesizing a complementary strand to template 332. For example, polymerase 334 may be covalently attached to nanopore 316. Polymerase 334 may catalyze the incorporation of nucleotides 338 onto the primer using a single stranded nucleic acid molecule as the template. Nucleotides 338 may comprise tag species ("tags") with the nucleotide being one of four different types: A, T, G, or C. When a tagged nucleotide is correctly bound with polymerase 334, the tag may be pulled (loaded) into the nanopore by an electrical force, such as a force generated in the presence of an electric field generated by a voltage applied across lipid bilayer 314 and/or nanopore 316. The tail of the tag may be positioned in the barrel of nanopore 316. The tag held in the barrel of nanopore 316 may generate a unique ionic blockade signal 340 due to the tag's distinct chemical structure and/or size, thereby electronically identifying the added base to which the tag attaches.

As used herein, a "loaded" or "threaded" tag may be one that is positioned in and/or remains in or near the nanopore for an appreciable amount of time, e.g., 0.1 millisecond (ms) to 10,000 milliseconds. In some cases, a tag is loaded in the nanopore prior to being released from the nucleotide. In some instances, the probability of a loaded tag passing through (and/or being detected by) the nanopore after being released upon a nucleotide incorporation event is suitably high, e.g., 90% to 99%.

In some embodiments, before polymerase 334 is connected to nanopore 316, the conductance of nanopore 316 may be high, such as, for example, about 300 picosiemens (300 pS). As the tag is loaded in the nanopore, a unique conductance signal (e.g., signal 340) is generated due to the tag's distinct chemical structure and/or size. For example, the conductance of the nanopore can be about 60 pS, 80 pS, 100 pS, or 120 pS, each corresponding to one of the four types of tagged nucleotides. The polymerase may then undergo an isomerization and a transphosphorylation reaction to incorporate the nucleotide into the growing nucleic acid molecule and release the tag molecule.

In some cases, some of the tagged nucleotides may not match (complementary bases) with a current position of the nucleic acid molecule (template). The tagged nucleotides that are not base-paired with the nucleic acid molecule may also pass through the nanopore. These non-paired nucleotides can be rejected by the polymerase within a time scale that is shorter than the time scale for which correctly paired nucleotides remain associated with the polymerase. Tags bound to non-paired nucleotides may pass through the nanopore quickly, and be detected for a short period of time (e.g., less than 10 ms), while tags bounded to paired nucleotides can be loaded into the nanopore and detected for a long period of time (e.g., at least 10 ms). Therefore, non-paired nucleotides may be identified by a downstream processor based at least in part on the time for which the nucleotide is detected in the nanopore.

A conductance (or equivalently the resistance) of the nanopore including the loaded (threaded) tag can be measured via a current passing through the nanopore, thereby providing an identification of the tag species and thus the nucleotide at the current position. In some embodiments, a direct current (DC) signal can be applied to the nanopore cell (e.g., so that the direction at which the tag moves through the nanopore is not reversed). However, operating a nanopore sensor for long periods of time using a direct current can change the composition of the electrode, unbalance the ion concentrations across the nanopore, and have other undesirable effects that can affect the lifetime of the nanopore cell. Applying an alternating current (AC) waveform can reduce the electro-migration to avoid these undesirable effects and have certain advantages as described below. The nucleic acid sequencing methods described herein that utilize tagged nucleotides are fully compatible with applied AC voltages, and therefore an AC waveform can be used to achieve these advantages.

The ability to re-charge the electrode during the AC detection cycle can be advantageous when sacrificial electrodes, electrodes that change molecular character in the current-carrying reactions (e.g., electrodes comprising silver), or electrodes that change molecular character in current-carrying reactions are used. An electrode may deplete during a detection cycle when a direct current signal is used. The recharging can prevent the electrode from reaching a depletion limit, such as becoming fully depleted, which can be a problem when the electrodes are small (e.g., when the electrodes are small enough to provide an array of electrodes having at least 500 electrodes per square millimeter). Electrode lifetime in some cases scales with, and is at least partly dependent on, the width of the electrode.

Suitable conditions for measuring ionic currents passing through the nanopores are known in the art and examples are provided herein. The measurement may be carried out with a voltage applied across the membrane and pore. In some embodiments, the voltage used may range from −400 mV to +400 mV. The voltage used is preferably in a range having a lower limit selected from −400 mV, −300 mV, −200 mV, −150 mV, −100 mV, −50 mV, −20 mV, and 0 mV, and an upper limit independently selected from +10 mV, +20 mV, +50 mV, +100 mV, +150 mV, +200 mV, +300 mV, and +400 mV. The voltage used may be more preferably in the range of 100 mV to 240 mV and most preferably in the range of 160 mV to 240 mV. It is possible to increase discrimination between different nucleotides by a nanopore using an increased applied potential. Sequencing nucleic acids using AC waveforms and tagged nucleotides is described in US Patent Publication No. US 2014/0134616 entitled "Nucleic Acid Sequencing Using Tags," filed on Nov. 6, 2013, which is herein incorporated by reference in its entirety. In addition to the tagged nucleotides described in US 2014/0134616, sequencing can be performed using nucleotide analogs that lack a sugar or acyclic moiety, e.g., (S)-Glycerol nucleoside triphosphates (gNTPs) of the five common nucleobases: adenine, cytosine, guanine, uracil, and thymine (Horhota et al., Organic Letters, 8:5345-5347 [2006]).

C. Electric Circuit of Nanopore Sequencing Cell

Figure 4:
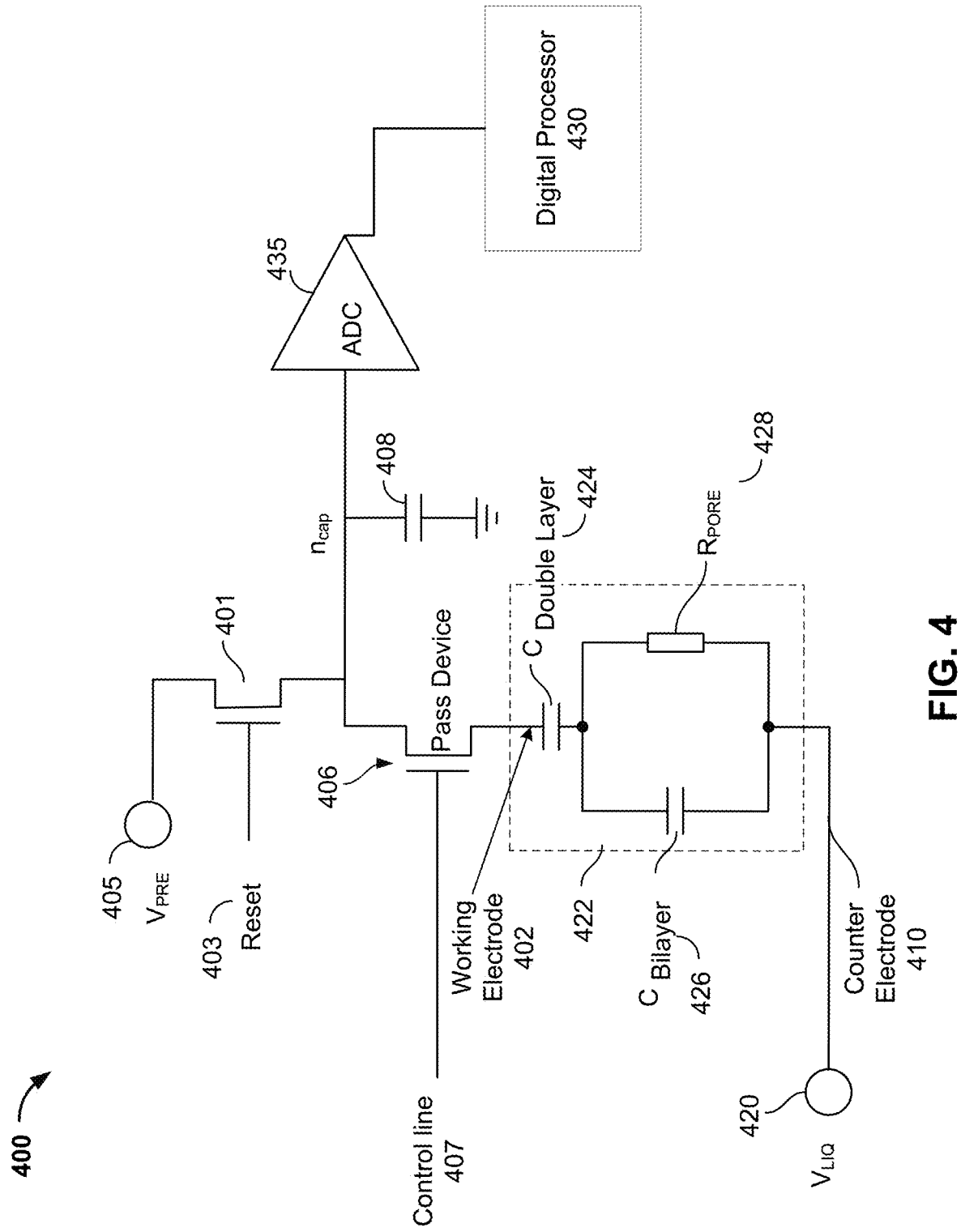
FIG. 4 illustrates an embodiment of an electric circuit in a nanopore cell according to embodiments of the present invention.

FIG. 4 illustrates an embodiment of an electric circuit 400 (which may include portions of electric circuit 222 in FIG. 2) in a nanopore cell, such as nanopore cell 200. As described above, in some embodiments, electric circuit 400 includes a counter electrode 410 that may be shared between a plurality of nanopore cells or all nanopore cells in a nanopore sensor chip, and may therefore also be referred to as a common electrode. The common electrode can be configured to apply a common potential to the bulk electrolyte (e.g., bulk electrolyte 208) in contact with the lipid bilayer (e.g., lipid bilayer 214) in the nanopore cells by connecting to a voltage source $V_{LIQ}$ 420. In some embodiments, an AC non-Faradaic mode may be utilized to modulate voltage $V_{LIQ}$ with an AC signal (e.g., a square wave) and apply it to the bulk electrolyte in contact with the lipid bilayer in the nanopore cell. In some embodiments, $V_{LIQ}$ is a square wave with a magnitude of ±200-250 mV and a frequency between, for example, 25 and 400 Hz. The bulk electrolyte between counter electrode 410 and the lipid bilayer (e.g., lipid bilayer 214) may be modeled by a large capacitor (not shown), such as, for example, 100 μF or larger.

FIG. 4 also shows an electrical model 422 representing the electrical properties of a working electrode 402 (e.g., working electrode 202) and the lipid bilayer (e.g., lipid bilayer 214). Electrical model 422 includes a capacitor 426 ($C_{Bilayer}$) that models a capacitance associated with the lipid bilayer and a resistor 428 ($R_{PORE}$) that models a variable resistance associated with the nanopore, which can change based on the presence of a particular tag in the nanopore. Electrical model 422 also includes a capacitor 424 having a double layer capacitance ($C_{Double\ Layer}$) and representing the electrical properties of working electrode 402 and well 205. Working electrode 402 may be configured to apply a distinct potential independent from the working electrodes in other nanopore cells.

Pass device 406 is a switch that can be used to connect or disconnect the lipid bilayer and the working electrode from electric circuit 400. Pass device 406 may be controlled by control line 407 to enable or disable a voltage stimulus to be applied across the lipid bilayer in the nanopore cell. Before lipids are deposited to form the lipid bilayer, the impedance between the two electrodes may be very low because the well of the nanopore cell is not sealed, and therefore pass device 406 may be kept open to avoid a short-circuit condition. Pass device 406 may be closed after lipid solvent has been deposited to the nanopore cell to seal the well of the nanopore cell.

Circuitry 400 may further include an on-chip integrating capacitor 408 ($n_{cap}$). Integrating capacitor 408 may be pre-charged by using a reset signal 403 to close switch 401, such that integrating capacitor 408 is connected to a voltage source $V_{PRE}$ 405. In some embodiments, voltage source $V_{PRE}$ 405 provides a constant reference voltage with a magnitude of, for example, 900 mV. When switch 401 is closed, integrating capacitor 408 may be pre-charged to the reference voltage level of voltage source $V_{PRE}$ 405.

After integrating capacitor 408 is pre-charged, reset signal 403 may be used to open switch 401 such that integrating capacitor 408 is disconnected from voltage source $V_{PRE}$ 405. At this point, depending on the level of voltage source $V_{LIQ}$, the potential of counter electrode 410 may be at a level higher than the potential of working electrode 402 (and integrating capacitor 408), or vice versa. For example, during a positive phase of a square wave from voltage source $V_{LIQ}$ (e.g., the bright or dark period of the AC voltage source signal cycle), the potential of counter electrode 410 is at a level higher than the potential of working electrode 402. During a negative phase of the square wave from voltage source $V_{LIQ}$ (e.g., the dark or bright period of the AC voltage source signal cycle), the potential of counter electrode 410 is at a level lower than the potential of working electrode 402. Thus, in some embodiments, integrating capacitor 408 may be further charged during the bright period from the pre-charged voltage level of voltage source $V_{PRE}$ 405 to a higher level, and discharged during the dark period to a lower level, due to the potential difference between counter electrode 410 and working electrode 402. In other embodiments, the charging and discharging may occur in dark periods and bright periods, respectively.

Integrating capacitor 408 may be charged or discharged for a fixed period of time, depending on the sampling rate of an analog-to-digital converter (ADC) 435, which may be higher than 1 kHz, 5 kHz, 10 kHz, 100 kHz, or more. For example, with a sampling rate of 1 kHz, integrating capacitor 408 may be charged/discharged for a period of about 1 ms, and then the voltage level may be sampled and converted by ADC 435 at the end of the integration period. A particular voltage level would correspond to a particular tag species in the nanopore, and thus correspond to the nucleotide at a current position on the template.

After being sampled by ADC 435, integrating capacitor 408 may be pre-charged again by using reset signal 403 to close switch 401, such that integrating capacitor 408 is connected to voltage source $V_{PRE}$ 405 again. The steps of pre-charging integrating capacitor 408, waiting for a fixed period of time for integrating capacitor 408 to charge or discharge, and sampling and converting the voltage level of integrating capacitor by ADC 435 can be repeated in cycles throughout the sequencing process.

A digital processor 430 can process the ADC output data, e.g., for normalization, data buffering, data filtering, data compression, data reduction, event extraction, or assembling ADC output data from the array of nanopore cells into various data frames. In some embodiments, digital processor 430 can perform further downstream processing, such as base determination. Digital processor 430 can be implemented as hardware (e.g., in a GPU, FPGA, ASIC, etc.) or as a combination of hardware and software.

Accordingly, the voltage signal applied across the nanopore can be used to detect particular states of the nanopore. One of the possible states of the nanopore is an open-channel state when a tag-attached polyphosphate is absent from the barrel of the nanopore, also referred to herein as the unthreaded state of the nanopore. Another four possible states of the nanopore each correspond to a state when one of the four different types of tag-attached polyphosphate nucleotides (A, T, G, or C) is held in the barrel of the nanopore. Yet another possible state of the nanopore is when the lipid bilayer is ruptured.

When the voltage level on integrating capacitor 408 is measured after a fixed period of time, the different states of a nanopore may result in measurements of different voltage levels. This is because the rate of the voltage decay (decrease by discharging or increase by charging) on integrating capacitor 408 (i.e., the steepness of the slope of a voltage on integrating capacitor 408 versus time plot) depends on the nanopore resistance (e.g., the resistance of resistor $R_{PORE}$ 428). More particularly, as the resistance associated with the nanopore in different states is different due to the molecules' (tags') distinct chemical structures, different corresponding rates of voltage decay may be observed and may be used to identify the different states of the nanopore. The voltage decay curve may be an exponential curve with an RC time constant τ=RC, where R is the resistance associated with the nanopore (i.e., $R_{PORE}$ 428) and C is the capacitance associated with the membrane (i.e., capacitor 426 ($C_{Bilayer}$)) in parallel with R. A time constant of the nanopore cell can be, for example, about 200-500 ms. The decay curve may not fit exactly to an exponential curve due to the detailed implementation of the bilayer, but the decay curve may be similar to an exponential curve and is monotonic, thus allowing detection of tags.

In some embodiments, the resistance associated with the nanopore in an open-channel state may be in the range of 100 MΩ to 20 GΩ. In some embodiments, the resistance associated with the nanopore in a state where a tag is inside the barrel of the nanopore may be within the range of 200 MΩ to 40 GΩ. In other embodiments, integrating capacitor 408 may be omitted, as the voltage leading to ADC 435 will still vary due to the voltage decay in electrical model 422.

The rate of the decay of the voltage on integrating capacitor 408 may be determined in different ways. As explained above, the rate of the voltage decay may be determined by measuring a voltage decay during a fixed time interval. For example, the voltage on integrating capacitor 408 may be first measured by ADC 435 at time t1, and then the voltage is measured again by ADC 435 at time t2. The voltage difference is greater when the slope of the voltage on integrating capacitor 408 versus time curve is steeper, and the voltage difference is smaller when the slope of the voltage curve is less steep. Thus, the voltage difference may be used as a metric for determining the rate of the decay of the voltage on integrating capacitor 408, and thus the state of the nanopore cell.

In other embodiments, the rate of the voltage decay can be determined by measuring a time duration that is required for a selected amount of voltage decay. For example, the time required for the voltage to drop or increase from a first voltage level V1 to a second voltage level V2 may be measured. The time required is less when the slope of the voltage vs. time curve is steeper, and the time required is greater when the slope of the voltage vs. time curve is less steep. Thus, the measured time required may be used as a metric for determining the rate of the decay of the voltage on integrating capacitor $n_{cap}$ 408, and thus the state of the nanopore cell. One skilled in the art will appreciate the various circuits that can be used to measure the resistance of the nanopore, e.g., including current measurement techniques.

In some embodiments, electric circuit 400 may not include a pass device (e.g., pass device 406) and an extra capacitor (e.g., integrating capacitor 408 ($n_{cap}$)) that are fabricated on-chip, thereby facilitating the reduction in size of the nanopore-based sequencing chip. Due to the thin nature of the membrane (lipid bilayer), the capacitance associated with the membrane (e.g., capacitor 426 ($C_{Bilayer}$)) alone can suffice to create the required RC time constant without the need for additional on-chip capacitance. Therefore, capacitor 426 may be used as the integrating capacitor, and may be pre-charged by the voltage signal $V_{PRE}$ and subsequently be discharged or charged by the voltage signal $V_{LIQ}$. The elimination of the extra capacitor and the pass device that are otherwise fabricated on-chip in the electric circuit can significantly reduce the footprint of a single nanopore cell in the nanopore sequencing chip, thereby facilitating the scaling of the nanopore sequencing chip to include more and more cells (e.g., having millions of cells in a nanopore sequencing chip).

D. Data Sampling in Nanopore Cell

To perform sequencing of a nucleic acid, the voltage level of integrating capacitor (e.g., integrating capacitor 408 ($n_{cap}$) or capacitor 426 ($C_{Bilayer}$)) can be sampled and converted by the ADC (e.g., ADC 435) while a tagged nucleotide is being added to the nucleic acid. The tag of the nucleotide can be pushed into the barrel of the nanopore by the electric field across the nanopore that is applied through the counter electrode and the working electrode, for example, when the applied voltage is such that $V_{LIQ}$ is lower than $V_{PRE}$.

1. Threading

A threading event is when a tagged nucleotide is attached to the template (e.g., nucleic acid fragment), and the tag goes in and out of the barrel of the nanopore. This can happen multiple times during a threading event. When the tag is in the barrel of the nanopore, the resistance of the nanopore may be higher, and a lower current may flow through the nanopore.

During sequencing, a tag may not be in the nanopore in some AC cycles (referred to as an open-channel state), where the current is the highest because of the lower resistance of the nanopore. When a tag is attracted into the barrel of the nanopore, the nanopore is in a bright mode. When the tag is pushed out of the barrel of the nanopore, the nanopore is in a dark mode.

2. Bright and Dark Period

During an AC cycle, the voltage on integrating capacitor may be sampled multiple times by the ADC. For example, in one embodiment, an AC voltage signal is applied across the system at, e.g., about 100 Hz, and an acquisition rate of the ADC can be about 2000 Hz per cell. Thus, there can be about 20 data points (voltage measurements) captured per AC cycle (cycle of an AC waveform). Data points corresponding to one cycle of the AC waveform may be referred to as a set. In a set of data points for an AC cycle, there may be a subset captured when, for example, $V_{LIQ}$ is lower than $V_{PRE}$, which may correspond to a bright mode (period) where the tag is forced into the barrel of the nanopore. Another subset may correspond to a dark mode (period) where the tag is pushed out of the barrel of the nanopore by the applied electric field when, for example, $V_{LIQ}$ is higher than $V_{PRE}$.

3. Measured Voltages

For each data point, when the switch 401 is opened, the voltage at the integrating capacitor (e.g., integrating capacitor 408 ($n_{cap}$) or capacitor 426 ($C_{Bilayer}$)) will change in a decaying manner as a result of the charging/discharging by $V_{LIQ}$, e.g., as an increase from $V_{PRE}$ to $V_{LIQ}$ when $V_{LIQ}$ is higher than $V_{PRE}$ or a decrease from $V_{PRE}$ to $V_{LIQ}$ when $V_{LIQ}$ is lower than $V_{PRE}$. The final voltage values may deviate from $V_{LIQ}$ as the working electrode charges. The rate of change of the voltage level on the integrating capacitor may be governed by the value of the resistance of the bilayer, which may include the nanopore, which may in turn include a molecule (e.g., a tag of a tagged nucleotide) in the nanopore. The voltage level can be measured at a predetermined time after switch 401 opens.

Switch 401 may operate at the rate of data acquisition. Switch 401 may be closed for a relatively short time period between two acquisitions of data, typically right after a measurement by the ADC. The switch allows multiple data points to be collected during each sub-period (bright or dark) of each AC cycle of $V_{LIQ}$. If switch 401 remains open, the voltage level on the integrating capacitor, and thus the output value of the ADC, would fully decay and stay there. Instead, when switch 401 is closed, the integrating capacitor is pre-charged again (to $V_{PRE}$) and becomes ready for another measurement. Thus, switch 401 allows multiple data points to be collected for each sub-period (bright or dark) of each AC cycle. Such multiple measurements can allow higher resolution with a fixed ADC (e.g. 8-bit to 14-bit due to the greater number of measurements, which may be averaged). The multiple measurements can also provide kinetic information about the molecule threaded into the nanopore. The timing information may allow the determination of how long a threading takes place. This can also be used in helping to determine whether multiple nucleotides that are added to the nucleic acid strand are being sequenced.

Figure 5:
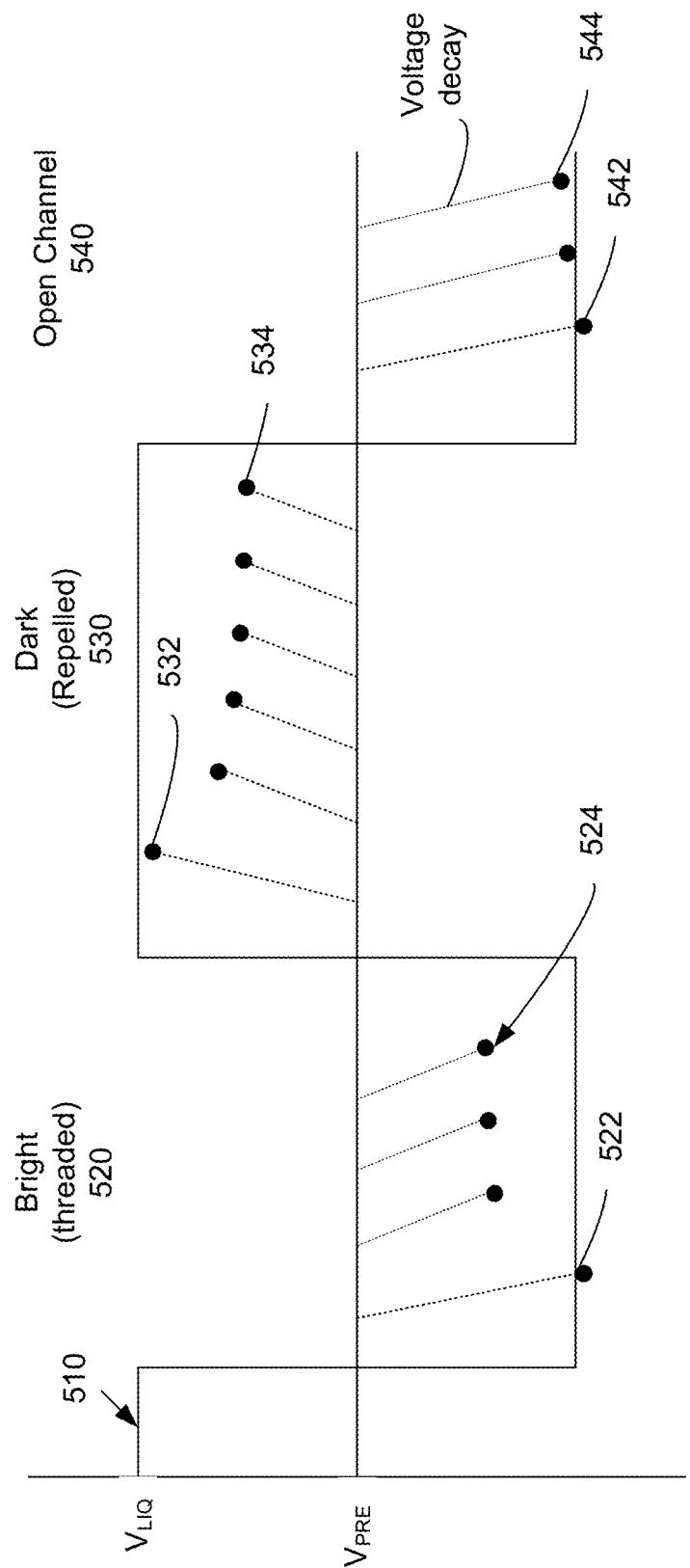
FIG. 5 shows example data points captured from a nanopore cell during bright periods (portions) and dark periods (portions) of AC cycles according to embodiments of the present invention.

FIG. 5 shows example data points captured from a nanopore cell during bright periods and dark periods of AC cycles. In FIG. 5, the change in the data points is exaggerated for illustration purpose. The voltage ($V_{PRE}$) applied to the working electrode or the integrating capacitor is at a constant level, such as, for example, 900 mV. A voltage signal 510 ($V_{LIQ}$) applied to the counter electrode of the nanopore cells is an AC signal shown as a rectangular wave, where the duty cycle may be any suitable value, such as less than or equal to 50%, for example, about 40%.

During a bright period 520, voltage signal 510 ($V_{LIQ}$) applied to the counter electrode is lower than the voltage $V_{PRE}$ applied to the working electrode, such that a tag may be forced into the barrel of the nanopore by the electric field caused by the different voltage levels applied at the working electrode and the counter electrode (e.g., due to the charge on the tag and/or flow of the ions). When switch 401 is opened, the voltage at a node before the ADC (e.g., at an integrating capacitor) will decrease. After a voltage data point is captured (e.g., after a specified time period), switch 401 may be closed and the voltage at the measurement node will increase back to $V_{PRE}$ again. The process can repeat to measure multiple voltage data points. In this way, multiple data points may be captured during the bright period.

As shown in FIG. 5, a first data point 522 (also referred to as first point delta (FPD)) in the bright period after a change in the sign of the $V_{LIQ}$ signal may be lower than subsequent data points 524. This may be because there is no tag in the nanopore (open channel), and thus it has a low resistance and a high discharge rate. In some instances, first data point 522 may exceed the $V_{LIQ}$ level as shown in FIG. 5. This may be caused by the capacitance of the bilayer coupling the signal to the on-chip capacitor. Data points 524 may be captured after a threading event has occurred, i.e., a tag is forced into the barrel of the nanopore, where the resistance of the nanopore and thus the rate of discharging of the integrating capacitor depends on the particular type of tag that is forced into the barrel of the nanopore. Data points 524 may decrease slightly for each measurement due to charge built up at $C_{Double\ Layer}$ 424, as mentioned below.

During a dark period 530, voltage signal 510 ($V_{LIQ}$) applied to the counter electrode is higher than the voltage ($V_{PRE}$) applied to the working electrode, such that any tag would be pushed out of the barrel of the nanopore. When switch 401 is opened, the voltage at the measurement node increases because the voltage level of voltage signal 510 ($V_{LIQ}$) is higher than $V_{PRE}$. After a voltage data point is captured (e.g., after a specified time period), switch 401 may be closed and the voltage at the measurement node will decrease back to $V_{PRE}$ again. The process can repeat to measure multiple voltage data points. Thus, multiple data points may be captured during the dark period, including a first point delta 532 and subsequent data points 534. As described above, during the dark period, any nucleotide tag is pushed out of the nanopore, and thus minimal information about any nucleotide tag is obtained, besides for use in normalization.

FIG. 5 also shows that during bright period 540, even though voltage signal 510 ($V_{LIQ}$) applied to the counter electrode is lower than the voltage ($V_{PRE}$) applied to the working electrode, no threading event occurs (open-channel). Thus, the resistance of the nanopore is low, and the rate of discharging of the integrating capacitor is high. As a result, the captured data points, including a first data point 542 and subsequent data points 544, show low voltage levels.

The voltage measured during a bright or dark period might be expected to be about the same for each measurement of a constant resistance of the nanopore (e.g., made during a bright mode of a given AC cycle while one tag is in the nanopore), but this may not be the case when charge builds up at double layer capacitor 424 ($C_{Double\ Layer}$). This charge build-up can cause the time constant of the nanopore cell to become longer. As a result, the voltage level may be shifted, thereby causing the measured value to decrease for each data point in a cycle. Thus, within a cycle, the data points may change somewhat from data point to another data point, as shown in FIG. 5.

Further details regarding measurements can be found in, for example, U.S. Patent Publication No. 2016/0178577 entitled "Nanopore-Based Sequencing With Varying Voltage Stimulus," U.S. Patent Publication No. 2016/0178554 entitled "Nanopore-Based Sequencing With Varying Voltage Stimulus," U.S. patent application Ser. No. 15/085,700 entitled "Non-Destructive Bilayer Monitoring Using Measurement Of Bilayer Response To Electrical Stimulus," and U.S. patent application Ser. No. 15/085,713 entitled "Electrical Enhancement Of Bilayer Formation," the disclosures of which are incorporated by reference in their entirety for all purposes.

4. Normalization and Base Calling

For each usable nanopore cell of the nanopore sensor chip, a production mode can be run to sequence nucleic acids. The ADC output data captured during the sequencing can be normalized to provide greater accuracy. Normalization can account for offset effects, such as cycle shape, gain drift, charge injection offset, and baseline shift. In some implementations, the signal values of a bright period cycle corresponding to a threading event can be flattened so that a single signal value is obtained for the cycle (e.g., an average) or adjustments can be made to the measured signal to reduce the intra-cycle decay (a type of cycle shape effect). Gain drift generally scales entire signal and changes on the order to hundreds to thousands of seconds. As examples, gain drift can be triggered by changes in solution (pore resistance) or changes in bilayer capacitance. The baseline shift occurs with a timescale of ~100 ms, and relates to a voltage offset at the working electrode. The baseline shift can be driven by changes in an effective rectification ratio from threading as a result of a need to maintain charge balance in the sequencing cell from the bright period to the dark period.

After normalization, embodiments can determine clusters of voltages for the threaded channels, where each cluster corresponds to a different tag species, and thus a different nucleotide. The clusters can be used to determine probabilities of a given voltage corresponding to a given nucleotide. As another example, the clusters can be used to determine cutoff voltages for discriminating between different nucleotides (bases).

Example methods of determining bases of a nucleic acid based on signal measurements are provided below. Although the examples may use voltage measurements for illustration, the example techniques equally apply to other signal measurements, such as current measurements.

III. States of a Sequencing Cell

The sequence of the template nucleic acid is desired, but the specific bases of the sequence need to be inferred from measurements. Various physical characteristics of the system can make it difficult to perform such a determination. Various data layers can correspond to different levels of inference in the process of determining the sequence of the template nucleic acid (template layer) from the signal measurements (e.g., ADC layer). The various data layers include the template layer, the enzyme layer, the pore layer, and the single layer. Prior to discussing the various data layers, various states of incorporation of the nucleotide and threading of a tag are illustrated.

A. Nanopore-Based Sequencing by Synthesis

Figure 6:
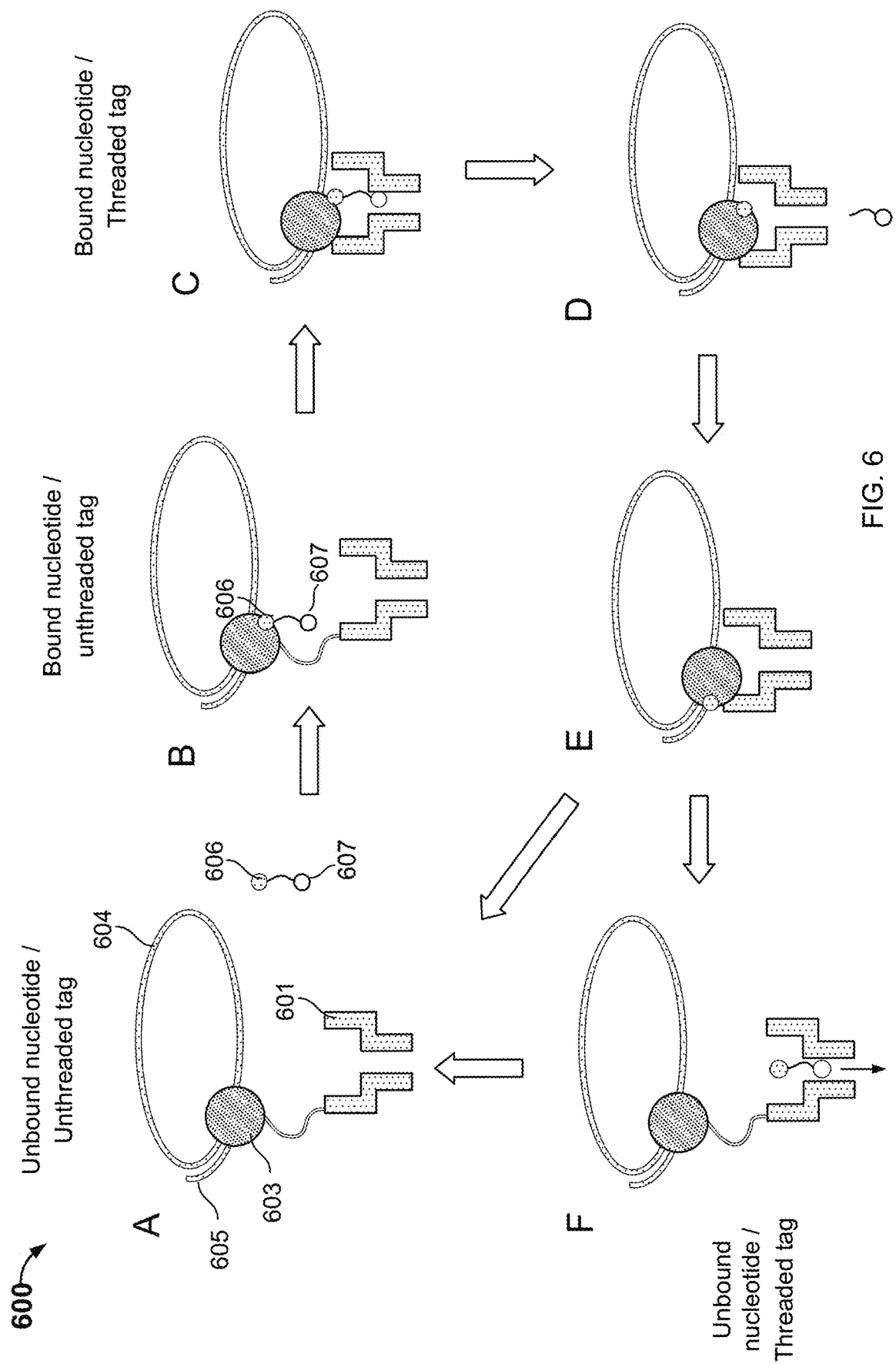
FIG. 6 illustrates an embodiment of a process for nucleic acid sequencing using nucleotides with attached tags according to embodiments of the present invention.

FIG. 6 illustrates an embodiment of a process 600 for nucleic acid sequencing using nucleotides with attached tags according to embodiments of the present invention. Stage A shows a sequencing cell about to perform nucleotide sequencing using such tagged nucleotides. A nanopore 601 is formed in a membrane 602. An enzyme 603 (e.g., a polymerase, such as a DNA polymerase) is associated with the nanopore. In some cases, polymerase 603 is covalently attached to nanopore 601. Polymerase 603 is associated with a nucleic acid molecule 604 to be sequenced. In some embodiments, the nucleic acid molecule 604 is circular. In some cases, nucleic acid molecule 604 is linear. In some embodiments, a nucleic acid primer 605 is hybridized to a portion of nucleic acid molecule 604. Polymerase 603 catalyzes the incorporation of nucleotides 606 onto primer 605 using single stranded nucleic acid molecule 604 as a template. Nucleotides 606 comprise tag species ("tags") 607.

At stage A, a tagged nucleotide (one of four different types: A, T, G, or C) is not associated with the polymerase. Stage A corresponds to an unbound state of a nucleotide (since no nucleotide is bound to polymerase 603 or nucleic acid 604) and an unthreaded state for any tags (since no tags are in pore 601). At stage B, a tagged nucleotide is associated with the polymerase. Stage B corresponds to a bound state for the nucleotide 606, but an unthreaded state for the tag 607.

At stage C, the polymerase is docked to the nanopore, and the tag is threaded into the nanopore. The tag is pulled into the nanopore during docking by an electrical force, such as a force generated in the presence of an electric field generated by a voltage applied across the membrane and/or the nanopore. A "threaded" tag may be one that is positioned in and/or remains in or near the nanopore for an appreciable amount of time, e.g., 0.1 milliseconds to 10,000 milliseconds. Stage C corresponds to a bound state for the nucleotide and an unthreaded state for the tag.

At stage D, the released tag passes through the nanopore. Some of the associated tagged nucleotides are not base paired with the nucleic acid molecule. These non-paired nucleotides typically are rejected by the polymerase within a time scale that is shorter than the time scale for which correctly paired nucleotides remain associated with the polymerase. Since the non-paired nucleotides are only transiently associated with the polymerase, process 600 as shown in FIG. 6 typically does not proceed beyond stage D. For example, a non-paired nucleotide is rejected by the polymerase at stage B or shortly after the process enters stage C.

In various embodiments, before the polymerase is docked to the nanopore, the conductance of the nanopore can be ~300 picosiemens (300 pS). As other examples, at stage C, the conductance of the nanopore can be about 60 pS, 80 pS, 100 pS, or 120 pS, corresponding to one of the four types of tagged nucleotides respectively. The polymerase undergoes an isomerization and a transphosphorylation reaction to incorporate the nucleotide into the growing nucleic acid molecule and release the tag molecule. In particular, as the tag is held in the nanopore, a unique signal is generated due to the tag's distinct chemical structures, thereby identifying the added base electronically. Repeating the cycle (i.e., stage A through E) allows for the sequencing of the nucleic acid molecule.

In some cases, tagged nucleotides that are not incorporated into the growing nucleic acid molecule will also pass through the nanopore, as seen in stage F of FIG. 6. Stage F corresponds to an unbound nucleotide and a threaded tag. The unincorporated nucleotide can be detected by the nanopore in some instances, but embodiments can distinguish between an incorporated nucleotide and an unincorporated nucleotide, e.g., based on the time for which the nucleotide is detected in the nanopore. Tags bound to unincorporated nucleotides pass through the nanopore quickly and are detected for a short period of time (e.g., less than 10 ms), while tags bound to incorporated nucleotides are threaded into the nanopore and detected for a long period of time (e.g., at least 10 ms).

B. Data Layers

Figure 7:
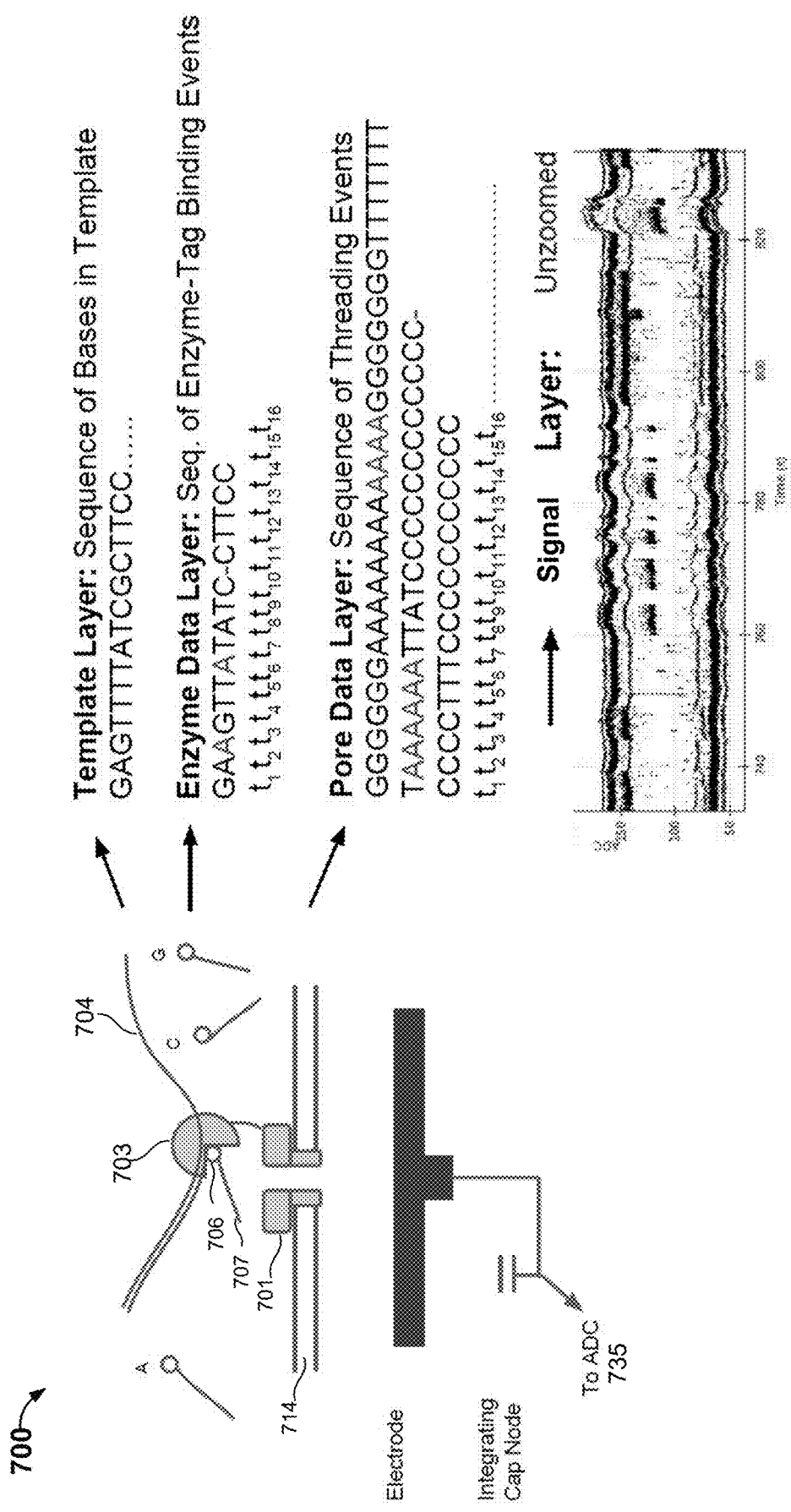
FIG. 7 shows a simplified diagram of a sequencing cell and corresponding data layers according to embodiments of the present invention (Template (SEQ ID NO:1); Enzyme (SEQ ID NO:2); Pore Data (SEQ ID NO:3).

FIG. 7 shows a simplified diagram of a sequencing cell 700 and corresponding data layers according to embodiments of the present invention. A template nucleic acid molecule 704 is shown being sequenced by synthesis by an enzyme 703 using nanopore 701 in membrane 714. FIG. 7 shows enzyme 703 in the process of catalyzing a nucleotide 706 to template nucleic acid molecule 704. Thus, enzyme 703 is in a bound state that corresponds to a base T. A tag 707 is not threaded into nanopore 701, and thus is in an unthreaded state. ADC 735 can measure a resistance (e.g., via voltage or current measurements) of the nanopore 701 in an unthreaded state (as shown) and in a threaded state so as to identify tag 707, which provides an identification of nucleotide 706, thereby obtaining one base in the sequence of template nucleic acid molecule 704.

Measurements of signal values (e.g., voltage values measured by ADC 735) corresponds to the signal layer. The threading events of various tags in nanopore 701 correspond to the pore layer, which can be determined using the measured signal values. A threading event can be identified as corresponding to a particular base based on the measured signal values of the signal layer. The identified threading events over time interval can be used to determine which nucleotide is bound during that time interval. The nucleotides identified as being bound can be used to identify which nucleotides have actually been catalyzed to template nucleic acid molecule 704. Various physical processes can cause difficulties in obtaining an accurate template layer, examples of which are described below.

1. Template Layer

The sequence of template nucleic acid molecule 704 corresponds to the bases in a template layer. The sequence of template nucleic acid molecule 704 should correspond to catalyzed states of nucleotides catalyzed to template nucleic acid molecule 704. FIG. 7 shows an example sequence of GAGTTTTATCGCTTCC (SEQ ID NO:1). This sequence is the desired output of a basecalling procedure implemented by a computer system using the measured signal values. But, as explained below, the sequence is not directly measured. Thus, the template layer can be considered a hidden layer. The template layer can be considered the highest level of information of physical states and can be considered to have zero error, as it corresponds to the actual physical molecule.

2. Enzyme Layer

The enzyme layer is the sequence of binding events of the free-floating nucleotides with the active site associated with enzyme 703. FIG. 7 shows an example enzyme layer GAAGTTATATC-CTTCC (SEQ ID NO:2). The enzyme layer is also not directly measured, and thus can be considered a hidden layer.

The enzyme layer should be composed of binding events for a complimentary nucleotide corresponding to the active site in the template layer. But, it is possible for enzyme 703 to find a matching base, and then let go before the nucleotide catalyzes. The nucleotide (e.g., A) may be bound for relatively long period of time before the nucleotide unbinds from the active site. After the nucleotide falls off, the DNA polymerase waits for another nucleotide to bind to the active site.

During the temporary binding, measurement is performed. It can be difficult to identify the difference between the temporary binding of the nucleotide and a permanent catalysis of the nucleotide. Thus, when another nucleotide of the same type is eventually catalyzed to the active site, it can be difficult to determine whether there is just one A or whether there are multiple A's in a row. Accordingly, an error mode can relate to insertions. In FIG. 7, the red bases correspond to insertions, as can be seen relative to the template layer. This can be seen in the binding at position 2 (corresponding to base A), where the nucleotide with base A did not catalyze and fell off. Another nucleotide with base A was bound and eventually catalyzed, as shown in position 3 of the enzyme layer.

Accordingly, it may be difficult to determine whether there are two As at two consecutive positions, or just one A at one position. Thus, a single binding event can be miscalled as two separate binding events, or two binding events can be miscalled as one binding event. In some embodiments, an insertion error can be identified so as to provide an accurate template layer.

Figure 8:
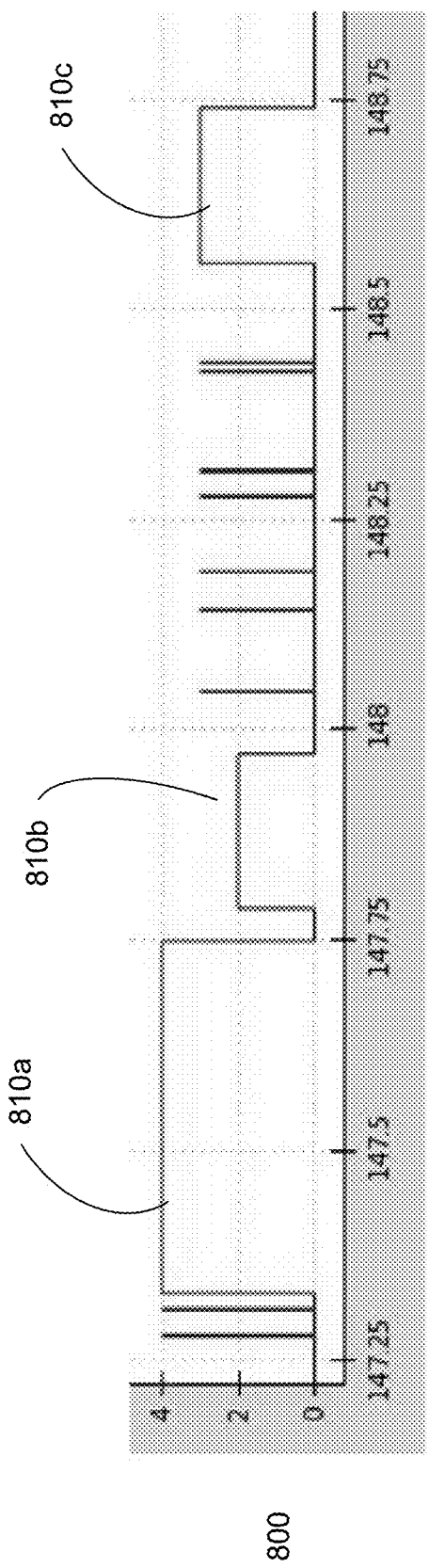
FIG. 8 shows an example enzyme layer composed of pulses according to embodiments of the present invention.
Figure 9:
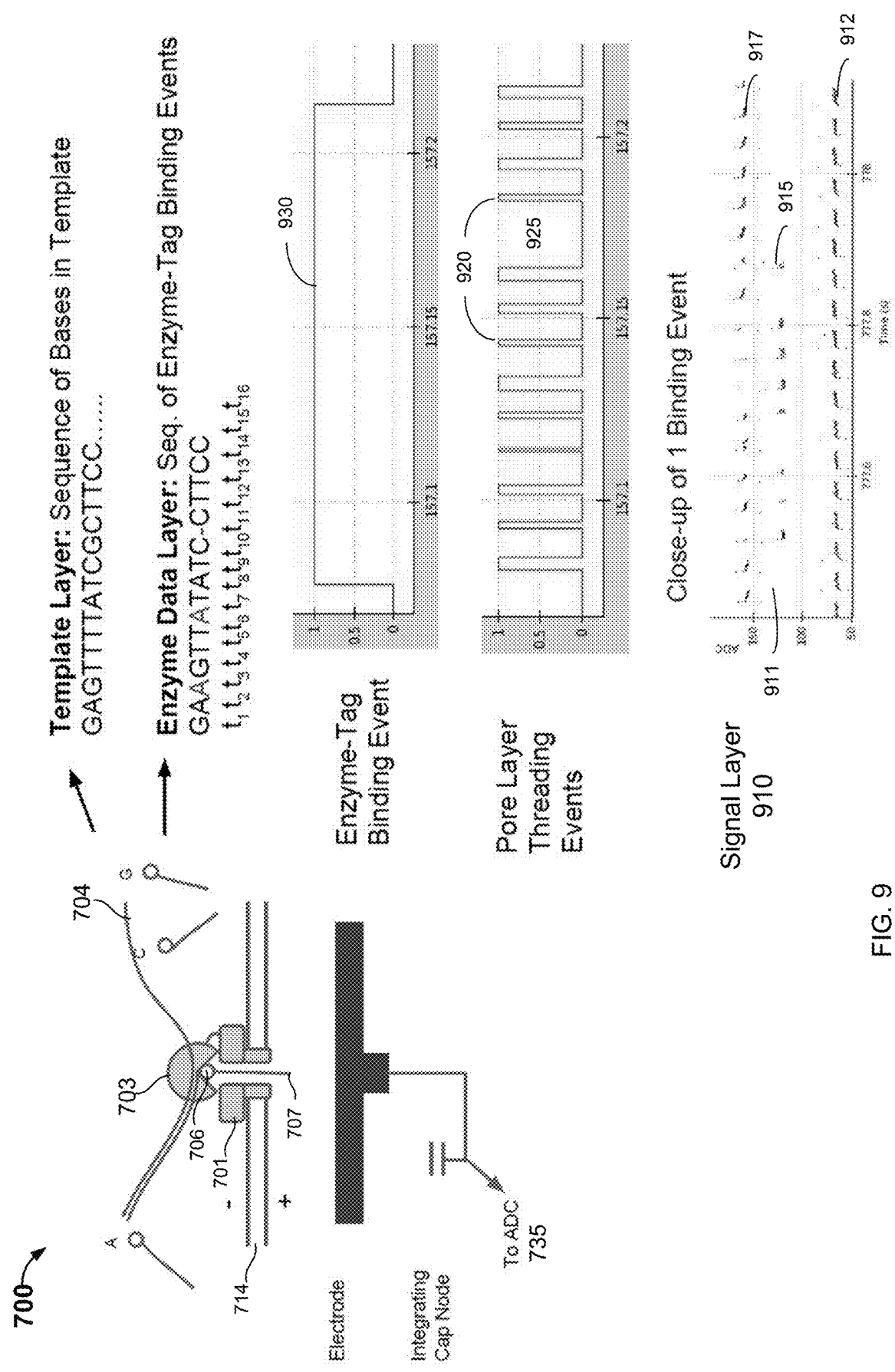
FIG. 9 shows a simplified diagram of a sequencing cell from FIG. 7 in a threaded state and sample data in certain layers according to embodiments of the present invention (Template (SEQ ID NO:1); Enzyme (SEQ ID NO:2); Pore Data (SEQ ID NO:3).

FIG. 8 shows an example enzyme layer 800 composed of pulses, e.g., 810a-810c, according to embodiments of the present invention. Pulses 810a-810c can be determined from multiple threading events, which have a shorter duration. The different pulses can have different heights for different bases. As shown, there are three prominent pulses 810a-810c. The first pulse 810a is relatively long, but it is not known whether pulse 810a corresponds to one binding event, partly because there is not one continuous pulse when working in the AC mode described above. Instead, there is a series of shorter pulses, as shown in FIG. 9.

3. Pore Layer

The pore layer corresponds to threading events are shown below the idealized enzyme-tag binding event. FIG. 7 shows an example pore layer:

(SEQ ID NO: 3)
GGGGGGAAAAAAAAAAAAGGGGGGGTTTTTTTTAAAAAATTATCCC

CCCCCCCC-CCCCTTTCCCCCCCCCCC..

The pore layer is also not directly measured, and thus can be considered a hidden layer.

As shown, there is a series of threading events of a same base, which correspond to one bound state of the enzyme layer. There may be cycles of the AC signal where there is no threading event, as indicated by "-". Thus, the information content can be degraded, as it can be difficult to determine whether there are two binding events or just one long binding event, and whether both binding events resulted in catalysis, and thus correspond to respective positions on the template DNA strand.

The enzyme layer also shows an error at position 7 corresponding to positions 34-39 of the pore layer, where an A was bound for short amount of time and not catalyzed. This error results in the enzyme layer have A instead of T. Such an error can result from the T threading events before the non-catalyzed A being identified as only two catalyzed T's, and not three catalyzed T's.

4. Signal Layer (e.g., ADC Layer)

The signal layer is shown as voltage is measured by ADC 735, which corresponds to voltage measurements made after a specified period of time after a switch is open (e.g., switch 401). The voltage measurement can correspond to a voltage at integrating capacitor 408 ($n_{cap}$). Other signal values may also be used.

The signal layer is an observed layer. From these voltage measurements, embodiments can infer the resistance of the pore during that sampling, although noise can occur, thereby causing errors in the hidden data layers. The ADC is the actual signal measured and from which the hidden data layers are inferred.

In the measured data of this example signal layer, shows two bands at the top and the bottom corresponding to the open channel bright mode and open channel dark mode. The dips in the bright channel correspond to binding events. Each threading event in the pore layer can correspond to a separate cycle in the signal layer within which threading signals were measured. This example signal layer shows measurements corresponding to many cycles of the AC signal described above.

C. Reconstruction of Data Layers

FIG. 9 shows a simplified diagram of sequencing cell 700 from FIG. 7 in a threaded state and sample data in certain layers according to embodiments of the present invention. FIG. 9 shows a signal layer 910 as the observed layer. FIG. 9 shows sequencing cell 700 with nucleotide 706 in a bound state and tag 707 in a threaded state. Such threading of tag 707 will cause the resistance of nanopore 701 to increase, thereby causing the measured ADC values to decrease.

Signal layer 910 shows a close-up of ADC values over approximately 17 cycles of an AC signal being applies to sequencing cell 700. The threaded ADC values for certain cycles can be seen in clusters (e.g., threaded cluster 915), which can be distinguished from cycles not showing any threading (e.g., unthreaded cluster 917). The ADC values of a threaded cluster for a given cycle can correspond to a threading event. Thus, in some embodiments, there can be one threading event at most per cycle, and the threaded clusters of ADC values can correspond to a single binding event 930 in the enzyme layer. In other embodiments, each signal value can be used as an observation for a basecalling procedure (e.g., an HMM).

The ADC values can be normalized, e.g., as disclosed in U.S. patent application Ser. No. 15/632,190, entitled "Formation And Calibration Of Nanopore Sequencing Cells," which is incorporated by reference in its entirety. Such normalization can address shifts in measured values over time, as may occur due to changes in sequencing cell 700 (e.g., due to changes in thickness of membrane 714 or accumulation of charge in sequencing cell 700. After normalizing, ADC values for threading events over multiple cycles for a same tag should provide approximately the same value. The normalization can be seen in threading events 920, which have a same height. Threading events 920 illustrate the reconstruction of the pore data layer. Threading events 920 reflect the threaded clusters in the ADC values, even though these example depictions may not show a one-one correspondence. The clusters of normalized ADC values can be classified, e.g., corresponding to different pore states for different tags or no tag. Such classifications can be performed using a mixture model, which can assign probabilities to different classification (states).

As shown, the threading events form a series of shorter pulses, as there are dark periods 912 between the bright periods 911, within which threading can occur. As shown, the pulses have different widths, as a result of the different delays for the initiation of the threading. When the AC waveform switches from dark mode to bright mode, tag 707 attached to nucleotide 706 may not immediately thread into nanopore 701. There is a strong electric field within the constriction of the nanopore 701, and thus tag 707 can be pulled in right away. But, the tag can be diffusing with random motion, and thus may not interact immediately or during a given cycle with this strong electric field near the pore. Even if there is a well-defined rate of threading, it does not necessarily mean the threading occurs at exactly the same time after the initiation of a bright mode. The rejection of the tag out of the nanopore 701 does occur at the same time, as the tag is already interacting with an electric field.

In FIG. 9, there is one space 925 where there is no pulse, which can occur when no threading occurs in the bright mode of one cycle. Thus, the information of the physical states can be degraded, as it can be difficult to determine whether there are two binding events or just one long binding event. It can also be difficult to determine whether both binding events resulted in catalysis, and thus correspond to respective positions on the template nucleic acid 704.

The series of threading events 920 can be reconstructed to form being event 930. This reconstruction process determines which threading pulses to combine with each other (i.e., merged) to form a binding event of the enzyme layer. In some embodiments, a hidden Markov model (HMM) can be used to determine which threading pulses correspond to a binding event of a particular nucleotide. The template layer can then be reconstructed from the binding events, e.g., via a consensus building procedure.

IV. Reconstruction Pipeline

The process for reconstructing one or more of the hidden layers (e.g., the pore layer, the enzyme layer, and the template layer) can proceed in a basecalling pipeline, which may include hardware and/or software. Such a basecalling pipeline can be implemented using a computer system, e.g., nanochip workstation 120 of FIG. 1, processor 224 of FIG. 2, and/or digital processor 430 of FIG. 4.

Figure 10:
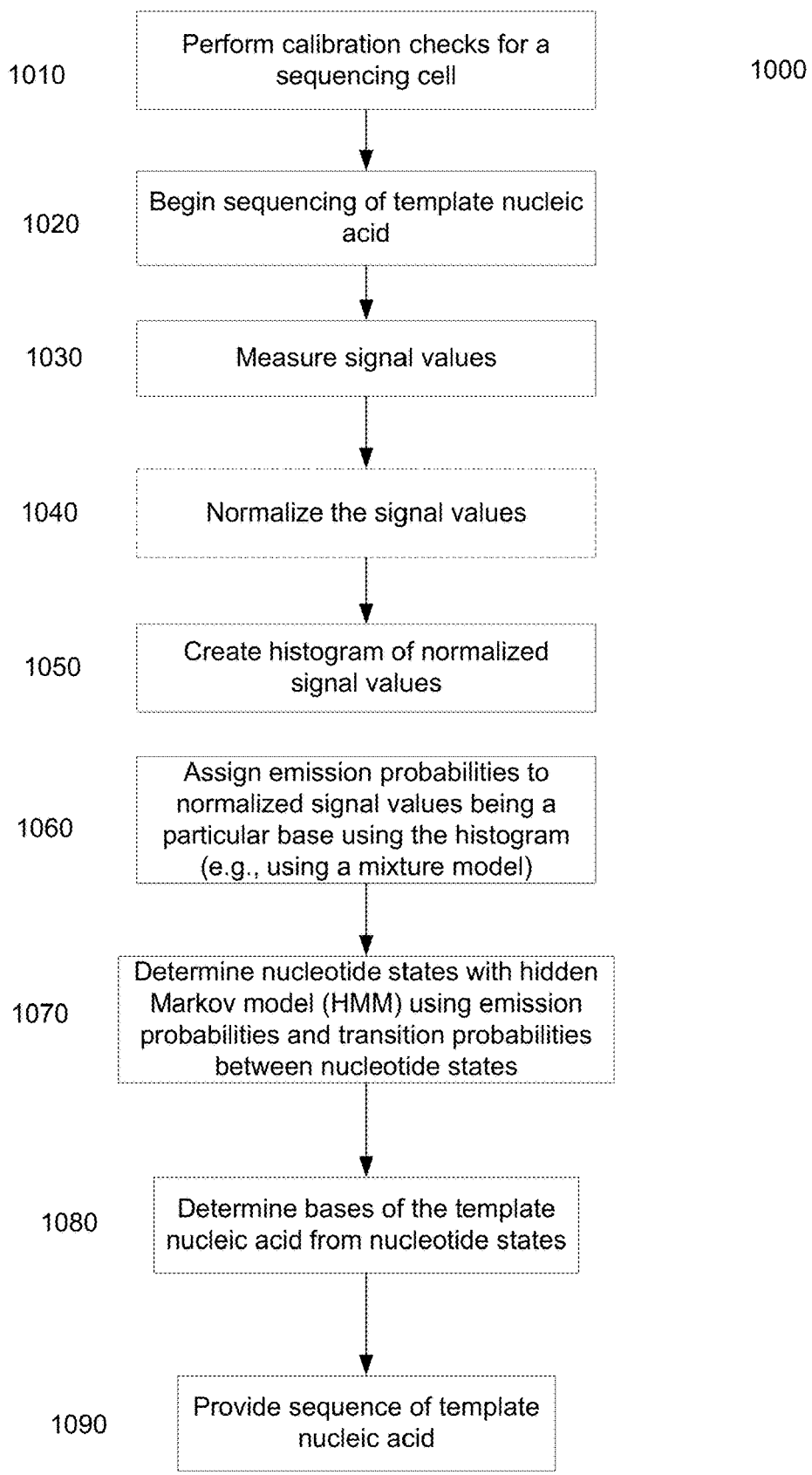
FIG. 10 is a flowchart illustrating a method 1000 for reconstructing physical states of the sequencing cell during a sequencing of a template nucleic acid according to embodiments of the present invention.

FIG. 10 is a flowchart illustrating a method 1000 for reconstructing physical states of the sequencing cell during a sequencing of a template nucleic acid according to embodiments of the present invention. Method 1000 may use signal values measured using a nanopore, a polymerase, or a combination of both, e.g., using tags as described above. Embodiments can apply to nanopore sequencing methods where the nucleic acid passes through the nanopore. Embodiments can also be used with non-nanopore techniques, e.g., where a clear separation between nucleotide incorporation steps does not exist, as may occur when all nucleotides are present in a sequencing cell at a same time.

At block 1010, calibration checks are performed on a sequencing cell. The calibration checks may be performed for all or a portion of the sequencing cells on a sequencing chip. Before the sequencing begins, various checks can be made during a creation of the sequencing cell. Once a sequencing cell is created, further calibration steps can be performed, e.g., to identify sequencing cells that are performing as desired (e.g., one nanopore in the cell). Such calibration checks can include physical checks, voltage calibration, open channel calibration, and identification of wells with single nanopore. Further details of such calibration checks are described in U.S. patent application Ser. No. 15/632,190, entitled "Formation And Calibration Of Nanopore Sequencing Cells." Once the usable cells of a chip are identified, a production mode can be run to sequence nucleic acids, one for each usable cell.

At block 1020, a sequencing mode is initiated for a sequencing cell. The sequencing mode may be initiated by providing tagged nucleotides to the sequencing cell. In some embodiments, a voltage can be applied across the sequencing cell, such as an AC or DC signal, such that electrical signal values can be measured. In other embodiments, a light signal may be measured, e.g., from a fluorophore attached to the nucleotide.

At block 1030, signal values are measured, e.g., as a first set of signal values. Examples of signal values are described herein. The signal values may not be limited to just be of tags attached to nucleotides. One or more signal values may be measured for each cycle of and AC signal. These measured signal values conform signal layer, as described herein. A first set of signal values can include measurements for each of four cell states (e.g., pore states) of the sequencing cell, the four cell states corresponding to different nucleotides of the nucleic acid, as may occur when different tags are threaded in the pore. Other pore states (e.g., open channel states, partial threading states, or unbound threaded states) can be used. When the nucleic acid passes through the nanopore, no open channel state would be needed. In embodiments not using a nanopore, the cell states could correspond to light emission states or electrical states measured as a proxy for the nucleotide being bound to the nucleic acid.

At block 1040, the signal values may optionally be normalized. The normalization can provide greater accuracy, as fluctuations in the physical sequencing cell (e.g., physical structure of membrane 714 or current charge distribution and the sequencing cell) can be accounted for, so that measurements of the same tag species provide similar signal values. Normalization can account for offset effects, such as cycle shape, gain drift, charge injection offset, and baseline shift. Normalized signal values in the bright period can nominally be put onto a scale from 0 to 1 (values slightly larger than 1 could be possible), where 1 correspond to an open channel signal value (i.e., no tag in the pore) and values less than 1 corresponding to different threaded values.

In some embodiments, all of the signal values are measured for a sequencing cell before normalization is performed. In other embodiments, at least some normalization can be performed while signal values are being measured. For example, after a certain number of signal values are measured, a normalization procedure can be started using a first set of measured values, with some new signal values being normalized before measurement ends.

At block 1050, a histogram is created from a set of signal values. The signal values can be normalized, but may not be normalized if the operation of the sequencing cell is sufficiently stable over time. The histogram may form a data structure that stores a plurality of counts. For example, a number of times that an ADC value (e.g., 0-255 or 0-511) is measured can be counted, where each ADC value can correspond to a bin of the histogram. Thus, each count can correspond to a number of signal values within a bin. Besides separate discrete values, a bin can correspond to a range of values. In either implementation, each bin of the histogram can correspond to different numerical values.

Figure 11:
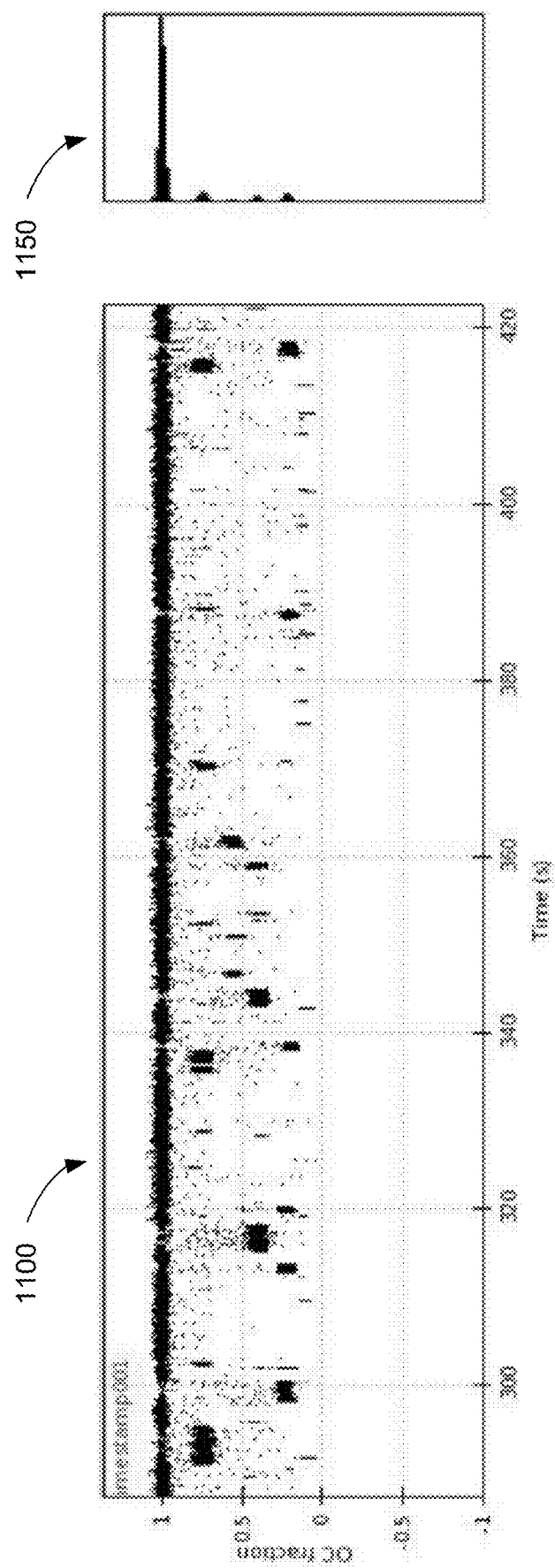
FIG. 11 shows a plot of normalized signal values and a histogram of measurements at different normalized values, as measured by a fraction of the open channel (OC) value according to embodiments of the present invention.

FIG. 11 shows a plot 1100 of normalized signal values and a histogram 1150 of measurements at different normalized values, as measured by a fraction of the open channel (OC) value according to embodiments of the present invention. The vertical axis of plot 1100 shows normalized voltages, where the voltages are divided by an estimate of the open channel voltage at any given time (the horizontal axis). The normalized voltages are expressed as an OC fraction. Other normalized and non-normalized signal values can be used. The voltage values can be ADC values (e.g., measured by ADC 435) corresponding to the median or mean values for a given cycle, or the individual values.

Histogram 1150 shows the number of signal values (OC fraction in this example) that have a particular value. As shown, the vertical axis corresponds to the OC fraction (same as plot 1100). When viewed upright, the horizontal axis would correspond to the OC fraction values. The other axis corresponds to a count of a number of measured signal values having a particular numerical value (e.g., a range or a specific number). As shown, the largest peak (most of the signal values) is near 1, which corresponds to the OC value. The other smaller peaks correspond to different bases: A, C, T, or G. These clusters of signal values can be used to determine base calls, e.g., by fitting a mixture model to the histogram. The substitution error can be low as the peaks are well separated.

At block 1060, emission probabilities are assigned to normalized (or non-normalized) signal values corresponding to particular bases based on the histogram. For each cell state of the four cell states, a probability function can assign probabilities of being in the cell state to the different numerical values. The probability function can be determined using the plurality of counts for the bins of the histogram. Various types of probability functions can be determined, e.g., based on cutoff values, signal values corresponding to peaks in the histograms, or mixture models. Once the probability functions are determined, a probability of a particular signal value measured at a given time corresponding to a particular cell state (e.g., corresponding to C) can be determined using the probability function corresponding to that cell state. Four probabilities can be determined for each signal value; each probability function providing one probability.

For instance, clusters of signal values can be identified in the histogram, e.g., as peaks in the histogram. The clusters can be used to determine cutoff values for discriminating between different bases. The cutoff values can be determined to be between the clusters, e.g., allowing a certain range of normalized signal values to be assigned to a certain base. In such an example, a base (e.g., A) could correspond to normalized signal values between 0.5-0.6, where a probability of 100% is assigned to normalized signal values falling within that range. In other embodiments, a central value can be determined for a given base (e.g., in a middle of the range set by cutoff values), where a probability of a signal value corresponding to the base decreases the further the signal value is away from the central value.

In some embodiments, a mixture model can be determined from the normalized signal values. The mixture model can have 4 probability (mixture) functions for the different bases, and potentially one probability function for the open channel when the implementation involves an open channel. The function for a given cell state (base) can form a distribution that is fit to a peak of the histogram (e.g., a peak being at a signal value that is most common or a centroid of a cluster). In various embodiments, each function can be fit independently to a separate peak (e.g., separate optimization procedures) or the functions can be fit collectively as part of a collective optimization procedure.

The mixture functions can be of various forms, e.g., of Gaussian $$\left(\alpha e^{-\frac{(x-\mu)^2}{2c^2}}\right),$$

where $\alpha$ is the height of the function at its peak, $\mu$ is the center of the peak (e.g., the centroid, mean, median, or mode of the cluster of signal values or expected value for that base) and $c$ is the standard deviation. Another example is a Laplacian mixture model using Laplacian functions:

$$\frac{1}{2b} e^{-\frac{|x-\mu|}{b}},$$

wherein $\mu$ is same as for Gaussian. The area under each of the functions can be constrained to be 1. Various functions having an exponentially decaying function can be used. More complex function with more parameters for a height, position, or width of the mixture function can be used.

Parameters (e.g., width) for the mixture functions can be determined as part of the fitting (optimizing) procedure that identifies optimal parameters for the mixture functions to best approximate the underlying signal values in the histogram. In various implementations, an expectation maximization procedure, moment matching, spectral method, or Markov chain Monte Carlo may be used to optimize the fitting of the mixture functions to the histogram.

In embodiments using a nanopore, the assignment of the probabilities can provide a mechanism for determining the pore layer, with a probability for each pore state (4 threaded states and 1 unthreaded state) being determined using the mixture functions. In some implementations, the mixture model can be applied to the measured signal values for each sequencing cell. In other implementations, the signal values may be stable across cells of a same chip, or from chip to chip. Thus, a same mixture model can be used across cells of a chip or across chips. In embodiments where a mixture model is determined for a specific sequencing cell, an initial mixture model can be determined based on measurements made from other cells or other chips. This initial mixture model can then be updated as part of an optimization (fitting) procedure, such that the optimization can have a better initial estimate.

At block 1070, nucleotide states (e.g., binding states when a polymerase is used) are determined with a hidden Markov model (HMM) using assigned probabilities. The assigned probabilities can be used as the emission values for the HMM. Each mixture function (distributions) of the mixture model can correspond to a hidden binding state of the HMM, thereby providing the binding states of the enzyme layer. For embodiments where synthesis is not used (e.g., the nucleic acid moves through the nanopore), the nucleotide states would not correspond to binding states. Base calls could be generated from the probability functions alone (e.g., taking the one with the highest probability) when there is a one-one correspondence of pore state to enzyme state, but an HMM can provide increased accuracy.

Figure 12:
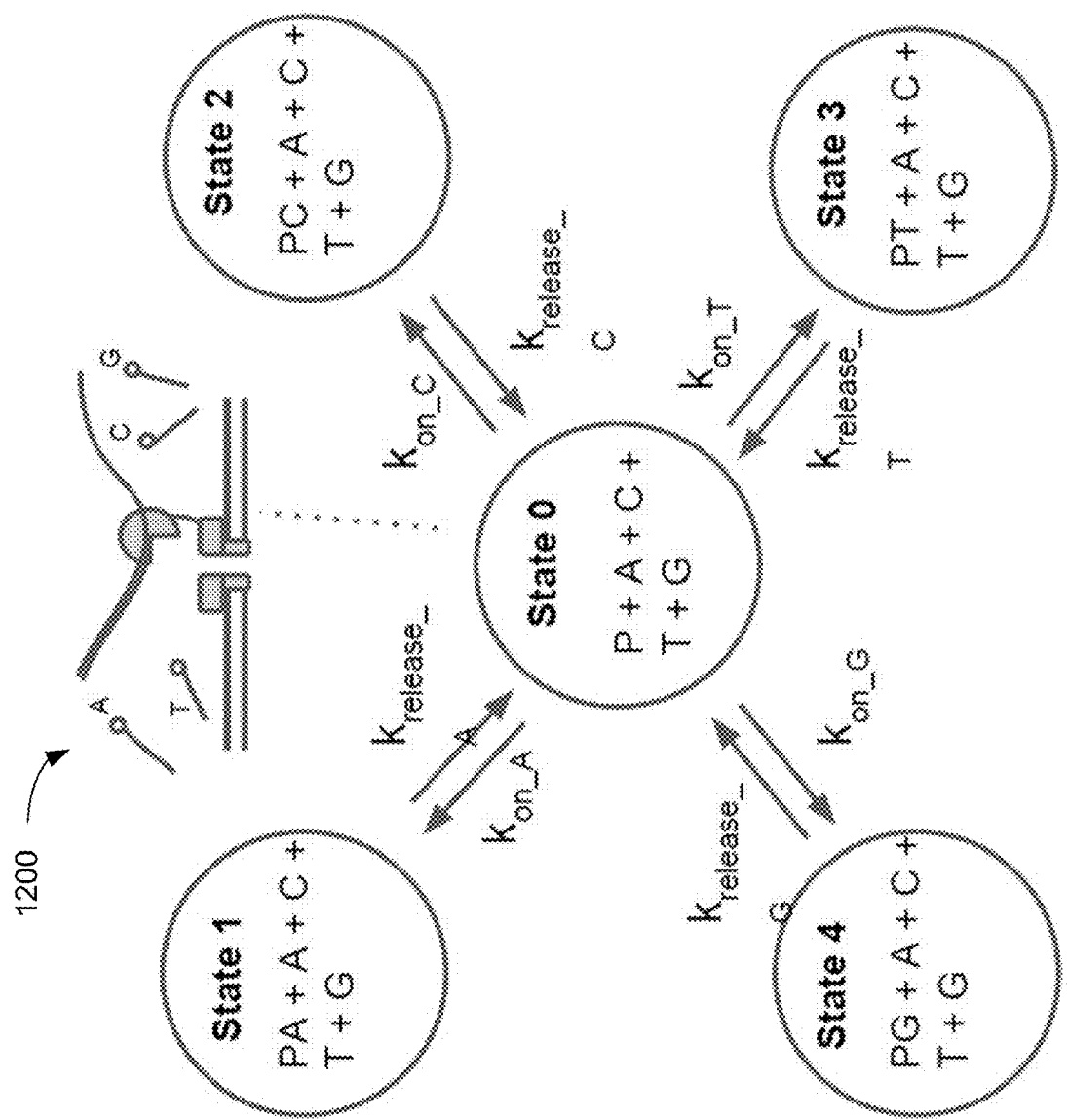
FIG. 12 shows an example HMM that includes 5 states according to embodiments of the present invention.

FIG. 12 shows an example HMM that includes 5 states according to embodiments of the present invention. As shown, state 0 corresponds to no bound tags. State 1 corresponds to a base "A" bound in the active site between the enzyme and the nucleic acid. State 2 corresponds to a base "C" bound in the active site. State 3 corresponds to a base "T" in the active site. State 4 corresponds to a base "G" in the active site. Sequencing cell 1200 is shown in state 0. Although 5 states are shown, more states can be used, e.g., corresponding to unbound but threaded states.

The probability of a measured observable (i.e., signal values) indicating a state is signified by values within the circles. For example, the measured signal for when A in bound can include the measurement of the bound A tag in the pore (signified by PA), as well as any unbound (free) tag (signified by A+C+T+G). A similar configuration is shown for the other states. For State 0, P signifies the probability for no tag being detected in the pore.

The transition rates through time between state 0 and the other binding states are shown with arrows between state 0 and the corresponding state. $K_{on\_A}$=binding rate for nucleotide (tag) A entering the active site. The rate of the nucleotide releasing form the active site is $K_{release\_A}=K_{cat\_A}+K_{off\_A}$, which is the sum of the "catalysis" rate (nucleotide staying on template nucleic acid) and "off" rate (nucleotide falling off the active site). The transition rates can be determined (estimated) in a variety of ways. The transition rates are often stable from one experiment to another, e.g., using the same type of pore, type of tags, and electrolyte solution.

A basecalling procedure can be performed from measurements of one or more cells; after the basecalls are determined, the time between and frequency of transitions between an ordered pair of states can be used to determine the transition rates. In one implementation, the transition rates define an exponential decay over time, and thus can be determined from the observed frequency of transitions at different times. In other embodiments, various values for a transition matrix can be searched to find an optimal set of values, e.g., by sequencing a sample of known genome (e.g., a bacterium) and comparing the output to the known genome. In some embodiments, the transition matrix can be updated for a given sequencing cell, potentially over time, e.g., in a manner similar to the updating of the probability functions over time, as is described in more detail below.

These transition rates (e.g., providing pairwise transition probabilities of a transition matrix) can be used in combination with the assigned probabilities (e.g., as emission probabilities) to determine the most likely series of binding states as a path over time. The HMM can provide a framework for modeling stochastic processes that behave randomly, but according to specific statistical distributions. Homogenous and/or heterogeneous HMMs can be used for various parts of the basecalling process. Further details about the operation of the HMM are provided later.

At block 1080, bases of the template nucleic acid are determined from the nucleotide states. For example, nucleic acids from a sample of a subject can be sequenced on a chip, and the preliminary sequences of nucleotide states can be compared to each other to determine a consensus of bases. Such a process can involve an assembly of the preliminary sequences, e.g., by de novo assembly and/or by comparison to a reference genome. In some implementations, a comparison of a single preliminary sequence to a reference genome can be used by itself as part of the determination of the final sequence of bases for the template layer. Various other techniques (e.g., heuristics) may be used in identifying corrections to the nucleotide states to obtain the sequence of bases.

At block 1090, the sequence of template nucleic acid is provided. As examples, the sequence can be displayed to a user, save in a database for later viewing, or provide to other modules for further processing. For example, the sequences of all or a portion of the nucleic acids on a chip (e.g., from a same sample) can be analyzed to detect variations, such as copy number variations, sequence variations (e.g., single nucleotide polymorphisms, somatic mutations, de novo mutations, etc.) relative to one or more reference genomes, translocations, and the like.

V. Implementation of Hidden Markov Model (HMM)

Various embodiments can use one or more HMMs at various points in the pipeline. For example, a hidden sequence of the HMM can be the sequence of binding states (events) over time. The determination of this hidden can be made more difficult by the use of the AC mode. In DC mode, every time there is a binding event, a tag will thread after some short delay. There will be a series of pulses, each corresponding to a binding event, potentially having different signal levels when consecutive binding events are for a different base. But because AC mode is being used, such pulses are chopped into smaller observations, e.g., the bright periods of the AC signal.

The determination of binding events can be further complicated, as illustrated in the following example. The nanopore might be in a state where A is bound in the active site of the polymerase, and the corresponding tag threads a couple of times in a row so that a couple of short A pulses are seen. Then on the next AC bright period instead of threading, the A tag misses a threading event so that there is a gap between earlier threading cycles and later threading cycles. It can be difficult to determine whether the two sets of threading cycles (with a hap between) correspond to single A or two A's. During the non-threading bright period, it is also possible that there is a free tag of a G (the attached G is not bound) that gets captured in the pore during that time. In this way, there can be multiple tag types contaminating a single binding event. Embodiments using HMMs can be used to address such problems.

A. Time Series for HMM

Figure 13:
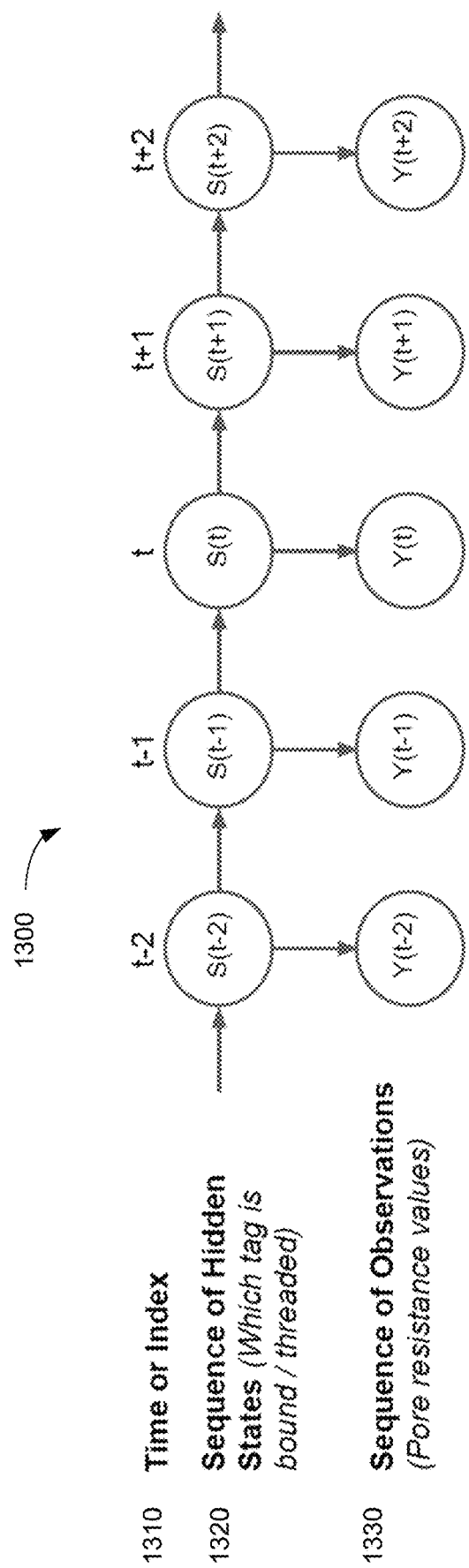
FIG. 13 shows a time trace 1300 for determining hidden states using a hidden Markov model (HMM).

FIG. 13 shows a time trace 1300 for determining hidden states using a hidden Markov model (HMM). In this example, the hidden states may correspond to polymerase (binding) states or pore (threading) states. Trace 1300 a number of discrete time steps 1310 (e.g., identified by a timestamp or a time index). As examples, each time step can correspond to a different measured signal value (i.e., consecutive measured signals could be from a same bright period) or correspond to an AC cycle (e.g., one point per bright period, which may be determined from signal values identified as corresponding to a threading event). In various implementations, a single value can be determined as an average or median of threaded signal values for a given bright period. Threaded signal values of a bright period can be distinguished from non-threaded signals (e.g., as may occur at a beginning of a bright period when threading is not immediate) based on a cutoff value (hard cutoff or soft cutoff with a weight) that distinguishes between an open channel and a threaded channel.

The variable S corresponds to hidden states 1320, e.g., 5 states that include one unbound and four bound states for the different bases when the hidden states are binding states, or one open channel and four threaded states when the hidden states are pore states. The variable Y corresponds to observations 1330, e.g., pore resistance values as may be measured by voltage or current.

In these specific time steps, the system is in one of those five states at any point in time. The hidden states are never actually directly observed, e.g., whether a base is bound in the active side of the polymerase or a tag is threaded in the pore. These observations depend on the state the system is in, but there is not necessarily a one-to-one correspondence between the observation value and the state of the system; a single signal value may not directly correspond to a particular binding state (e.g., as a binding state can include open channel values and threading values when AC mode is used or as unbound tags may enter the pore). Such a time series of states can be determined based on the emission probability of an observation value at a time step corresponding to a particular state and the transition probability from the state at time t to the state at time t+1. The probability of future states can depend only on the present state, and not those that came before it, thereby making the process memoryless.

In various embodiments, there may be multiple hidden layers (e.g., data layers described above), which may be determined separately via separate HMMs or condensed into one hidden layer for determination by one HMM. As an example involving multiple hidden layers, one HMM can be used to determine the hidden pore states over time, and a HMM can use the pore states as the observation values for determining the binding states. As another example, a first HMM (or other filtering procedure) can distinguish between bound and unbound states using the measured signal values, and a second HMM can use the measured signal values obtained during the time intervals that correspond to a bound state to determine which bases are bound at different times. The filtering procedure can reduce the search space so that the HMM only needs to distinguish between the four bound states. Such a filtering procedure is described in more detail in a later section.

B. Defining States

An initial part of the HMM process is describing the various possible states. As mentioned above, in some embodiments, there can be 5 enzyme states corresponding to the four bound states for the four bases (potentially corresponding to one collective bound state) and one unbound state. A variety of states can be defined for pore states. For instance, two states of threaded and non-threaded (open channel) can be defined, e.g., when a filtering procedure is use to identify times corresponding to bound states and unbound states. In this instance, two probability functions can be determined (e.g., for a mixture model): one threaded probability function and one unthreaded probability function. Five pore states can be defined when the threaded states are broken up into four threaded states for the different tags.

In some embodiments, the polymerase states and the pore states can be determined with one HMM, and thus a more hidden states may exist for one hidden layer. For example, a tag attached to an unbound nucleotide (referred to as an unbound tag) can pass through the nanopore, thereby causing a signal that is particular to the type of tag being unbound, e.g., unbound G tag. There can also be combination of states, e.g., an A tag is bound but not threaded and an unbound G tag is threaded.

Such combined states can be referred to as system states. System states can include no nucleotide bound and no tag thread, no nucleotide bound and a free tag threaded, no nucleotide bound and no tag thread but with a background structure (e.g., the polymerase structure being near the pore so as to change the pore resistance). Accordingly, there can be six system states for the unbound polymerase corresponding to six possible pore states: unthreaded, 4 for different tags threaded, and one for background. Each of the bound polymerase states can correspond to six system states, thereby providing 30 system states in such an example. The actual polymerase states can be extracted from the determined system states in order to obtain the polymerase states.

Other possible states include partially bound states, which correspond to a particular tag being partially threaded in the nanopore. These partially bound states can also be referred to as partially integrated states, as the amount of accumulated charge at the capacitor (e.g., capacitor 408) before the ADC (e.g., ADC 435) is only a portion of what the amount would be, since the tag was in the pore for only part of the measurement cycle. For instance, the pore/tag combination will have a certain resistance when the tag is in the pore the whole time. A different amount of charge will accumulate then if that tag threaded halfway through the integration time (e.g., between switch 401 being opened and measurement by ADC 435), resulting in a different measurement for the resistance of the pore/tag combination. These partial integration states can depend on when the threading happens. Such a partial state can also be defined for embodiments measuring other signals, such as current or light intensity.

Such a large number of system states can be computationally expensive for CPU time and memory storage, as the computational requirements scale as the number of states squared. Some embodiments can reduce such computational effort by breaking up the problem into pore states (e.g., involving a mixture model) and then using an HMM on the polymerase states. As mentioned above, embodiments can further provide increased computational efficiency by using two HMMs: first HMM identifying bound states from unbound states and a second HMM differentiating between the different bases for the bound states.

C. Transition Probabilities

Once the states have been defined, transition probabilities between the states can be determined. Such pairwise transition probabilities form a transition matrix. The transition matrix is a square matrix. Thus, if there were 30 states, the transition matrix would be a 30×30 matrix. The transition matrix describes the probability through time for the sequencing cell moving from one state to the next state based on a knowledge of the statistics of transitioning between these states.

The values in the matrices can be determined from physical measurements. One measurement is the threading rate. In some embodiments, as there is new data, parameters (e.g., the transition or emission probabilities) that do not depend on other parameters can be directly fit through observation. Then, those now calibrated parameters can be input into a more complex model for determining the transition probabilities. Another parameter includes a suspected duration of a binding event, which affects the corresponding transition probability. In some implementations, the duration is not reset for every new data set. Estimator functions can become more accurate, and new measurements can be taken. Some embodiments can have a cycle where an estimation and re-estimation loop is run over many experiments. Each parameter in the HMM can be treated somewhat differently. Some parameters can require a long time to calibrate, while other parameters can be more stable.

FIG. 14A shows an example transition matrix of pairwise transition probabilities. Five states are show, e.g., corresponding to one unbound state and four bound states for the four bases. The rows correspond to the starting state, and the columns correspond to the ending state. The total for any given row is 1. The transition probabilities reflect the state diagram depicted in FIG. 12. The blank matrix elements are 0. Transitions that are zero or extremely low represent no probability or very small probability for making a particular transition.

The diagonal elements are the highest. When a cell is in state S1, the cell is most likely to stay in S1 for the next cycle. Thus, the diagonal values in the transition matrix may be close to one. For example, if a current polymerase state for a given bright period is that A is bound, the next bright period is likely to also have A bound (e.g., as the corresponding tag for A will be threaded again). In general, whatever state the polymerase is in, the next state is most likely to be the same because the states are longer lived than the observation times. The off-diagonal terms of the transition matrix provide transitions from one state to another. Any of the various states (e.g., as described herein) can be included in the transition matrix.

Some of the additional states may only be able to be reached from a certain subset of other state. Such restrictions can be coded into the transition matrix. For example, the system can only get to S1 from state S0 (unbound) before reaching state S3. Thus, S0 can be considered a transition state in that way, as it is between two other states. Such restrictions and transitions can provide important information because certain physical properties can be known about the system. In some embodiments, a transition between two bound states can have a non-zero probability. FIG. 14B shows an example transition matrix of pairwise transition probabilities with non-zero probabilities between bound states.

D. Emission Probabilities

An emission table or function provides information about an observed parameter for a given state. For example, each state may generally have a particular range of values for the observed parameter, e.g., a voltage or current associated with a particular tag being in the nanopore.

1. Table

Figures 15A, 15B:
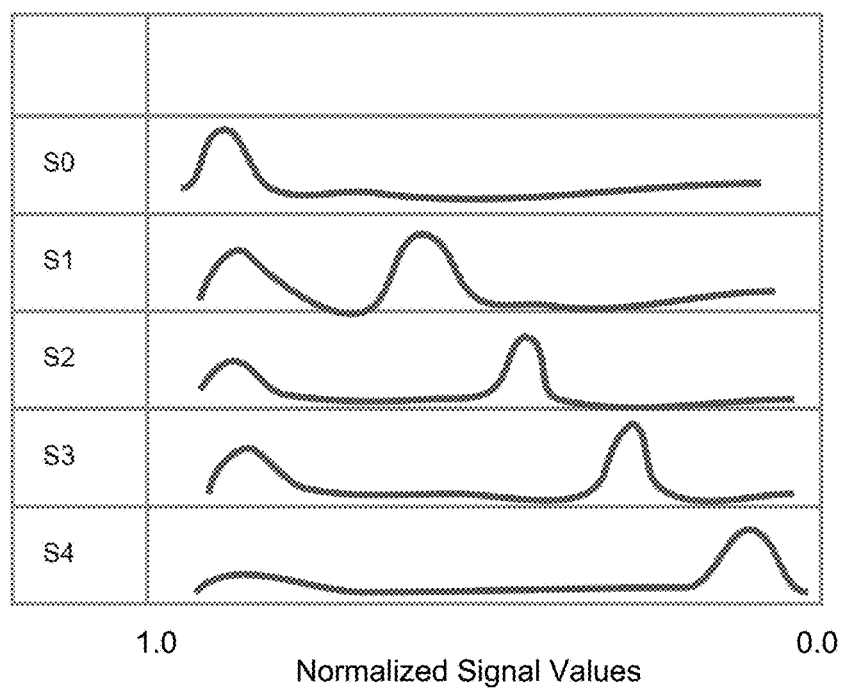
FIG. 15A shows an example emission table including a probability of the observed parameter being in different ranges for each five states.
FIG. 15B shows example emission probability functions for each of 5 states (S0-S4) according to embodiments of the present invention.

FIG. 15A shows an example emission table including a probability of the observed parameter being in different ranges for each five states. The rows correspond to the five states S0-S4, e.g., corresponding to one unbound state and four bound states. The columns Y0-Y4 correspond to different ranges of signal values (e.g., for normalized signal values), such as: Y0 corresponds to (>0.9); Y1 corresponds to (0.9-0.67); Y2 corresponding to (0.45-0.67); Y3 corresponds to (0.23-0.45); and Y4 corresponds to (0.0-0.23). Although 5 ranges are shown, additional ranges may be used. The ranges can be disjoint with values between the ranges being ignored with zero probability of being in a given state.

Any numerical value for a signal within a given range (e.g., for Y2) corresponds to a given column in the emission table. This column then provides the probabilities of being in each of the five states for a signal measured within the range. For S1, it is most likely to observe Y1, but it is not impossible to observe values from the other ranges. Thus, instead of assigning each numerical value in the range a separate probability, there is a hard cut off for the one probability being assigned for that signal value. A certain amount of information may be lost when discretizing the signal values in this manner, but use of the table may be more efficient.

The Baum-Welch algorithm could be used to determine the transmission matrix and the emission matrix, as well as solve. However, such a technique is computationally expensive. Instead, embodiments can use probability functions.

2. Emission Probability Functions

An emission function (e.g., a probability density function, PDF) can provide the probability as a continuous function, as opposed to treating all values of the observed parameter within the same range as having a same probability of occurring. The PDF can provide a probability for being in each of the states for a given value of the observed parameter.

FIG. 15B shows example emission probability functions for each of 5 states (S0-S4) according to embodiments of the present invention. The vertical axis for each of the functions is probability, and the horizontal axis is the value of the observed parameter (signal value). For example, the horizontal axis can be an OC fraction of FIG. 11, with the horizontal axis starting at about 1 on the left and extending to 0 toward the right.

Consistent with FIG. 11, the open channel state most likely has signal values near 1.0. Each of the pore states for different tags has a peak at a different numerical value. In some embodiments, each of the threaded pore states can have some non-zero probability near the open channel value, e.g., due to partial threading or slow threading, thereby having a bright period include open channel measurements.

3. Determining Probability Functions Using Histogram

In some embodiments, peak and/or valley detection techniques can be performed to determine the locations of the peaks. For instance, a Davies valley detection approach may be used, e.g., where valleys can be converted into peaks in a negative direction, and the separation between the inverted valleys can be identified as peaks. Various peak and/or valley detection techniques can be used, as will be appreciated by one skilled in the art. The histogram may be smoothed, e.g., using kernel density estimation (KDE) to smooth out binning artifacts, thereby allowing peak detection to be performed more easily.

In some implementations, the peak detection can advantageously have no assumptions about data shape, number of peaks, etc. Without such assumption, all of the signal values for a given sequencing cell for a given run may be needed. Requiring all of the data is referred to as offline, and can delay throughput. The peak detection can work well for poorly-formed or very sparse data. Such detection can be helped by specifying the number of peaks that should exist (e.g., 5 peaks corresponding to 5 pore states). Thus, the location of the five highest peaks can be used for determining the emission probability functions.

Probability functions can be determined based on the locations of the peaks. For example, a same probability function with a same width can be centered at each peak. As another example, each probability function can independently be fit to just data near the peak, thereby allowing a determining of a width (e.g., width at half maximum) of the probability function for each of the pore states.

In further implementations, a specified number of probability functions can be fit to the histogram (or a smoothed histogram). The probability functions can be part of a mixture model, with each probability function being a mixture component, each corresponding to a different pore state. Thus, all of the different probability functions can be treated as coming from different components in a mixture model. In one embodiment, a Laplacian mixture model is used, and may be updated online as more signal values are obtained. Initial values for the parameters for the mixture model (or other PDFs) can be determined based on measurements from other sequencing cells using similar pores and tags. In this manner, the optimization procedure can fit the probability functions more efficiently. Such parameters can include locations for the peaks of the PDFs and widths of the PDFs.

Figure 16:
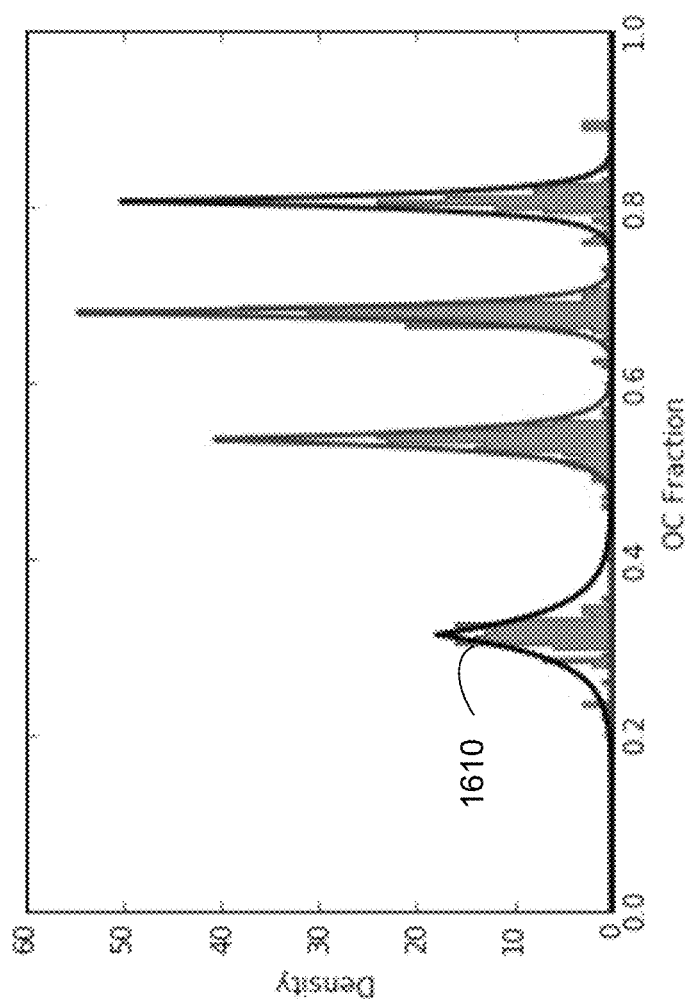
FIG. 16 shows example probability functions for four pore states according to embodiments of the present invention.

FIG. 16 shows example probability functions (PDFs) for four pore states according to embodiments of the present invention. Each of the pore states has an emission function, with each being peaked at a different OC fraction value, which is an example of a normalized signal value. As can be seen, the probability functions are fit to the histogram, with the heights of the probability functions corresponding to the peaks in the histogram and the widths of the probability functions corresponding to the spread in the bin counts near the peaks.

The PDF 1610 corresponds to state 1. When the OC fraction is about 0.3, the nanopore is most likely in state 1. Similarly, an OC fraction of ~0.55 suggests state 2 is most likely, and so on. The emission PDFs may overlap leading to some cross talk between the different bound tags (states), but the peaks are generally separated.

Accordingly, for given signal value, the PDF for each state can be used to provide a probability of being in that state for that given signal value. If the signal value was at the peak of a PDF, then the corresponding state would have a high probability. If a PDF had a tail that did cover the signal value, the probability would be smaller but still finite. Accordingly, the measured signal can be used to determine the probabilities for all the states based on PDFs.

In some embodiments, different probability functions may be determined for different time intervals. The peaks of the signal values may drift over time. Thus, different sets of probability functions may be used to determine the emission probabilities at different time steps.

E. Decoder—Determining Optimal Sequence of Hidden States

Once the states are defined and the transition probabilities and emission probability functions determined, the hidden states can be decoded to determine the bases that have been bound to the template nucleic acid. In some embodiments, the transition probabilities and emission probability functions may be fully determined across the entire sequencing run for a given cell before the hidden states are decoded.

Multiple decoders may be used with different observed parameters, e.g., one model using each of the signal values and another model using a single statistical (summary) value for a given bright period of an AC cycle. The use of the summary value may run faster, but use of individual ADC values can allow for more description in the states, e.g., more and various states as described above.

1. Observation Table

Using the PDFs and the measured signal values at each time step, an observation table can be generated. For each time step, the measured signal value can be used to determine a probability for each of the states (e.g., the enzyme states).

Figures 17A, 17B:
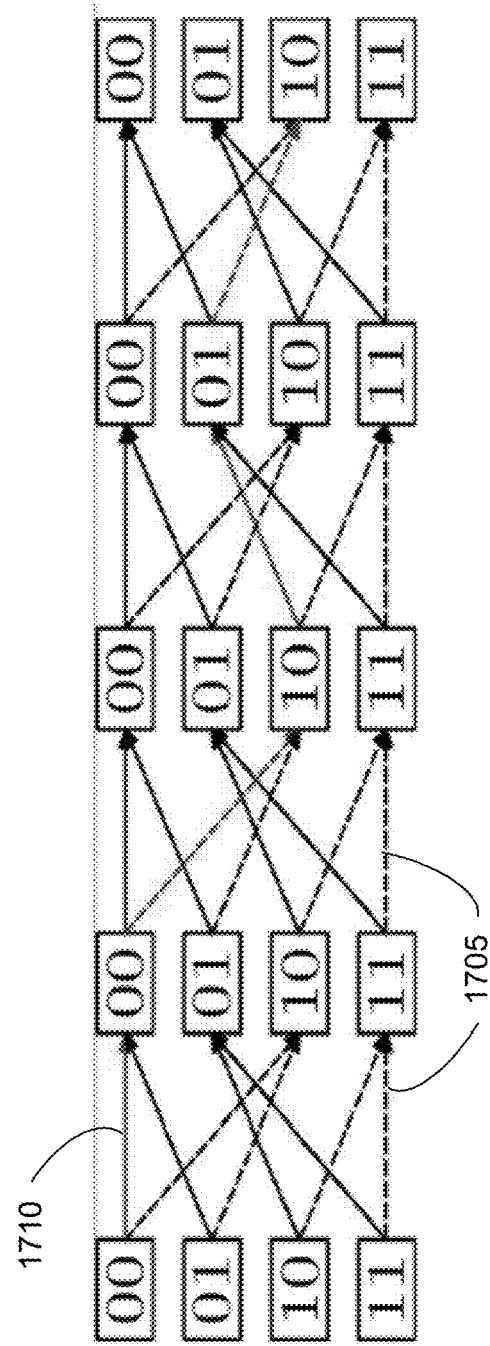
FIG. 17A shows an observation table for four states at five time steps according to embodiments of the present invention.
FIG. 17B show an example trellis diagram for four states and five time steps according to embodiments of the present invention.

FIG. 17A shows an observation table for four states at five time steps according to embodiments of the present invention. The four states are S1-S4, and the five time steps are T1-T5. More states and more time steps may be used. The values in the observation table correspond to the different probabilities for each state, as determined based on the measured signal value at each time step.

As an example, for observation one (i.e., time step T1), a signal value can be used to determine the corresponding probabilities (P11, P21, P31, and P41) for each state based on the respective PDFs. The same can be done for each measured signal value, each corresponding to a different time step. The number of time steps can be part of or all of the measurements for a given nucleic acid in a cell. For example, a certain segment of measurements can be decoded together as a chunk, and another segment of measurements for another part of the nucleic acid can be decoded as a different chunk.

In the example of FIG. 16, there is a one-one correspondence of a probability function to an enzyme state, as there is a one-one correspondence of a pore state to an enzyme state. In other implementations, there can be more pore states than enzyme states, e.g., pore states that involve unbound tags or a background structure. In this case, more than probability function can correspond to a given enzyme state. Thus, a probability for a given state at a given time step (e.g., P11) can be determined as a sum of probability values determined from multiple probability functions. For example, an unbound enzyme state could have contributions from probability functions corresponding to unbound tags threading through the pore. In other embodiments using system states that combine enzyme and pore states, states with unbound tags may be used but with the probability function corresponding to one system state.

In some embodiments, the observation table can be generated from an emission table, e.g., if discrete levels of the observed parameter is used. Once the observation table is generated, the continuous and the discrete HMMs can be processed the same way.

2. Optimal Path Through Trellis Diagram

The transition matrix and the observation table can be used to generate a trellis diagram (graph), where an optimal path through the trellis provides the binding events. The optimal path through the trellis diagram can be determined based on the Markov property, which is that the system is memoryless. At every point in time, only the previous column may be considered in determining the state that that time. The earlier columns may not be considered. In a trellis diagram, nucleotide states at one time step can be connected to nucleotide states at a next time step in accordance with the pairwise transition probabilities.

FIG. 17B show an example trellis diagram for four states and five time steps according to embodiments of the present invention. Each of the four states S1-S4 is shown represented by the binary value of numbers 1-4. The columns correspond to the time steps, as in the observation table. The red arrows correspond to the optimal path. By optimal, the path can have the highest probability for each transition from one time step to another. The first column in the trellis diagram can refer to the probabilities of the states at time=0 as $P(S_0)$ for specifying initial conditions. The probabilities $P(S_{t+1}|S_t)$ specifies the transition dynamics, e.g., as specified in the transition matrix in FIG. 14A. The probabilities P(Yt|St) specify the sensor model, e.g., as defined by the emission probability functions.

Each of the arrows 1705 has an associated value determined by combining the corresponding values from the observation table and the transition matrix. For example, a likelihood of transition 1710 can be determined based on the transition matrix element corresponding to (S1,S1) and the value of P12. Thus, assuming that the state is S1 (i.e., 00) at T1, the likelihood of transition 1710 can be determined based on the transition matrix element and the PDF probability. These likelihoods can be used by a decoder (e.g., a Viterbi decoder) to determine the optimal path.

As part of determining the trellis diagram, the likelihood that the system was in any of the states at every single point in time can be determined. The likelihoods may be dependent on whether a particular transition is allowed and or likely and on the actual measured signal value, which is used to provide the probabilities that the system was in a given state as determined in the observation table. In one embodiment, the likelihood of a transition can be determined by multiplying the corresponding value from the transition matrix and the corresponding value from the observation table. The calculation can be performed in log space.

The state at T1 can often be assumed to be a state 0 where nothing is bound. Then, as part of determining the optimal path to T2, it can be known that the transition from S0 to S1 is impossible or have a low probability. And, so then the next best guess may be the transition from S0 to S2, which is possible and can have a high transition rate. It may be that the observed probability of being in S1 at T2 is higher than being in state 2, but the difference in the transition probabilities can lead to selecting S2.

A forward pass through the trellis diagram may be performed to determine the likelihood that the system was in any given state at any point in time. One embodiment can take the maximum probability at every time point. Additionally, a trace back can be performed to determine if the same path is obtained, as part of a forward-backward algorithm. In determining the optimal path, some embodiments may only use the current state to determine the next state.

At each time step, the resulting states can correspond to the binding events when only binding states are used. When other states are used (e.g., partially bound states and unbound states), the trellis diagram can be searched to extract the bound states. In some embodiments, if multiple bound states exist between two unbound states, those bound states may be further analyzed to determine whether multiple bases actually exist or whether they correspond to an incorporation of a single nucleotide.

When non-bound states exist, further information can also be determined. For example, threading times can be determined. This may be done by analyzing instances where the state went from bound and unthreaded (e.g., an open channel state) to bound and threaded. By looking at the results on the trellis, a threading time for all of those instances can be determined. Or, only what is bound at a given time may be determined so as to determine the basecalls.

In some embodiments, the optimal path on the trellis can provide the pore data layer and the enzyme data layer (binding events) depending on which states are defined for the system. The different combinations of the layers and all the states that come from the different combinations can be called system states, i.e., a combination of the enzyme layer state and the pore layer state. The system states can describe all the combinations of those two layers, both of which can be read out of one trellis if defined in that way.

F. Determining Base Calls

In one embodiment to determine a base call, every binding event can be taken as a base call. Such a procedure may be accurate if the sequencing cell did not stutter, e.g., a nucleotide was incorporated but did not catalyze, with a new nucleotide of the same type being incorporated and catalyzed later. For example, assume that every time there was a binding event, it had a 50% chance of falling off before catalyzed. The list of binding events can be analyzed to reduce the number of base call. For instance, every time two or more consecutive binding events are for the same base, the number can be divided in half. Modifications may be made to account for sometimes being only one binding event in a row for a nucleotide, as opposed to two or more.

In some implementations, when deciding whether to merge two binding states (corresponding to a same base) adjacent in time but separated by an unbound state, it can be determined how likely that a threading event is missed when a nucleotide is bound the whole time. This can be balanced with how likely it is for two finding two binding states for a same state very close together in time. In operation of the sequencing cell, the waiting time between binding events can be designed to be sufficiently large by diluting the tagged nucleotides so that there is plenty of waiting time between binding events. However, the longer between binding events, then the slower the throughput is.

VI. Quality Score

In some embodiments, a quality score of a base can be provided. The quality score can be reflective of the stochastic behavior that is inherent to single molecule observations. The quality of basecalls may not degrade with time or with read length, but there can be different quality scores for different basecalls randomly at different points in time on a given template nucleic acid. A higher quality score for a basecall can indicate greater confidence in the basecall being correct. For example, a signal value that is near a peak of a PDF can result in a basecall having a higher quality score than a signal value that is far from a peak of a PDF. One of the outputs of a basecaller (e.g., using an HMM) can be such a quality score.

In some embodiments, a quality score can be computed as follows.

$$Q = -10 \times \log_{10}(P_{error}),$$

$$P_{error} = 1 - P(state_{decoded} | obs),$$

$$P(state_i | obs) = \frac{P(obs | state_i) \times P(state_i)}{P(obs)},$$

$$P(obs) = \sum_i P(obs | state_i) \times P(state_i).$$

$P(obs|state_i)$ can be determined from the probability functions, and
$P(state_i)$ can be determined from the transition probabilities.

The quality score Q provides a measure for how likely an enzyme state was correctly called between the four bases, and potentially for the unbound state when applicable. The Q values can be specified to be within a particular range, e.g., with higher Q values providing greater confidence in accuracy. In some aspects, a component of the Q score can include the confidence in merging biding or pore events of a same signal level, e.g., arising from an AC mode splitting one binding event into smaller pulses.

As an example of determining a quality score using an HMM, different sub-optimal paths through the hidden space (e.g., the trellis diagram). The relative probabilities can be weighted to give an informative sense of the quality, i.e., how sure is the base call.

For example, the decoder can identify a series of threading signals of tag having similar values over a plurality of cycles as corresponding to a single bound nucleotide. When the Q scores are generated, the other sub-optimal paths can be considered to determine whether the measured signal values could still be produced, and if it did what is the probability of that combined path and the measured signal values. The probability can be computed for all of the hidden states for that given set of observations. The quality score can provide a relative separation between the possible states. If the probability of another state was just slightly less, then the quality score would be relatively low.

In some embodiments, information from a normalization procedure can be used in determining the quality score. For example, an estimate of uncertainty can be obtained from a Kalman filter that is used to estimate the current open channel voltage used to determine an OC fraction. The uncertainty can be used to adjust the Q score. The uncertainty can be viewed as how well did the normalization work.

VII. Updating Emission PDFS (Time-Dependent Mixture Model)

As mentioned above, initial values for the parameters for the mixture model (or other PDFs) can be determined based on measurements from other sequencing cells using similar pores and tags. The PDFs can be updated based on recent measurements and can be determined on a per pore basis. The PDFs for some states can be very stable from one experiment to another. Such states can be characterized, and the shape of the emission function determined. Other states can change over time and/or be different from one pore to another.

Accordingly, embodiments can determine initial parameters for the PDFs, e.g., a location for the peak, width of each PDF, and the rate of exponential decay of each PDF. Then, a set of signal values can be measured and used to determine a histogram, which can be used to update the parameters of the PDFs. Updating the PDFs in real-time based on the actual measurements is helpful, as it allows tuning the basecalling procedure on a per sensor (e.g., pore) basis. Thus, the probability functions can be adjusted over the time for the sequencing of a nucleic acid in a given cell.

In some embodiments, the PDFs can be updated using Bayesian statistics. The initial PDFs can be treated as prior distributions, and the updated PDFs can be determined as the posterior distributions using the measured signal values for a given pore. In some implementations, a first set of measured signal values are only a portion of the signal values measured for a nucleic acid in a given run for a cell. Later sets of signal values can be used to update the PDFs over the sequencing time for later portions of the nucleic acid. In this manner, time-dependent PDFs (e.g., a time-dependent mixture model) can be obtained.

In determining the posterior distribution, an initial basecall can be determined using prior distribution (e.g., using an HMM, cutoff values separating the expected clusters, or the base with the highest probability from the prior distributions). The basecalls for a particular base can be used to determine the posterior distribution corresponding to that base using the prior distribution of that base, as opposed to determining all or multiple posterior distributions at the same time. In some implementations, only the signal values that clearly correspond to a particular base (e.g., have an emission probability higher than a threshold, which may be relative to a second highest probability of another base) are used to determine the posterior probability for a given time period. The signal values may be selected based on quality scores of the basecalls corresponding to the signal values. In addition or alternatively, only certain signal values (e.g., for basecalls having a quality score above a threshold) are used to determine the prior distributions.

In other embodiments, updating the PDFs can just use a first set of measurements for a given cell, but have the initial values for the optimization procedure start at the values obtained from other sequencing cells and/or sequencing chips. Such constraints can be added to the optimization procedure so that the new parameters do not deviate too significantly from the initial values. Besides individual values for the parameters not changing significantly from the initial values, constraints can be imposed on relative values of the parameters (e.g., a distance between location of two peaks of the PDFs can be constrained to be within a specified range). In such a situation, updating the PDFs can be a shift of the location of a set of peaks up or down in value. If the new measurements do cause the parameters of the PDFs to change significantly (or reach the constraints), there may be problems with a given sequencing cell. For example, the peak locations of two PDFs can become too close. Such a problem can result in discarding the data for that cell.

In addition or instead of using initial parameter values from other cells and/or chips, an initial set of signal values can be used to determine an initial histogram, which is used to determine the PDFs. For example, a third of the signal values for a sequencing run of a cell can be used to determine parameter values for the PDFs.

A. Method for Determining Time-Dependent PDFs

Figure 18:
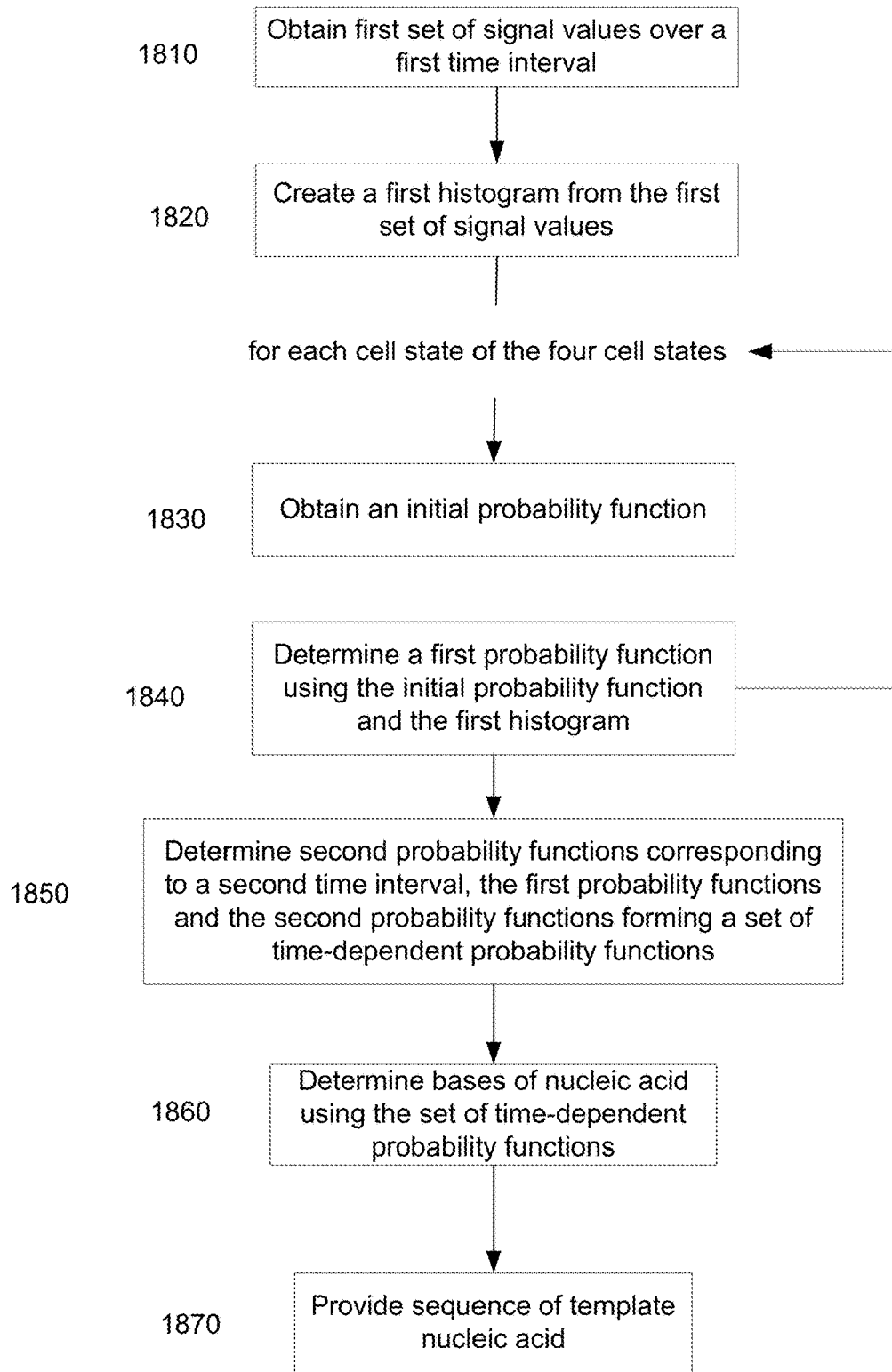
FIG. 18 is a flowchart of a method of using a sequencing cell to determine time-dependent probability functions for sequencing a nucleic acid according to embodiments of the present invention.

FIG. 18 is a flowchart of a method 1800 of using a sequencing cell to determine time-dependent probability functions for sequencing a nucleic acid according to embodiments of the present invention. Aspects of method 1800 can be performed in a similar manner as method 1000.

At block 1810, a first set of signal values measured from a nucleic acid over a first time interval for a sequencing cell is obtained. The first set of signal values can include measurements for each of four cell states (e.g., pore states) of the sequencing cell, where the four cell states correspond to different types of nucleotides. In some implementations (e.g., involving a polymerase), five cell states can be used, e.g., with a fifth cell state corresponding to no nucleotide currently in the active site. The signal values carry measured in a cell a manner as described for block 1030 of FIG. 10.

The first set of signal values can be obtained by receiving the signal values at a processor, e.g., processor 224 of FIG. 2 the received signal values from electric circuit 222. In some implementations, the obtaining can include the measurement of the signal values using the sequencing cell. The first set of signal values can be normalized, e.g., as described in block 1040 of FIG. 10.

At block 1820, a first histogram is created from the first set of signal values. Block 1820 can be implemented in a similar manner as block 1050 of FIG. 10. For example, the first histogram can be a data structure storing a plurality of counts, each count corresponding to a number of signal values within a bin of the histogram. Each bin of the first histogram can correspond to different numerical values, e.g., as described with respect to FIG. 11.

Blocks 1830 and 1840 can be performed for each cell state of the four cell states. When more cell states are used, blocks 1830 in 1840 can be performed for those cell states as well.

At block 1830, an initial probability function that assigns emission probabilities of being in the cell state to the different numerical values is obtained. Examples of the initial probability function are described above. For example, the initial probability function can be determined using signal values measured from one or more other sequencing cells. For instance, the signal values from the other cells can be used to create a histogram to which the initial probability function can be fit (potentially all of the initial probability functions being determined together). As another example, the initial probability function can be determined using signal values measured from an earlier time interval than the first time interval.

As yet another example, the initial probability function can be determined using signal values measured over a larger time interval that includes the first time interval and other time intervals in sequencing the nucleic acid. For instance, larger time interval can be across the entire sequencing run for that cell. The signal values used from the larger time interval may include only certain signal values, e.g., signal values that are in a tight cluster, as may be defined by a threshold signal distance from a centroid. A first pass with a basecaller (e.g., an HMM or a just using cutoff values) over all signal values in the larger time interval can provide initial basecalls along with quality scores, for signal values corresponding to the basecalls with high quality scores can be selected for determining the initial probability function for a given cell state (e.g., a pore state corresponding to a particular threaded tag). In this manner, the initial probability function can have a narrower width with a more accurate location of a peak, as it corresponds to signal values that are highly indicative of the binding state of a particular nucleotide.

At block 1840, the initial probability function and the first histogram are used to determine a first probability function corresponding to the first time interval. The first probability function assigns emission probabilities of being in the cell state to different numerical values. Example techniques for determining the first probably function are provided above. For instance, a Bayesian procedure can use the initial probability function as a prior distribution, with the first histogram being new measurements that provide the first probability function as a posterior distribution.

At block 1850, second probability functions corresponding to a second time interval are determined. The second probability functions would correspond to the four cell states. The first probability functions and the second probability functions (potentially along with other probability functions for other time intervals) can form a set of time-dependent probability functions. This set of time-dependent probability functions can provide increased accuracy in creating an observation table as part of an HMM basecalling procedure.

The time intervals can be of various lengths, e.g., each one AC cycle long, or many AC cycles long. The different time intervals can correspond to chunks of time (or data) and may be hundred(s) of seconds long, but may be larger or smaller. If smaller chunks are used, the time-dependent probability functions can be updated more often, but then the prior distribution can be given more weight such that the amount of adjustment per update is less than when larger chunks are used. The variability in the probability distributions over time can be relatively slow, e.g., over the course of an hour they may drift 10%, 15%, or 30%. The change is gradual so it is possible to have the probability functions update without losing a tracking of the correspondence of a probability function and a particular cell state.

The second probability function can be determined using the first probability functions and a second histogram, which is determined from a second set of signal values measured from the nucleic acid over the second time interval for the sequencing cell. The second probability functions can be determined in a similar manner as the first probability functions, but with the first probability functions now acting as the initial probability functions.

At block 1860, the bases comprising a sequence of the nucleic acid are determined using the set of time-dependent probability functions. The bases can be determined in a variety of ways, e.g., taking the base corresponding to the cell state with the highest probability for a given time step as the base call. In another embodiment, an HMM might be used, and thus block 1070 of FIG. 10 may be used. Aspects of block 1080 may also be used.

At block 1870, the sequence of the nucleic acid is provided. Block 1870 can be performed in a similar manner as block 1090.

B. 2-Passes with HMM

As mentioned above, the initial probability functions can be determined using signal values across a sequencing run. These initial probability functions can be determined as time-independent PDFs. A basecaller (e.g., using an HMM) can be performed to determine initial basecalls, e.g., in a similar manner as described in embodiments of method 1000. Such a first pass of a basecaller using the time-independent PDFs can identify clean signal values that are highly indicative (e.g., higher probabilities and/or quality scores for related basecalls) of a particular tag/base. These high-quality signal values can be used for determining updates to the time-dependent PDFs, thereby reducing noise from the determination of the time-dependent PDFs.

The basecaller can then use the time-dependent PDFs in a second pass over the time steps. A new observation table can be created, resulting in a new trellis diagram. Implementing such a two-pass method can increase the accuracy of marginal basecalls. The improvement can occur due to the increased accuracy of the time-dependent PDFs over the time independent PDFs. Such an improvement can also occurred as specific functional signal values for a given time step can be attributed a particular tag/base. Thus, the fitting of the PDFs to a histogram for a given time interval can be more accurate since many signal values can be attributed to a particular cell state (e.g., a pore state), and thus to a particular PDF.

Accordingly, in some embodiments, an initial sequence of initial basecalls of the nucleic acid can be determined using the initial probability function. A quality score can be determined for each of the initial basecalls. The first set of signal values can be selected from all signal values within the first time interval based on the quality score of corresponding initial basecalls. A basecall for a binding state can correspond to a signal value based on the binding state covering a time period that includes the signal value.

C. Probability Functions for Unbound Tags

The emission PDFs of additional pore states can be varied, e.g., when unbound tags are represented with respective PDFs. For example, a PDF for an unbound G tag can have a shape that is peaked at a different location than the bound G PDF. For a partial integration state, the PDF can have a more uniform distribution from the open channel down to the peak, as the tag is going from an unthreaded state to a threaded state. Thus, a partial integration state can have a separate PDF that would be a link between two states, e.g., open channel and A.

Such additional states (e.g., defined as system states) can allow for time-dependent transitions, whereas including more pore states into a single PDF (e.g., all unbound states represented as a single PDF as opposed to separate PDFs) the less that it known about time-dependent aspects, such as how long the partial integrations states last and what order the partial states are in relative to other states. Accordingly, it is possible to put unbound and/or partial state information into separate PDF, but with an increase in computational effort due to the increased number of states.

VIII. Initial Classification Using 2-State Classifier

In embodiments using a polymerase, the polymerase can be a bound state with one of the four nucleotides or in an unbound state with no nucleotide in the active site. Instead of classifying all five binding states with the same procedure (e.g., as described herein), some embodiments can use an initial classifier to classify measured signal values as corresponding to a bound state or an unbound state. Such a 2-state classifier can be an HMM with two hidden states, but other 2-state classifiers may also be used.

Then, the time steps that correspond to a bound state can be analyzed further using a 4-state classifier. The 4-state classifier can operate more efficiently due to fewer states to discriminate between, resulting in a lower memory requirements and faster computational speed. Increased accuracy can also be obtained from more accurate PDFs, when only signal values in the bound regions identified by the 2-state classifier are used.

The initial 2-state classifier can identify time steps that correspond to a bound state. The 2-state classifier does not need to distinguish which type of binding state corresponds to the bound state (e.g., which tag is in a pore), just that one binding state exists. After the initial 2-state classifier identifies the signal values corresponding to a bound state, the signal values can be used to determine four PDFs: one for each nucleotide. The PDFs can be determined via fitting a mixture model to a histogram of the signal values corresponding to the bound states.

A. First Classifier (2-State Classifier)

The first classifier can operate on normalized or non-normalized signal values. In an embodiment using tags and a pore, the 2-state classifier can determine whether a signal value corresponds to an open channel state or a threaded state, where a tag is in the pore. As an example for the normalized signal values (e.g., OC fraction), a peak for the unbound state can be around 1.0, and any values sufficiently below 1.0 (e.g., below 0.9) corresponds to a bound state.

In a more sophisticated version of this 2-state classifier, there can be two PDFs: one for the bound state and one for the unbound state, which can be viewed as being equivalent to a threaded state and an unthreaded state. The 2-state classifier can be considered to classify between pore states, in embodiments using a pore. The PDFs can be used in conjunction with an HMM to determine which state corresponds to which time step.

The unbound state can include various sub-states, e.g., corresponding to a background, a noise band, or free tags. Even if a free tag results in a brief change in the signal value for one time step before it returns to an open channel value, the 2-state classifier can determine that an unbound state still exists due to the transitory nature of the one signal value. Thus, the 2-state classifier (decoder) can look at how long an open channel signal persists in determining an unbound state, and can look at how long a threaded signal persists in determining a bound state. For an HMM implementation, a transition matrix can contain information about how a binding event should be.

As an example, the observation table can be represented as a vector of 0's or 1's, with a zero corresponding to one state and the one corresponding to the other state. The 0 can be viewed as a 0% probability and the 1 as 100% probability; other probability values can also be used. Where 1 corresponds to a bound state, the vector can be analyzed to determine whether a sufficiently long group of 1's exist, so as to recognize a bound state. Even if there were sporadic 0's, a bound state can still be recognized. Similarly, when a few 1's sporadically appearing in a group of 0's, the series of time steps can be identified as corresponding to an unbound state.

The 2-state classifier can be viewed as a differential filter, which analyzes a signal value relative to other signal values that are close in time. Such a differential filter can help to filter out data that is most likely background prior to building up the emission PDFs.

B. Method Using Two Classifiers

Figure 19:
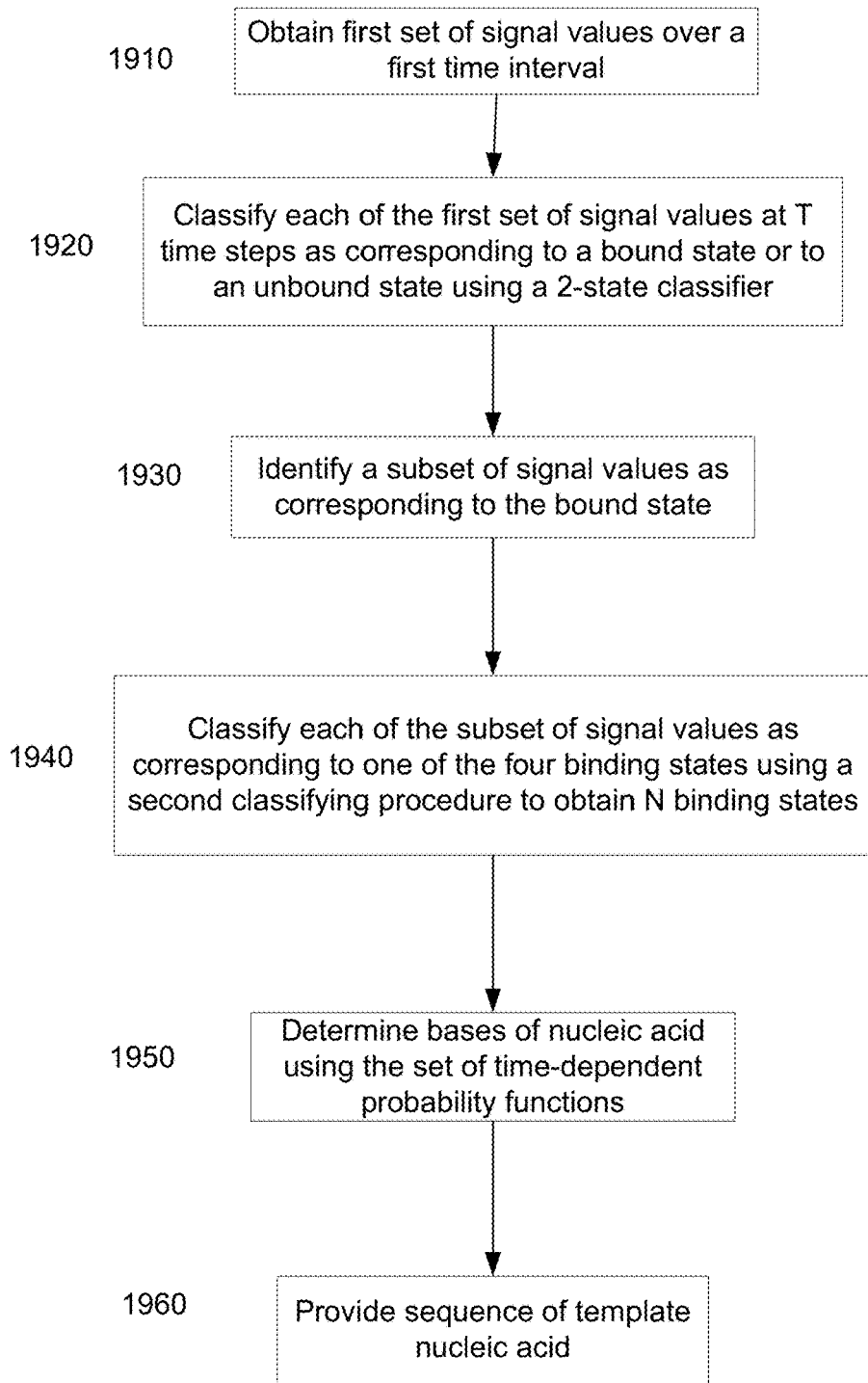
FIG. 19 is a flowchart of a method of using a sequencing cell to sequence a nucleic acid using a 2-state classifier and a second classifier according to embodiments of the present invention.

FIG. 19 is a flowchart of a method 1900 of using a sequencing cell to sequence a nucleic acid using a 2-state classifier and a second classifier according to embodiments of the present invention. Aspects of method 1900 can be performed in a similar manner as method 1000 and/or method 1800.

At block 1910, a first set of signal values is obtained. These signal values are measured from a nucleic acid over a first time interval for a sequencing cell that includes a polymerase. The first set of signal values can include measurements for each of five binding states of the sequencing cell. Four binding states can correspond to different types of nucleotides and a fifth binding state can corresponds to no nucleotide being in an active site of the polymerase. The four binding states can collectively correspond to a bound state and the fifth binding state can be an unbound state. Block 1910 can be performed in a similar manner as block 1810.

At block 1920, each of the first set of signal values at T time steps is classified as corresponding to the bound state or to the unbound state using a first classifying procedure. The first classifying procedure can be a 2-state classifier. The 2-state classifier can operate as described herein.

At block 1930, a subset of signal values is identified as corresponding to the bound state. The subset may correspond to disjoint regions that are identified as corresponding to bound states. In some implementations, all the signal values within a region identified as corresponding to a bound state can be included in the subset. Such disjoint regions can be analyzed independently (e.g., in parallel) in later stages of method 1900 or analyzed collectively. In one embodiment, the subset of signal values can be used to determine a histogram for the bound regions, where the histogram can be used to determine respective PDFs for different tags/nucleotides.

At block 1940, each of the subset of signal values is classified as corresponding to one of the four binding states using a second classifying procedure to obtain N binding states. The second classifying procedure can classify between at least the 4 binding states. In some embodiments, the second classifying procedure can classify among more binding states (e.g., including partial threaded states). The second classifying procedure may also include a non-binding state, e.g., to confirm that no unbound state exists within the identified bound regions.

The second classifier can operate in regions identified as corresponding to bound states. Focusing on only such regions can improve the estimates for the PDFs, e.g., as a histogram may not include any signal values corresponding to unbound states. A mixture model can be more accurately fit to this more specific data. Accordingly, in some embodiments, one or more additional trellis diagrams can be created, each corresponding to a separate bound region of one or more time steps having the bound state. Then, one or more additional optimal paths through the trellis diagram can be determined based on the emission probabilities and the pairwise transition probabilities.

At block 1950, bases comprising a sequence of the nucleic acid are determined using the N binding states. Block 1950 can be implemented in a similar manner as block 1860 of method 1800.

At block 1960, the sequence of the nucleic acid is provided. Block 1960 can be implemented in a similar manner as block 1870 of method 1800.

IX. Examples and List Decoder

Figure 20:
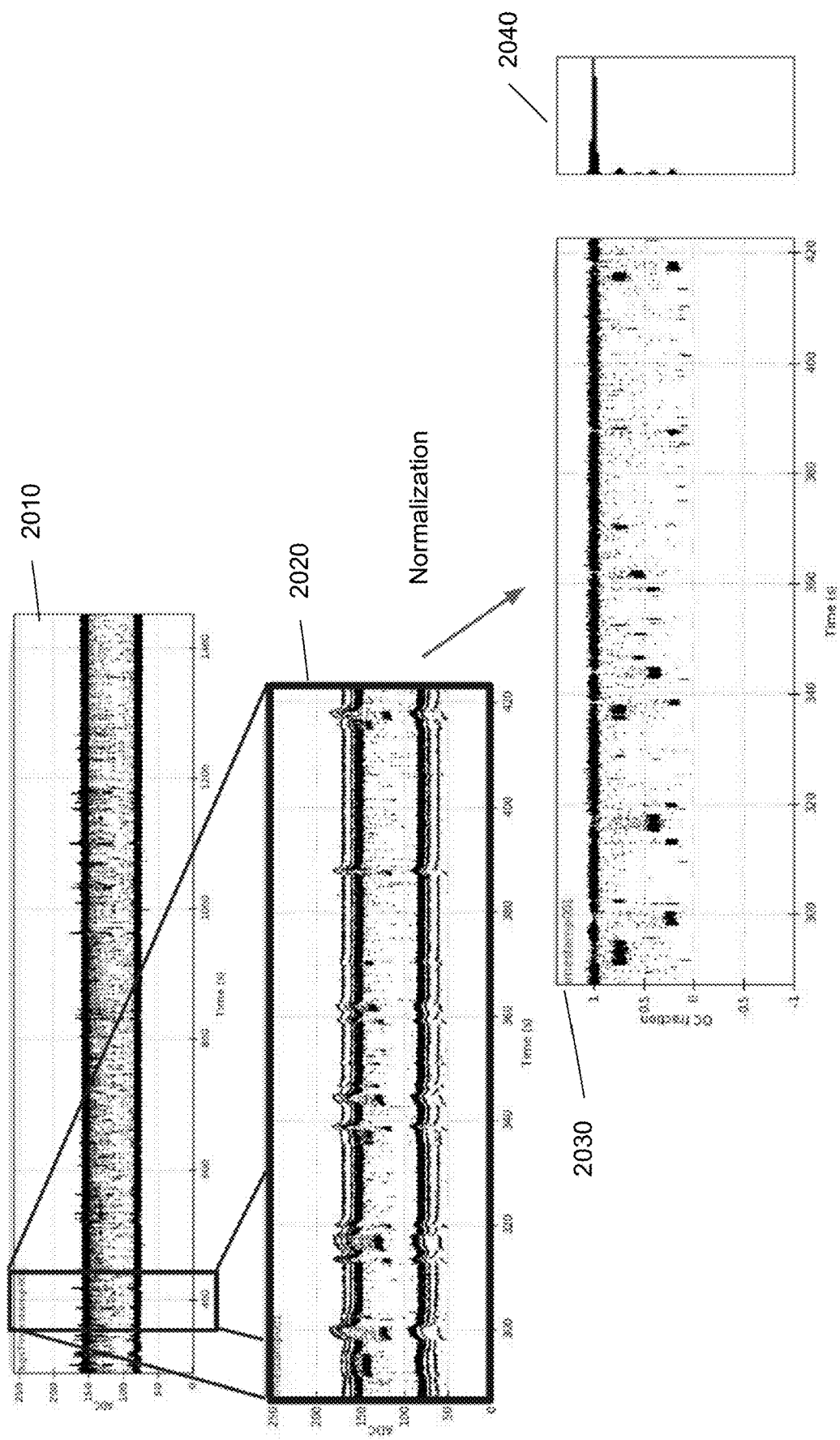
FIG. 20 shows an example of a signal trace, a magnified trace, normalized signal values, and a histogram according to embodiments of the present invention.

FIG. 20 shows an example of a signal trace 2010, a magnified trace 2020, normalized signal values 2030, and a histogram 2040 according to embodiments of the present invention. In this example for signal trace 2010, the HMM decoder identifies the sequence of most likely binding states to be: ATAGCTAGCACAGAGAGCGACAGCATAC-TACTCACTGACGCAGAGCG (SEQ ID NO:4). The magnified trace 2020 shows two dark bands for the open channel and dark channel. The normalized signal values 2030 (dark channel removed) shows flatter data than magnified trace 2020, as a result of the normalization. Histogram 2040 corresponds to a set of signal values in the time interval represented in the plot of normalized signal values 2030.

Figure 21:
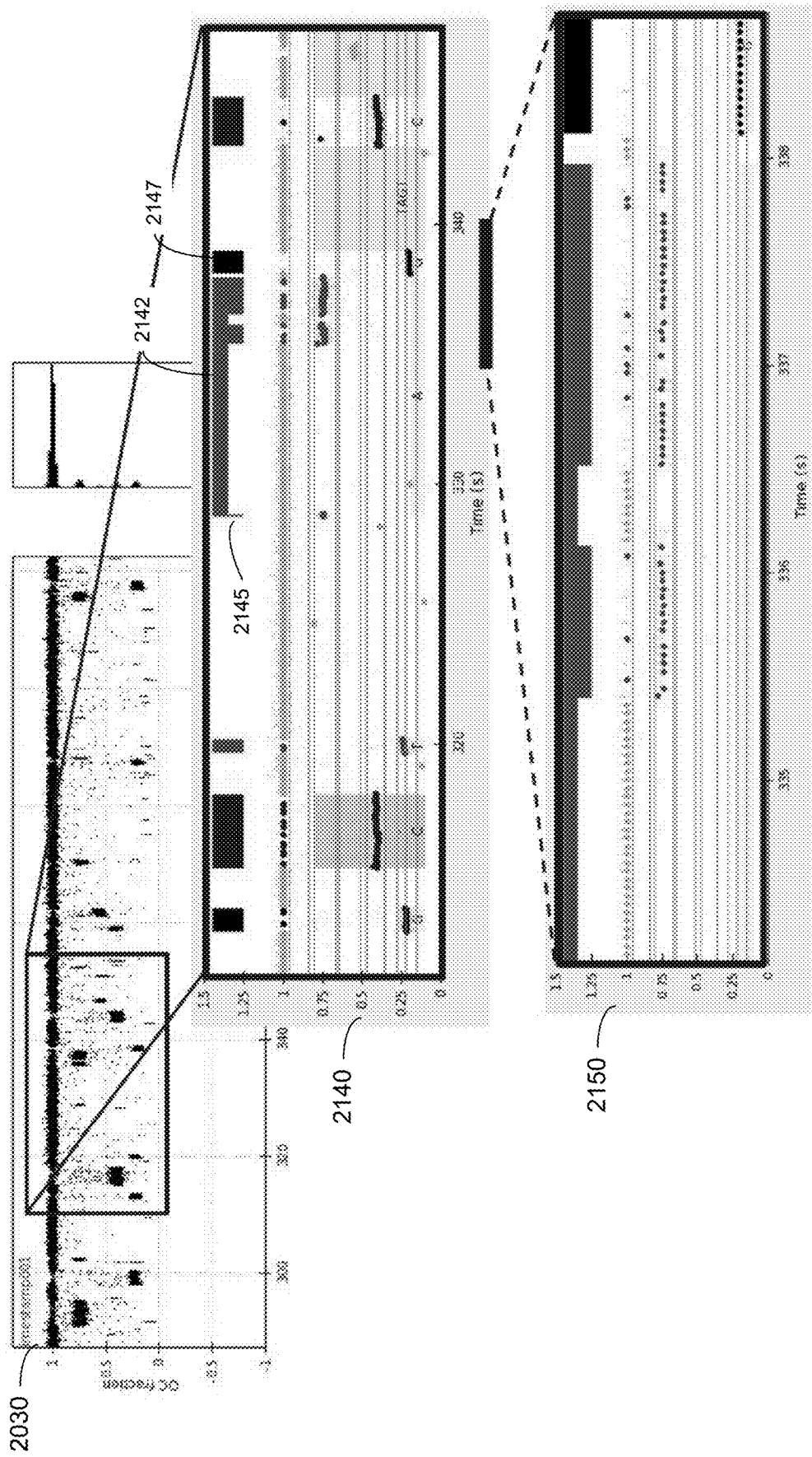
FIG. 21 shows normalized signal values, an intermediate view, and a highest zoom view according to embodiments of the present invention.

FIG. 21 shows normalized signal values 2030, an intermediate view 2140, and a high zoom view 2150 according to embodiments of the present invention. Intermediate view 2140 shows a zoom level to see individual events. The bars indicate the individual binding events, potentially indicating areas where there may be more than one binding event of a particular type. For example, bar 2142 indicates that decoder identifies one binding state for A, but there are three smaller bars indicating that there may actually be three binding states for A. A gap between bar 2145 in the next bar indicates that there were no threaded pore states in between. Bar 2147 indicates that after a time where nothing was bound, a G binding event is detected. The high zoom view 2150 shows the last two A binding events, and the G binding event.

Figure 22:
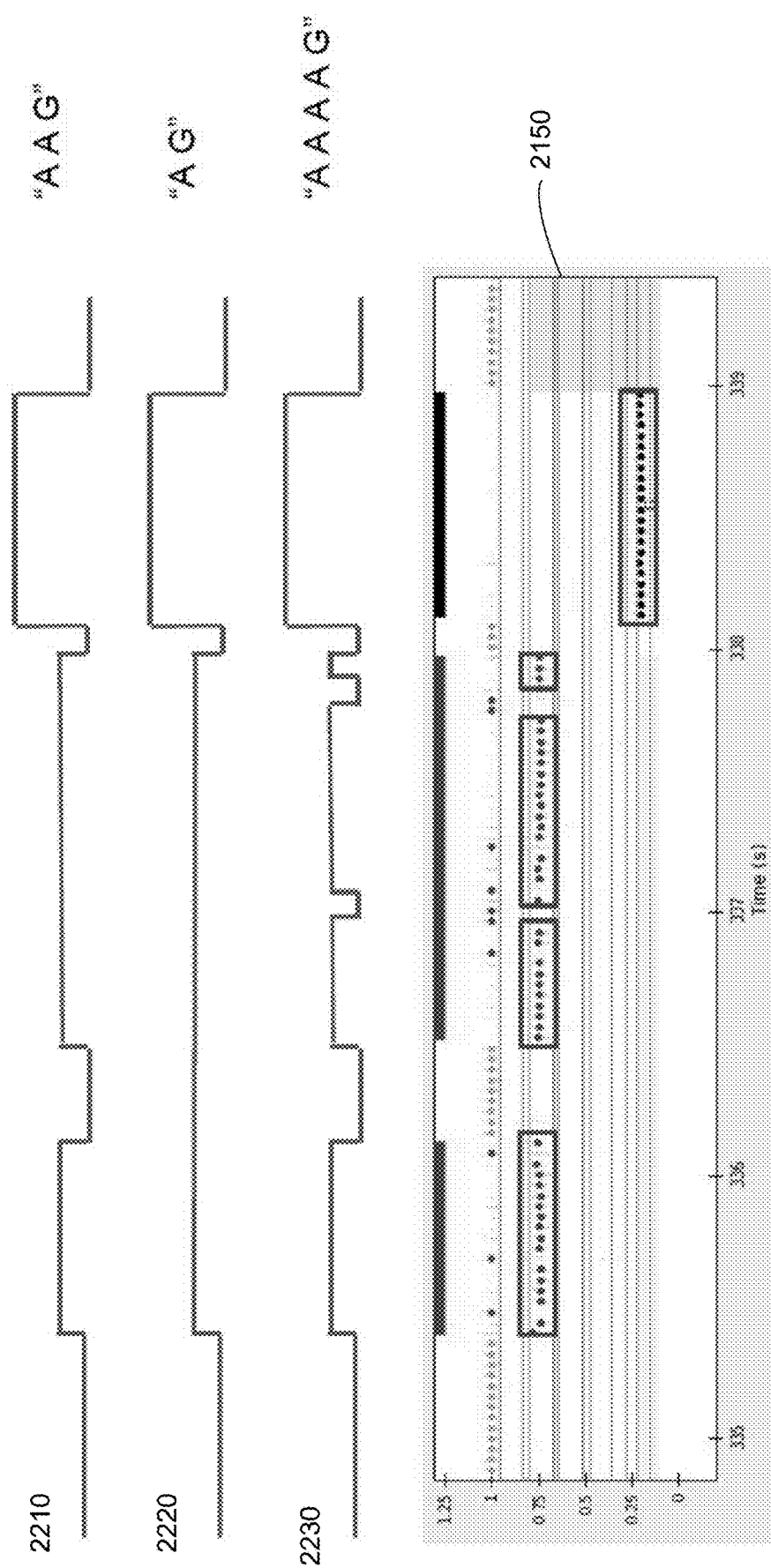
FIG. 22 shows the high zoom view and the top three most likely hidden states according to embodiments of the present invention.

FIG. 22 shows the high zoom view 2150 and the top three most likely hidden states 2210-2230 according to embodiments of the present invention. As can be seen by the three top states, it may not be clear how many A binding events occurred. In some embodiments, the probability for each of these sequences can be determined, e.g., using a list decoder, which is a modified version of Viterbi that determines not only the most likely call, but additional sub-optimal calls. For example, the K most likely hidden states can be determined. Such probability of different sequences can be passed downstream to later stages of genomic analysis.

X. Computer System

Figure 23:
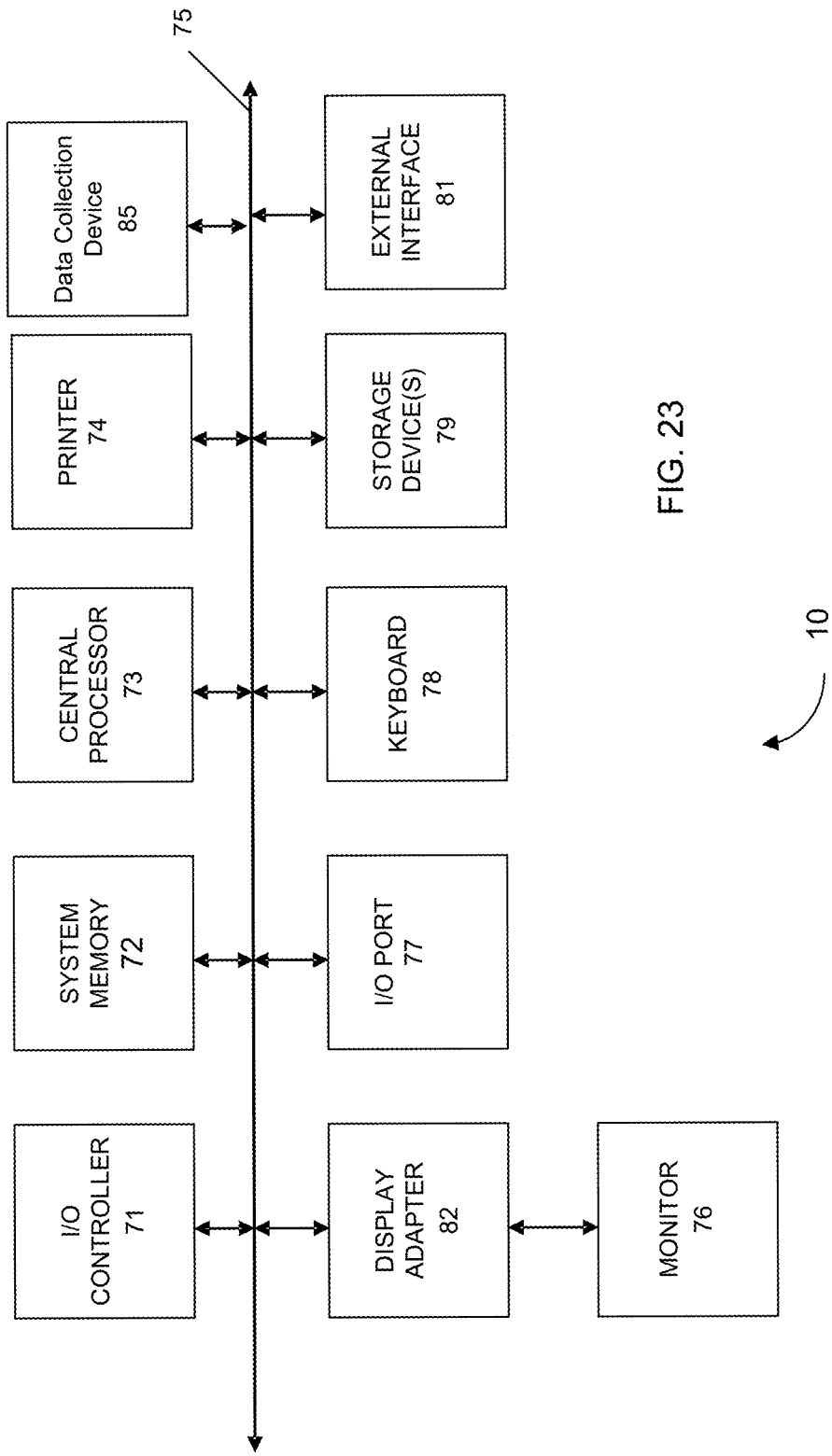
FIG. 23 shows a block diagram of an example computer system usable with system and methods according to embodiments of the present invention.

Any of the computer systems mentioned herein may utilize any suitable number of subsystems. Examples of such subsystems are shown in FIG. 23 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 23 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81, by an internal interface, or via removable storage devices that can be connected and removed from one component to another component. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware circuitry (e.g. an application specific integrated circuit or field programmable gate array) and/or using computer software with a generally programmable processor in a modular or integrated manner. As used herein, a processor can include a single-core processor, multi-core processor on a same integrated chip, or multiple processing units on a single circuit board or networked, as well as dedicated hardware. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective step or a respective group of steps. Although presented as numbered steps, steps of methods herein can be performed at a same time or at different times or in a different order. Additionally, portions of these steps may be used with portions of other steps from other methods. Also, all or portions of a step may be optional. Additionally, any of the steps of any of the methods can be performed with modules, units, circuits, or other means of a system for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover reference to a "first" or a "second" component does not limit the referenced component to a particular location unless expressly stated. The term "based on" is intended to mean "based at least in part on."

All patents, patent applications, publications, and descriptions mentioned herein are incorporated by reference in their entirety for all purposes. None is admitted to be prior art.

What is claimed is:

1. A method of using a sequencing cell, the method comprising:
obtaining a first set of signal values measured from a nucleic acid over a first time interval for the sequencing cell that includes a polymerase, wherein the first set of signal values includes measurements for each of five states of the sequencing cell, wherein the five states include four binding states corresponding to different types of nucleotides and a non-binding state corresponding to no nucleotide being in an active site of the polymerase, wherein the four binding states collectively correspond to a bound state and the non-binding state is an unbound state;
classifying each of the first set of signal values at T time steps as corresponding to either the bound state or to the unbound state using a first classifying procedure;
identifying a subset of signal values as corresponding to the bound state;
classifying each of the subset of signal values as corresponding to one of the four binding states using a second classifying procedure to obtain N classified states, wherein the second classifying procedure classifies between at least the four binding states;
determining bases comprising a sequence of the nucleic acid using the N classified states; and
providing the sequence of the nucleic acid.

2. The method of claim 1, wherein using the first classifying procedure includes:
creating a histogram of the first set of signal values, the histogram being a data structure storing a plurality of counts, each count corresponding to a number of signal values within a bin, each bin of the histogram corresponding to different numerical values;
for each state of the bound state and the unbound state:
determining a probability function that assigns emission probabilities of being in the state to the different numerical values, the probability function determined using the plurality of counts for the bins of the histogram;
determining transition probabilities between the unbound state and the bound state;
creating a trellis diagrams over the T time steps, wherein the trellis diagram at a given time step includes the bound state and the unbound state, and wherein states at one time step are connected to states at a next time step in accordance with the transition probabilities; and
determining an optimal path through the trellis diagram based on the emission probabilities and the transition probabilities to identify the bound state or the unbound state as existing at each time step.

3. The method of claim 1, wherein the second classifying procedure classifies each of the subset of signal values into one of the four binding states.

4. The method of claim 1, wherein using the second classifying procedure includes
creating a histogram of the subset of signal values, the histogram being a data structure storing a plurality of counts, each count corresponding to a number of signal values within a bin, each bin of the histogram corresponding to different numerical values;
for each binding state of the four binding states:
determining a probability function that assigns emission probabilities of being in the binding state to the different numerical values, the probability function determined using the plurality of counts for the bins of the histogram;
determining a transmission matrix providing pairwise transition probabilities between the four binding states of the nucleic acid;
creating a trellis diagram over a plurality of time steps, each time step corresponding to one signal value of the subset of signal values, wherein the trellis diagram at a given time step includes the four binding states, and wherein binding states at one time step are connected to binding states at a next time step in accordance with the pairwise transition probabilities;
determining an optimal path through the trellis diagram based on the emission probabilities and the pairwise transition probabilities to identify a binding state at each of the plurality of time steps;
creating one or more additional trellis diagrams, each corresponding to a separate bound region of one or more time steps having the bound state; and
determining one or more additional optimal paths through the trellis diagram based on the emission probabilities and the pairwise transition probabilities.

5. The method of claim 1, wherein the sequencing cell further includes a nanopore and has a voltage applied across the sequencing cell, and wherein the four binding states correspond to pore states of the nanopore.

6. The method of claim 5, wherein the voltage includes an alternating signal having a first portion and a second portion relative to a reference voltage, and wherein the first set of signal values is measured during the first portion of the alternating signal.

7. The method of claim 1, wherein the sequencing cell includes the polymerase attached to a nanopore for sequencing the nucleic acid, and wherein obtaining the first set of signal values includes:
applying a voltage across the sequencing cell, wherein the voltage includes an alternating signal having a first portion and a second portion relative to a reference voltage,
wherein at least a portion of the first set of signal values are measured during the first portion of the alternating signal when a tag molecule is threaded in the nanopore of the sequencing cell, the tag molecule corresponding to a particular nucleotide.

8. The method of claim 1, wherein using the first classifying procedure includes:
normalizing the first set of signal values to obtain normalized signal values; and
comparing normalized signal values to a threshold.

9. The method of claim 1, wherein the subset of signal values is a first subset of signal values, and wherein using the first classifying procedure includes:
identifying a second subset of signal values as corresponding to the unbound state;
creating a histogram of the second subset of signal values, the histogram being a data structure storing a plurality of counts, each count corresponding to a number of signal values within a bin, each bin of the histogram corresponding to different numerical values;
for each of a plurality of unbound sub-states:
determining a probability function that assigns emission probabilities of being in the unbound sub-state to the different numerical values, the probability function determined using the plurality of counts for the bins of the histogram, the plurality of unbound sub-states including the non-binding state;
determining a transmission matrix providing pairwise transition probabilities between the plurality of unbound sub-states;
creating a trellis diagram over a plurality of time steps, each time step corresponding to one signal value of the subset of signal values, wherein the trellis diagram at a given time step includes the plurality of unbound sub-states, and wherein unbound sub-states at one time step are connected to unbound sub-states at a next time step in accordance with the pairwise transition probabilities; and
determining an optimal path through the trellis diagram based on the emission probabilities and the pairwise transition probabilities to identify an unbound sub-state at each of the plurality of time steps.

10. The method of claim 9, wherein the plurality of unbound sub-states include background, a noise band, and free tags.

11. The method of claim 1, wherein the subset of signal values correspond to disjoint regions that are identified as corresponding to bound states.

12. A system comprising:
a sequencing chip including an array of sequencing cells, each including a polymerase; and
a computer system communicably coupled with the sequencing chip, the computer system configured to perform:
obtaining, from the sequencing chip, a first set of signal values measured from a nucleic acid over a first time interval for a sequencing cell, wherein the first set of signal values includes measurements for each of five states of the sequencing cell, wherein the five states include four binding states corresponding to different types of nucleotides and a non-binding state corresponding to no nucleotide being in an active site of the polymerase, wherein the four binding states collectively correspond to a bound state and the non-binding state is an unbound state;
classifying each of the first set of signal values at T time steps as corresponding to either the bound state or to the unbound state using a first classifying procedure;
identifying a subset of signal values as corresponding to the bound state;
classifying each of the subset of signal values as corresponding to one of the four binding states using a second classifying procedure to obtain N classified states, wherein the second classifying procedure classifies between at least the four binding states;
determining bases comprising a sequence of the nucleic acid using the N classified states; and
providing the sequence of the nucleic acid.

13. The system of claim 12, wherein using the first classifying procedure includes:
creating a histogram of the first set of signal values, the histogram being a data structure storing a plurality of counts, each count corresponding to a number of signal values within a bin, each bin of the histogram corresponding to different numerical values;
for each state of the bound state and the unbound state:
determining a probability function that assigns emission probabilities of being in the state to the different numerical values, the probability function determined using the plurality of counts for the bins of the histogram;
determining transition probabilities between the unbound state and the bound state;
creating a trellis diagrams over the T time steps, wherein the trellis diagram at a given time step includes the bound state and the unbound state, and wherein states at one time step are connected to states at a next time step in accordance with the transition probabilities; and
determining an optimal path through the trellis diagram based on the emission probabilities and the transition probabilities to identify the bound state or the unbound state as existing at each time step.

14. The system of claim 12, wherein using the second classifying procedure includes
creating a histogram of the subset of signal values, the histogram being a data structure storing a plurality of counts, each count corresponding to a number of signal values within a bin, each bin of the histogram corresponding to different numerical values;
for each binding state of the four binding states:
determining a probability function that assigns emission probabilities of being in the binding state to the different numerical values, the probability function determined using the plurality of counts for the bins of the histogram;
determining a transmission matrix providing pairwise transition probabilities between the four binding states of the nucleic acid;
creating a trellis diagram over a plurality of time steps, each time step corresponding to one signal value of the subset of signal values, wherein the trellis diagram at a given time step includes the four binding states, and wherein binding states at one time step are connected to binding states at a next time step in accordance with the pairwise transition probabilities;
determining an optimal path through the trellis diagram based on the emission probabilities and the pairwise transition probabilities to identify a binding state at each of the plurality of time steps;
creating one or more additional trellis diagrams, each corresponding to a separate bound region of one or more time steps having the bound state; and
determining one or more additional optimal paths through the trellis diagram based on the emission probabilities and the pairwise transition probabilities.

15. The system of claim 12, wherein the sequencing cell further includes a nanopore and has a voltage applied across the sequencing cell, and wherein the four binding states correspond to pore states of the nanopore.

16. The system of claim 15, wherein the voltage includes an alternating signal having a first portion and a second portion relative to a reference voltage, and wherein the first set of signal values is measured during the first portion of the alternating signal.

17. The system of claim 12, wherein the sequencing cell includes the polymerase attached to a nanopore for sequencing the nucleic acid, and wherein obtaining the first set of signal values includes:
   applying a voltage across the sequencing cell, wherein the voltage includes an alternating signal having a first portion and a second portion relative to a reference voltage,
   wherein at least a portion of the first set of signal values are measured during the first portion of the alternating signal when a tag molecule is threaded in the nanopore of the sequencing cell, the tag molecule corresponding to a particular nucleotide.

18. The system of claim 12, wherein using the first classifying procedure includes:
   normalizing the first set of signal values to obtain normalized signal values; and
   comparing normalized signal values to a threshold.

19. The system of claim 12, wherein the subset of signal values is a first subset of signal values, and wherein using the first classifying procedure includes:
   identifying a second subset of signal values as corresponding to the unbound state;
   creating a histogram of the second subset of signal values, the histogram being a data structure storing a plurality of counts, each count corresponding to a number of signal values within a bin, each bin of the histogram corresponding to different numerical values;
   for each of a plurality of unbound sub-states:
      determining a probability function that assigns emission probabilities of being in the unbound sub-state to the different numerical values, the probability function determined using the plurality of counts for the bins of the histogram, the plurality of unbound sub-states including the non-binding state;
   determining a transmission matrix providing pairwise transition probabilities between the plurality of unbound sub-states;
   creating a trellis diagram over a plurality of time steps, each time step corresponding to one signal value of the subset of signal values, wherein the trellis diagram at a given time step includes the plurality of unbound sub-states, and wherein unbound sub-states at one time step are connected to unbound sub-states at a next time step in accordance with the pairwise transition probabilities; and
   determining an optimal path through the trellis diagram based on the emission probabilities and the pairwise transition probabilities to identify an unbound sub-state at each of the plurality of time steps.

20. The system of claim 12, wherein the subset of signal values correspond to disjoint regions that are identified as corresponding to bound states.

* * * * *